(12) United States Patent (10) Patent No.: US 7,695,932 B2
Stephanopoulos et al. (45) Date of Patent: Apr. 13, 2010

(54) GENE TARGETS FOR ENHANCED CAROTENOID PRODUCTION

(75) Inventors: Gregory Stephanopoulos, Winchester, MA (US); Hal S. Alper, Cambridge, MA (US); Yong-Su Jin, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 708 days.

(21) Appl. No.: 11/019,548

(22) Filed: Dec. 23, 2004

(65) Prior Publication Data

US 2006/0188955 A1 Aug. 24, 2006

Related U.S. Application Data

(60) Provisional application No. 60/531,996, filed on Dec. 24, 2003, provisional application No. 60/609,246, filed on Sep. 14, 2004.

(51) Int. Cl.
*C12P 23/00* (2006.01)
*C12N 9/10* (2006.01)
*C12N 1/21* (2006.01)

(52) U.S. Cl. ............... 435/67; 435/193; 435/252.3; 435/252.31; 435/252.33

(58) Field of Classification Search .............. 435/67, 435/193, 252.3, 252.31, 252.33
See application file for complete search history.

(56) References Cited

U.S. PATENT DOCUMENTS

| | | | |
|---|---|---|---|
| 4,683,195 A | 7/1987 | Mullis et al. | |
| 5,013,830 A | 5/1991 | Ohtsuka et al. | |
| 5,149,797 A | 9/1992 | Pederson et al. | |
| 5,220,007 A | 6/1993 | Pederson et al. | |
| 5,256,775 A | 10/1993 | Froehler et al. | |
| 5,366,878 A | 11/1994 | Pederson et al. | |
| 5,403,711 A | 4/1995 | Walder et al. | |
| 5,429,939 A | 7/1995 | Misawa et al. | |
| 5,491,133 A | 2/1996 | Walder et al. | |
| 5,530,188 A | 6/1996 | Ausich et al. | |
| 5,530,189 A | 6/1996 | Ausich et al. | |
| 5,545,816 A | 8/1996 | Ausich et al. | |
| 5,565,350 A | 10/1996 | Kmiec et al. | |
| 5,623,065 A | 4/1997 | Cook et al. | |
| 5,652,355 A | 7/1997 | Metelev et al. | |
| 5,652,356 A | 7/1997 | Agrawal et al. | |
| 5,656,472 A | 8/1997 | Ausich et al. | |
| 5,700,922 A | 12/1997 | Cook et al. | |
| 6,207,384 B1 | 3/2001 | Mekalanos et al. | |
| 6,689,601 B2 | 2/2004 | Koffas et al. | |
| 6,969,595 B2 | 11/2005 | Brzostowicz et al. | |

FOREIGN PATENT DOCUMENTS

WO  WO 02/18617  3/2002

OTHER PUBLICATIONS

Chavez et al., Plant Molecular Biology 28, 173-188 (1995).*
Park et al., Biotechnology and Bioengineering 55, 864-879 (1997).*
Badarinarayana, et al. (2001) "Selection analyses of insertional mutants using subgenic-resolution arrays." National Biotechnology 19(11) 1060-1065.
Elbashir, et al (2001) "Duplexes of 21-nucleotide RNAs mediate RNA interference in cultured mammalian cells." Nature 411:494-498.
Fire, et al (1998) "Potent and specific genetic interference by double-stranded RNA in *Caenorhabditis elegans*." Nature 391:806-811.
Kajiwara, et al. (1994) "Isolation and functional identification of a novel cDNA for astaxanthin biosynthesis from *Haematococcus pluvialis*, and astaxanthin synthesis in *Escherichia coli*." Plant Molecular Biology 29:343-352.
Kato, et al. (1995) "Carotenoid synthesis in *Streptomyces setonii* ISP5395 is induced by the gene crtS, whose product is similar to a sigma factor." Mol. Gen. Genet. 247: 387-390.
Kim, et al. (1997) "Creating auxotrophic mutants in *Methylophilus methylotrophus* AS1 by combining electroporation and chemical mutagenesis." Appl. Microbiol. Biotechnol. 48:105-108.
Lloyd, et al. (1999) "Heterologous expression of soluble methane monooxygenase genes in methanotrophs containing only particulate methane monooxygenase." Archives of Microbiology 171(6) 364-370.
Motoyama, et al. (1994) "Effects of the amplification of the genes coding for the L-threonine biosynthetic enzymes on the L-threonine production from methanol by a gram-negative obligate methylotroph, *Methylobacillus glycogenes*." Appl. Micro Bitechnol. 42(1) 67-72.
Toyama, et al. (1998) "Construction of insertion and deletion mxa mutants of *Methylobacterium extorquens* AM1 by electroporation." FEMS Microbiol. Lett. 166:1-7.
Yoshida, et al. (2001) Biotechnol. Lett. 23:787-791.
Ward, et al. (1982) Photochem. Photobiol. 35:803-808.
Prasher, et al. (1992) "Primary structure of the *Aequorea victoria* green-fluorescent protein." Gene 111: 229-233.

(Continued)

*Primary Examiner*—Chih-Min Kam
(74) *Attorney, Agent, or Firm*—Pearl Cohen Zedek Latzer, LLP; Mark S. Cohen

(57) ABSTRACT

The present invention provides genetically manipulated cells and methods for utilizing same. Methods of enhanced carotenoid synthesis utilizing cells genetically disrupted for a yjiD, hnr or yjfP gene, or further disrupted for a gdhA, gpmB aceE, ppc, talB or fdhF gene, or any combination thereof, or cells inhibited for their expression, activity or function are disclosed. Methods of enhanced carotenoid synthesis utilizing cells genetically engineered to overexpress dxs, idi, yjiD, rpoS, torC, appY, ydgK, yeiA, yedR, tort, arcB, yggT, purDH, yfjN or a combination thereof, or further disrupted for the above-referenced genes are disclosed. Methods for identifying genes involved in optimized production of a carotenoid, and cells disrupted for, or inhibited for the expression, activity or function of genes thus identified are described.

41 Claims, 16 Drawing Sheets

OTHER PUBLICATIONS

Chavez, S. et al., The NADP-glutamate Dehydrogenase of the cyanobacterium Synechocystis 6803: Cloning, Transcriptional Analysis and Disruption of gdhA Gene. Plant Molecular Biology, Apr. 1995, vol. 28, No. 1, pp. 173-188, especially pp. 184-185.

Alper, H. et al., Construction of Lycopene-overproducing E. coli Strains by Combining Systematic and Combinatorial Gene Knockout Targets, Nature Biotechnology, May 2005, vol. 23, No. 5, pp. 612-615, especially pp. 613-615.

* cited by examiner

| Knockout Construct | Lycopene Content (PPM) | Percent Increase |
|---|---|---|
| None | 4763 | 0% |
| Single Knockouts | | |
| gdhA | 5388 | 13% (4) |
| gpmB | 5074 | 7% (2) |
| aceE | 5226 | 9% (4) |
| fdhF | 4918 | 4% (3) |
| Double Knockouts | | |
| gdhA, aceE | 5392 | 13% (4) |
| gdhA, gpmB | 5630 | 18% (3) |
| gdhA, talB | 4883 | 3% (4) |
| Triple Knockouts | | |
| gdhA, aceE, talB | 5679 | 19% (4) |
| gdhA, aceE, fdhF | 6566 | 37% (3) |

Percent Increase

Gene Knockout Target Identification

Systematic

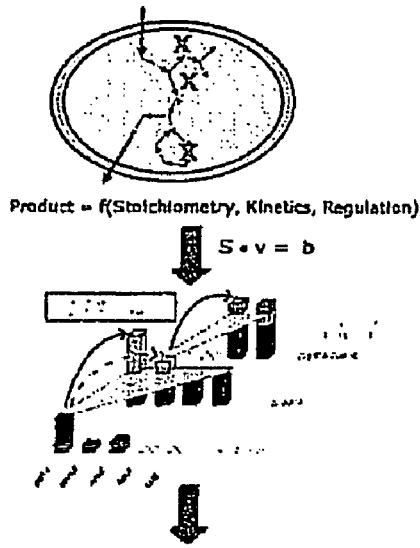

Product = f(Stoichiometry, Kinetics, Regulation)

S · v = b

Gene targets identified through stoichiometric modeling:

| Gene | Function |
|------|----------|
| gdhA | Glutamate dehydrogenase |
| aceE | Pyruvate dehydrogenase |
| gpmB | Phsophoglucomutase II |
| fdhF | Formate dehydrogenase H |

Combinatorial

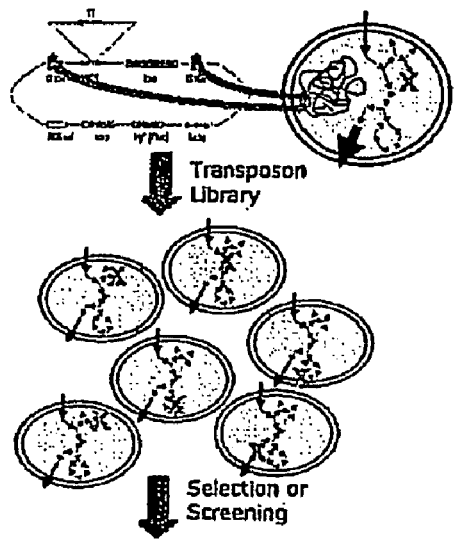

Transposon Library

Selection or Screening

Gene targets identified through combinatorial methods:

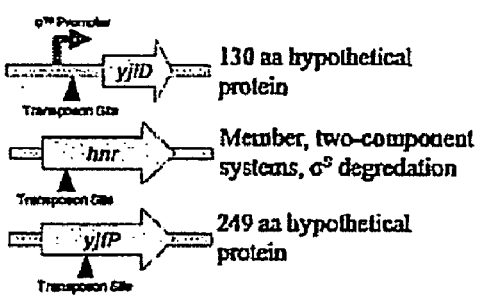

130 aa hypothetical protein

Member, two-component systems, $\sigma^S$ degredation 249 aa hypothetical protein

Figure 8A

GENE TARGETS FOR ENHANCED CAROTENOID PRODUCTION

CROSS REFERENCE TO RELATED APPLICATIONS

This Application claims priority of U.S. Provisional Application Ser. No. 60/531,996, filed Dec. 24, 2003, and U.S. Provisional Application Ser. No. 60/609,246, filed Sep. 14, 2004, which are hereby incorporated by reference, in their entirety.

FIELD OF THE INVENTION

This invention provides genetically engineered cells producing carotenoids. The present invention provides engineered cells genetically disrupted for, or inhibited for genes impacting, directly or indirectly, carotene biosynthesis and methods for utilizing the same, for enhanced carotenoid production. The present invention also provides engineered cells overexpressing genes impacting, directly or indirectly, carotene biosynthesis, and methods of utilizing the same. The present invention provides methods for identifying genes involved in optimized production of a carotenoid.

BACKGROUND OF THE INVENTION

Carotenoids represent one of the most widely distributed and structurally diverse classes of natural pigments, producing pigment colors of light yellow to orange to deep red. Eye-catching examples of carotenogenic tissues include carrots, tomatoes, red peppers, and the petals of daffodils and marigolds, Carotenoids are synthesized by all photosynthetic organisms, as well as some bacteria and fungi. These pigments have important functions in photosynthesis, nutrition, and protection against photooxidative damage. An essential compound, animals and humans must obtain carotenoids through dietary sources, as they do not have the ability to synthesize carotenoids.

Structurally, carotenoids are 40-carbon (C40) terpenoids derived from the isoprene biosynthetic pathway and its five-carbon universal isoprene building block, isopentenyl pyrophosphate (IPP). This biosynthetic pathway can be divided into two portions: the upper isoprene pathway, which leads to the formation of IPP, and the lower carotenoid biosynthetic pathway, which converts IPP into long C30 and C40 carotenogenic compounds.

The genetics of carotenoid pigment biosynthesis has been extremely well studied in the Gram-negative, pigmented bacteria of the genera Pantoea, formerly known as Erwinia. In both *E. herbicola* EHO-10 (ATCC 39368) and *E. uredovora* 20D3 (ATCC 19321), the crt genes are clustered in two genetic units, crt Z and crt EXYIB (U.S. Pat. No. 5,656,472; U.S. Pat. No. 5,5545,816; U.S. Pat. No. 5,530,189; U.S. Pat. No. 5,530,188; U.S. Pat. No. 5,429,939). Despite the similarity in operon structure, the DNA sequences of *E. uredovora* and *E. herbicola* show no homology by DNA-DNA hybridization (U.S. Pat. No. 5,429,939).

Although more than 600 different carotenoids have been identified in nature, only a few are used industrially for food colors, animal feeding, pharmaceuticals and cosmetics. Presently, most of the carotenoids used for industrial purposes are produced by chemical synthesis; however, these compounds are very difficult to produce chemically. Natural carotenoids can either be obtained by extraction of plant material or by microbial synthesis. At the present time, only a few plants are widely used for commercial carotenoid production. However, the productivity of carotenoid synthesis in these plants is relatively low and the resulting carotenoids are very expensive.

A number of carotenoids have been produced from microbial sources. For example, Lycopene has been produced from genetically engineered *E. coli* and *Candia utilis*. β-carotene has been produced from *E. coli, Candia utilis* and *Pfaffia rhodozyma*. Zeaxanthin has been produced from recombinant *E coli* and *Candida utilis*, and Astaxanthin has been produced from *E. coli* and *Pfaffia rhodozyma*.

Additionally genes encoding various elements of the carotenoid biosynthetic pathway have been cloned and expressed in various microbes. For example genes encoding lycopene cyclase, geranylgeranyl pyrophosphate synthase, and phytoene dehydrogenase isolated from *Erwinia herbicola* have been expressed recombinantly in *E. coli*. Similarly genes encoding the carotenoid products geranylgeranyl pyrophosphate, phytoene, lycopene, b-carotene, and zeaxanthin-diglucoside, isolated from *Erwinia uredovora* have been expressed in *E. coli, Zymomonas mobilis*, and *Saccharomyces cerevisiae*. Similarly, the carotenoid biosynthetic genes crtE, crtB, crtI, crtY, and crtZ isolated from Flavobacterium have been recombinantly expressed.

The methods for producing carotenoids available to date, however, suffer from low yields and reliance on expensive precursors and methods. A method that produces higher yields of carotenoids less expensively is clearly needed.

SUMMARY OF THE INVENTION

The invention provides, in one embodiment, a genetically engineered cell with enhanced carotenoid production.

In one embodiment, the cell comprises a disruption in one or more gdhA, gpmB aceE, ppc, talB fdhF genes, or a combination thereof. In one embodiment, the cell comprises a disruption in the genes gdhA and gpmB. In another embodiment, the cell comprises a disruption in the genes gdhA and ppc. In another embodiment, the cell comprises a disruption in the genes gdhA and aceE. In another embodiment, the cell comprises a disruption in the genes gdhA and fdhF. In another embodiment, the cell comprises a disruption in the genes gdhA and talB. In another embodiment, the cell comprises a disruption in the genes gdhA, fdhF and aceE. In another embodiment, the cell comprises a disruption in the genes gdhA, talB and aceE. In another embodiment, the cell overexpresses a dxs, idi, yjiD, rpoS, torC, appY, ydgK, yeiA, yedR, tort, arcB, yggT, purDH or yfjN gene, or a combination thereof. In one embodiment, the cell is a bacterium.

In another embodiment, this invention provides a carotenoid-producing cell, comprising one or more inhibitors of gdHA, gpmB aceE, ppc, talB or fdhF gene activity, or a combination thereof, wherein use of said one or more inhibitors results in enhanced carotenoid production in said cell, as compared to wildtype. In one embodiment, the one or more inhibitors comprise nucleic acid. In another embodiment, the one or more inhibitors suppress or abrogate gdhA and gpmB gene expression or function. In another embodiment, the one or more inhibitors suppress or abrogate gdhA and ppc gene expression or function. In another embodiment, the one or more inhibitors suppress or abrogate gdhA and aceE gene expression or function. In another embodiment, the one or more inhibitors suppress or abrogate gdhA and fdhF gene expression or function. In another embodiment, the one or more inhibitors suppress or abrogate gdhA and talB gene expression or function. In another embodiment, the one or more inhibitors suppress or abrogate gdhA, fdhF and aceE gene expression or function. In another embodiment, the one or more inhibitors suppress or abrogate gdhA, talB and aceE gene expression or function. In another embodiment, the cell overexpresses a dxs, idi, yjiD, rpoS, torC, appY, ydgK, yeiA, yedR, tort, arcB, yggT, purDH or rfjN gene, or a combination thereof. In one embodiment, the cell is a bacterium.

In one embodiment, the cell comprises a disruption in one or more yjiD, hnr or yifP genes, or a combination thereof. In another embodiment, the cell may further comprise a disruption in one or more gdhA, gpmB aceE, ppc, talB or fdhF genes, or a combination thereof. In one embodiment, the cell comprises a disruption in the genes gdhA, aceE and fdhF. In another embodiment, the cell comprises a disruption in the genes gdhA, and yjfP. In another embodiment, the cell comprises a disruption in the genes gdhA, aceE and yjfP. In another embodiment, the cell comprises a disruption in the genes gdhA, aceE, fdhF and yjfP. In another embodiment, the cell comprises a disruption in the genes gpmB and yjiD. In another embodiment, the cell comprises a disruption in the genes gdhA, aceE, and yjiD. In another embodiment, the cell comprises a disruption in the genes gdhA, gpmB and yjiD. In another embodiment, the cell comprises a disruption in the genes gdhA, aceE, hnr and yjfP. In another embodiment, the cell comprises a disruption in the genes gdhA, aceE, hnr, yjfP and yjiD. In another embodiment, the cell comprises a disruption in the genes gdhA, gpmB and yjfP. In another embodiment, the cell overexpresses a dxs, idi, yjiD, rpoS, torC, appY, ydgK, yeiA, yedR, tort, arcB, yggT, purDH or yfjN gene, or a combination thereof. In one embodiment, the cell is a bacterium.

In another embodiment, this invention provides a carotenoid-producing cell, comprising one or more inhibitors of yjiD, hnr or yjfP gene activity, or a combination thereof; wherein use of said one or more inhibitors results in enhanced carotenoid production in said cell, as compared to wildtype. In one embodiment, the cell further comprises one or more inhibitors of gdhA, gpmB aceE, ppc, talB or fdhF gene activity, or a combination thereof. In one embodiment, the one or more inhibitors comprise nucleic acid. In another embodiment, the one or more inhibitors suppress or abrogate gdhA, aceE and fdhF gene expression or function. In another embodiment, the one or more inhibitors suppress or abrogate gdhA and yjfP gene expression or function. In another embodiment, the one or more inhibitors suppress or abrogate gdhA, aceE and yjfP gene expression or function. In another embodiment, the one or more inhibitors suppress or abrogate gdhA, aceE, fdhF and yjfP gene expression or function. In another embodiment, the one or more inhibitors suppress or abrogate gpmB and yjiD gene expression or function. In another embodiment, the one or more inhibitors suppress or abrogate gdhA, aceE, and yjiD gene expression or function. In another embodiment, the one or more inhibitors suppress or abrogate gdhA, gpmB and yjiD gene expression or function. In another embodiment, the one or more inhibitors suppress or abrogate gdhA, aceE, hnr and yjfP gene expression or function. In another embodiment, the one or more inhibitors suppress or abrogate gdhA, aceE, hnr, yjfP and yjiD gene expression or function. In another embodiment, the one or more inhibitors suppress or abrogate gdhA, gpmB and yjfP gene expression or function. In another embodiment, the cell overexpresses a dxs, idi, yjiD, rpoS, torC, appY, ydgK, yeiA, yedR, tort, arcB, yggT, purDH or yfjN gene, or a combination thereof. In one embodiment, the cell is a bacterium.

In one embodiment, the cell is genetically engineered to over-expresses one or more dxs, idi, yjiD, rpoS, torC, appY, ydgK, yeiA, yedR, tort, arcB, yggT, purDH, yfjN genes.

In another embodiment, this invention provides a method for production of carotenoids, comprising genetically disrupting a gdhA, gpmB aceE, ppc, talB or fdhF gene, or a combination thereof in a cell comprising genes involved in the carotenoid biosynthetic pathway and isolating carotenoids from the cell, thereby producing carotenoids. In another embodiment, the cell overexpresses a dxs, idi, yjiD, rpoS, torC, appY, ydgK, yeiA, yedR, tort, arcB, yggT, purDH or yfjN gene, or a combination thereof.

In another embodiment, this invention provides a method for enhanced production of carotenoids, comprising contacting a cell comprising genes involved in the carotenoid biosynthetic pathway with one or more inhibitors of gdhA, gpmB aceE, ppc, talB or fdhF gene expression or function, or a combination thereof and isolating carotenoids from the cell, thereby enhancing production of carotenoids. In another embodiment, the cell overexpresses a dxs, idi, yjiD, rpoS, torC, appY, ydgK, yeiA, yedR, tort, arcB, yggT, purDH or yfjN gene, or a combination thereof.

In another embodiment, this invention provides a method for production of carotenoids, comprising genetically disrupting a yjiD, hnr or yjfP gene, or a combination thereof in a cell comprising genes involved in the carotenoid biosynthetic pathway and isolating carotenoids from the cell, thereby producing carotenoids. In another embodiment, the cell overexpresses a dxs, idi, yjiD, rpoS, torC, appY, ydgK, yeiA, yedR, tort, arcB, yggT, purDH or yfjN gene, or a combination thereof. In one embodiment, the carotenoids comprise astaxanthin, canthaxanthin, beta-carotene, lycopene, phytoene or zeaxanthin.

In another embodiment, this invention provides a method for enhanced production of carotenoids, comprising contacting a cell comprising genes involved in the carotenoid biosynthetic pathway with one or more inhibitors of yjiD, hnr or yjfP gene expression or function, or a combination thereof and isolating carotenoids from the cell, thereby enhancing production of carotenoids. In one embodiment, the carotenoids comprise astaxanthin, canthaxanthin, beta-carotene, lycopene, phytoene or zeaxanthin.

In another embodiment, this invention provides a method for enhanced production of carotenoids, comprising contacting a cell comprising genes involved in the carotenoid biosynthetic pathway with a plasmid comprising a dxs, idi, yjiD, rpoS, torC, appY ydgK, yeiA, yedR, tort, arcB, yggT, purDH, yfjN gene, or a combination thereof, culturing said cell under conditions whereby carotenoids are produced and isolating carotenoids from the cell, thereby enhancing production of carotenoids.

In another embodiment, this invention provides a method of determining gene targets for the optimized production of a metabolite, comprising constructing a flux balance analysis model, applying constraints to said flux balance analysis model, comprising: maximizing cell growth yield subject to a minimization of metabolic adjustment alteration, conducting in silico gene knockout simulations for all genes in the organism's genome, wherein a flux profile comprising a deletion of knocked out genes from the stoichiometry matrix is calculated for said gene knockout simulations; and determining enhanced flux profiles as a measure of optimal production of said metabolite, thereby determining optimized production of a metabolite. In one embodiment, the metabolite comprises a product of the carotenoid biosynthetic pathway. In another embodiment, the in silico gene knockout simulations are conducted on one or more genes simultaneously. In another embodiment, the in silico gene knockout simulations are conducted on one or more genes sequentially. In another embodiment, the calculation of said flux profile comprises imposing a growth rate minimum.

In another embodiment, this invention provides a method of identifying genes involved in optimized production of a carotenoid, comprising constructing a flux balance analysis model, applying constraints to said flux balance analysis model, comprising: maximizing cell growth yield subject to a minimization of metabolic adjustment alteration, conducting in silico gene knockout simulations for all genes in the organism's genome, wherein a flux profile comprising a deletion of knocked out genes from the stoichiometry matrix is calculated for said gene knockout simulations; determining enhanced flux profiles as a measure of optimal production of said metabolite, contacting cells comprising genes involved in the carotenoid biosynthetic pathway with a library of transposon mutagenized genes, selecting cells with enhanced carotenoid synthesis or production, and identifying mutagenized sequences, and inhibiting or abrogating gene expression of combinations of the gene targets identified by flux balance analysis and by transposon mutagenesis, in a cell comprising genes involved in the carotenoid biosynthetic pathway, thereby identifying genes involved in optimized production of a carotenoid. In another embodiment, the method further comprises the step of enhancing gene expression of a gene involved in carotenoid biosynthesis in the cell, which in another embodiment, is a dxs, idi, yjiD, rpoS, torC, appY, ydgK, yeiA, yedR, tort, arcB, yggT, purDH or yfjN gene, or a combination thereof.

According to this aspect of the invention, and in one embodiment, the invention provides a genetically engineered cell with enhanced lycopene production, wherein the cell is genetically disrupted for two or more genes identified by the method described herein. In another embodiment, the invention a cell with enhanced lycopene production, wherein the cell is inhibited or abrogated for expression of two or more genes identified by the method of this invention. In another embodiment, the cell is engineered to over-express a gene involved in carotenoid biosynthesis, which in one embodiment, is a dxs, idi, yjiD, rpoS, torC, appY, ydgK, yeiA, yedR, tort, arcB, yggT, purDH or yfjN gene, or a combination thereof.

BRIEF DESCRIPTION OF THE FIGURES

FIG. 8A shows systematic targets (illustrated on the left) identified through the use of global, stoichiometric modeling to identify gene knockouts which were in silico predicted to increase lycopene by increasing either cofactor or precursor supply. Combinatorial targets (shown on the right) were identified through the use of transposon mutagenesis. These targets were combined to create the unique set of 64 mutant strains used in this study. FIG. 8 C, D and E demonstrate clustering analysis depicting the interaction of systematic and combinatorial targets. Lycopene production profiles across the 48 hour shaker-flask fermentation are clustered, resulting in the dendrograms as shown. In panel C, the purely systematic strains have a stacked dendrogram which is visually illustrated with a concentric bubble-plot. Conversely, the addition of a combinatorial target, hnr in this case, decouples the systematic design and causes a disjoint pattern in the dendrogram and bubble-plot. This has the implication that local, metabolic gene targets are more accessible through a sequential search than global, regulatory targets which require a simultaneous search which is sensitive to the genetic background of the strain. Panel E compares the average, relative production profiles for the three clusters shown in Panels C and D.

DETAILED DESCRIPTION OF THE INVENTION

Figure 1:
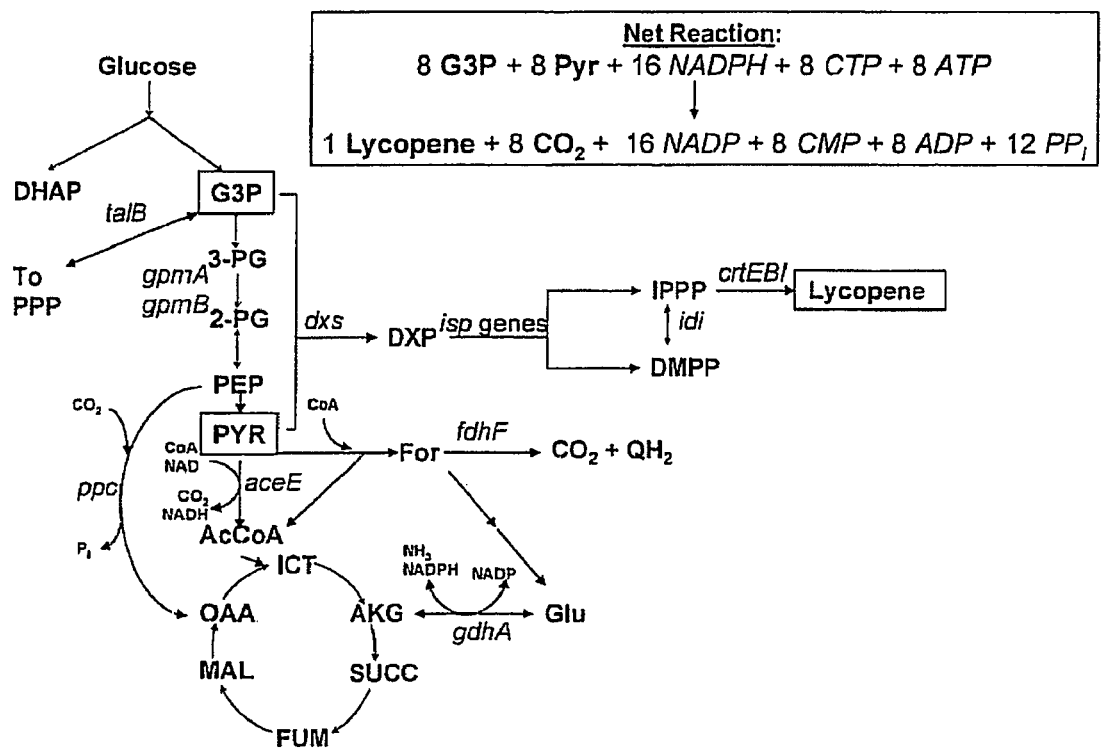
FIG. 1 depicts the lycopene production pathway along with identified gene targets. The lycopene pathway begins with the condensation of the key glycolytic intermediates, glyceraldehyde 3-P (G3P) and pyruvate (PYR) and continues in a nearly linear pathway. The genes encoding for idi and dxs are typical targets for lycopene over-expression along this pathway. In the engineered strain used in this study, the idi, ispFD, and dxs genes are overexpressed. Identified gene targets are also shown as they are connected to lycopene production.

This invention provides, in one embodiment, recombinant cells, including, in one embodiment, microorganisms and methods for utilizing same, for production of carotenoids. The methods and cells, in one embodiment, enable high carotenoid yields, inexpensively, and reproducibly. The invention also provides, in another embodiment, cells inhibited for genes impacting carotenoid biosynthesis, or genetic disruption of said genes, which result in enhanced carotenoid production. In one embodiment, microbial production of carotenoid compounds according to the methods of this invention, serve as an alternative to chemical synthesis.

Carotenoids are terpenoids derived from an isoprene building block, isopentenyl pyrophosphate (IPP). Carotenoids are produced via the general isoprenoid biosynthetic pathway by bacteria, fungi and plants. These pigments protect organisms against photooxidative damage, as well as functioning as anti-tumor agents, free radical-scavenging anti-oxidants, and enhancers of the immune response. Additionally, they are used commercially in pigmentation of cultured fish and shellfish.

In one embodiment, the term "isoprenoid compound" refers to any compound which is derived via the pathway beginning with isopentenyl pyrophosphate (IPP) and formed by the head-to-tail condensation of isoprene units which may be, in one embodiment, of 5, or, in another embodiment, of 10, or, in another embodiment, of 15, or, in another embodiment, of 20, or, in another embodiment, of 30 or, in another embodiment, of 40 carbons in length. In another embodiment, isoprenoid compounds may comprise isoprenoid pigments, which in one embodiment, refers to a class of compounds, which typically have strong light absorbing properties.

The isoprenoid biosynthetic pathway can be divided, in one embodiment, into two portions: the upper isoprene pathway, which leads to the formation of IPP, and the lower carotenoid biosynthetic pathway, which converts IPP into long C30 and C40 carotenogenic compounds.

The terms "upper isoprenoid pathway" and "upper pathway" are used interchangeably and refer, in one embodiment, to enzymes involved in converting pyruvate and glyceraldehyde-3-phosphate to farnesyl pyrophosphate (FPP). Genes encoding these enzymes include, but are not limited to: the "dxs" gene (encoding 1-deoxyxylulose-5-phosphate synthase); the "dxr" gene (encoding 1-deoxyxylulose-5-phosphate reductoisomerase; also known as the ispC ); the "ispD" gene (encoding a 2C-methyl-D-erythritol cytidyltransferase enzyme; also known as ygbP); the "ispE" gene (encoding 4-diphosphocytidyl-2-C-methylerythritol kinase; also known as ychB); the "ispF" gene (encoding a 2C-methyl-D-erythritol 2,4-cyclodiphosphate synthase; also known as ygbB); the "pyrG" gene (encoding a CTP synthase; also known as ispF); the "lytB" gene (also known as ispH) involved in the formation of dimethylallyl diphosphate; the "gcpE" gene (also known as ispG) involved in the synthesis of 2-C-methyl-D-erythritol 4-phosphate; the "idi" gene (responsible for the intramolecular conversion of IPP to dimethylallyl pyrophosphate); and the "ispA" gene (encoding geranyltransferase or farnesyl diphosphate synthase) in the isoprenoid pathway.

In one embodiment, the term "Dxs" refers to the 1-deoxyxylulose-5-phosphate synthase enzyme encoded by the dxs gene. In another embodiment, the term "Dxr" refers to the 1-deoxyxylulose-5-phosphate reductoisomerase enzyme encoded by the dxr gene. In another embodiment, the term "YgbP" or "IspD" refers to the 2C-methyl-D-erythritol cytidyltransferase enzyme encoded by the ygbP or ispD gene. In another embodiment, the terms ygbP or ispD, are used interchangeably. In another embodiment, the terms YgbP or IspD are used interchangeably in this application, to designate ygbP or ispD gene products.

In another embodiment, the term "YchB" or "IspE" refers to the 4-diphosphocytidyl-2-C-methylerythritol kinase enzyme encoded by the ychB or ispE gene. In one embodiment, the terms for the genes, ychB or ispE, are used interchangeably and the terms for the ychB or ispE, gene products, are, in another embodiment, referred to as YchB or IspE, and are used interchangeably in this application.

In another embodiment, the term "YgbB" or "IspF" refers to the 2C-methyl-d-erythritol 2,4-cyclodiphosphate synthase enzyme encoded by the ygbB or ispF gene. In one embodiment, the terms for the genes, ygbB or ispF, are used interchangeably, and the terms for the gene product, YgbB or IspF are used interchangeably in this application.

In another embodiment, the term "PyrG" refers to a CTP synthase enzyme encoded by the pyrG gene. In another embodiment, the term "IspA" refers to Geranyltransferase or farnesyl diphosphate synthase enzyme as one of prenyl transferase family encoded by ispA gene.

In another embodiment, the term "LytB" refers to protein having a role in the formation of dimethylallyl-pyrophosphate in the isoprenoid pathway and which is encoded by lytB gene.

In another embodiment, the term "GcpE" refers to a protein having a role in the formation of 2-C-methyl-D-erythritol 4-phosphate in the isoprenoid pathway.

In one embodiment the terms "lower carotenoid biosynthetic pathway" and "lower pathway" will be used interchangeably and refer to those enzymes which convert FPP to a suite of carotenoids. These include those genes and gene products that are involved in the synthesis of either diapophytoene (whose synthesis represents the first step unique to biosynthesis of $C_{30}$ carotenoids) or phytoene (whose synthesis represents the first step unique to biosynthesis of $C_{40}$ carotenoids). All subsequent reactions leading to the production of various $C_{30}$-$C_{40}$ carotenoids are included within the lower carotenoid biosynthetic pathway. These genes and gene products comprise all of the "crt" genes including, but not limited to: crtM, crtN, crtN2, crtE, crtX, crtY, crtI, crtB, crtZ, crtW, crtO, crtR, crtA, crtC, crtD, crtF, and crtU. The term "lower carotenoid biosynthetic enzyme", in another embodiment, is an inclusive term referring to any and all of the enzymes in the lower pathway including, but not limited to: CrtM, CrtN, CrtN2, CrtE, CrtX, CrtY, CrtI, CrtB, CrtZ, CrtW, CrtO, CrtR, CrtA, CrtC, CrtD, CrtF, and CrtU.

"$C_{30}$ diapocarotenoids" consist of six isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. $C_{30}$ carotenoids may be formally derived from the acyclic $C_{30}H_{42}$ structure, having a long central chain of conjugated double bonds, by: (i) hydrogenation (ii) dehydrogenation, (iii) cyclization, (iv) oxidation, (v) esterification/glycosylation, or any combination of these processes.

"Tetraterpenes" or "$C_{40}$ carotenoids" consist of eight isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. $C_{40}$ carotenoids may be formally derived from the acyclic $C_{40}H_{56}$ structure. Non-limiting examples of $C_{40}$ carotenoids include: phytoene, lycopene, β-carotene, zeaxanthin, astaxanthin, and canthaxanthin.

In one embodiment, the term "IspA" refers to the protein encoded by the ispA gene, and whose activity catalyzes a sequence of 3 prenyltransferase reactions in which geranyl pyrophosphate (GPP), farnesyl pyrophosphate (FPP), and geranylgeranyl pyrophosphate (GGPP) are formed.

In another embodiment, the term "CrtN1" or "CrtN, copy1" refers to copy 1 of the diapophytoene dehydrogenase enzyme encoded by crtN1 gene. In another embodiment, the term "CrtN2" or "CrtN copy2" refers to copy 2 of the diapophytoene dehydrogenase enzyme (Crt) encoded by crtN2 gene.

In another embodiment, the term "CrtE" refers to geranylgeranyl pyrophosphate synthase enzyme encoded by crtE gene, which converts trans-trans-farnesyl diphosphate and isopentenyl diphosphate into pyrophosphate and geranylgeranyl diphosphate. In another embodiment, the term "CrtX" refers to the zeaxanthin glucosyl transferase enzyme encoded by the crtX gene, and which glycosolates zeaxanthin to produce zeaxanthin-b-diglucoside.

In one embodiment, the term "CrtY" refers to the lycopene cyclase enzyme encoded by the crtY gene and which catalyzes conversion of lycopene to b-carotene. In another embodiment, the term "CrtI" refers to the phytoene desaturase enzyme encoded by the crtI gene and which converts phytoene into lycopene via the intermediaries of phytofluene, zeta-carotene, and neurosporene by the introduction of 4 double bonds.

In another embodiment, the term "CrtB" refers to the phytoene synthase enzyme encoded by the crtB gene which catalyses the reaction from prephytoene diphosphate to phytoene. In another embodiment, the term "CrtZ" refers to the b-carotene hydroxylase enzyme encoded by crtZ gene which catalyses the hydroxylation reaction from b-carotene to zeaxanthin.

In another embodiment, the term "CrtO" refers to the β-carotene ketolase enzyme encoded by crtO gene which catalyses conversion of β-carotene into canthaxanthin (two ketone groups) via echinenone (one ketone group) as the intermediate.

In another embodiment the term "CrtW" refers to a β-carotene ketolase enzyme encoded by the crtW gene, which catalyzes an oxidation reaction where a keto group is introduced on the ionone ring of cyclic carotenoids. It is known that CrtW ketolases typically exhibit substrate flexibility. The term "carotenoid ketolase" or "ketolase" refers to the group of enzymes that can add keto groups to the ionone ring of cyclic carotenoids.

In another embodiment, the term "carotenoid compound" or "carotenoid" refers to a class of hydrocarbons (carotenes) and their oxygenated derivatives (xanthophylls) consisting of eight isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. All carotenoids may be formally derived from the acyclic $C_{40}H_{56}$ structure (Formula I below), having a long central chain of conjugated double bonds, by (i) hydrogenation. (ii) dehydrogenation, (iii) cyclization, or (iv) oxidation or any combination of these processes.

Formula I

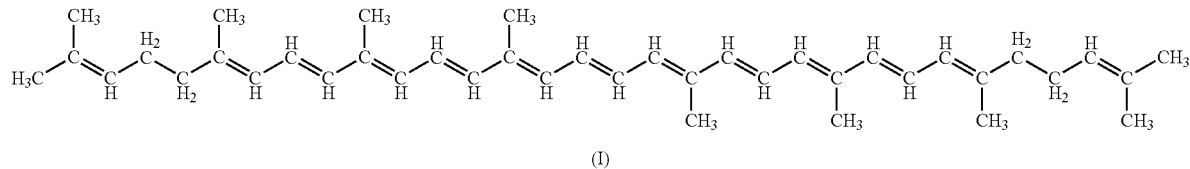

(I)

In another embodiment, carotenoids also include compounds that arise from certain rearrangements of the carbon skeleton (I), or by the (formal) removal of part of this structure.

In another embodiment, carotenoids are represented by the structure of the formula (II):

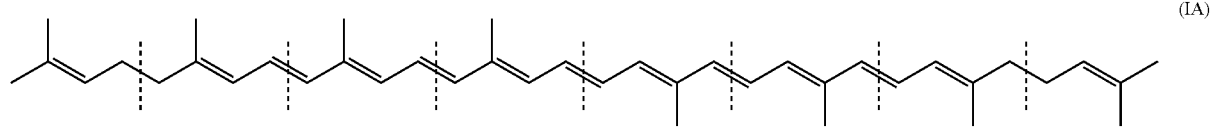

(IA)

where the broken lines indicate formal division into isoprenoid units.

Genes Involved in Carotenoid Production

Carotenoid synthesis is catalyzed by relatively small numbers of clustered genes in various microorganisms. For example, carotenoid synthesis is catalyzed by 11 different genes within 12 kb of DNA from *Myxococcus xanthus* and 8 genes within 9 kb of DNA from *Rhodobacter sphaeroides*. In some microorganisms, such as *Thermus thermophilus*, these genes are plasmid-borne.

The enzyme pathway involved in the biosynthesis of carotenoids can be conveniently viewed in two parts, the upper isoprenoid pathway providing for the conversion of pyruvate and glyceraldehyde-3-phosphate to isopentenyl pyrophosphate and the lower carotenoid biosynthetic pathway, which provides for the synthesis of phytoene and all subsequently produced carotenoids. The upper pathway is ubiquitous in many microorganisms.

IPP biosynthesis, a precursor produced in the upper isoprenoid pathway, occurs, in one embodiment, through the well-known acetate/mevalonate pathway. In another embodiment, an alternate mevalonate-independent pathway for IPP biosynthesis has been characterized in bacteria and in green algae and higher plants. The carotenoid biosynthetic pathway is schematically depicted in FIG. 1. In one embodiment, the first step of the pathway involves the condensation of two 3-carbon molecules (pyruvate and D-glyceraldehyde 3-phosphate) to yield a 5-carbon compound known as D-1-deoxyxylulose-5-phosphate. This reaction occurs by the DXS enzyme, encoded by the dxs gene. Next, the isomerization and reduction of D-1-deoxyxylulose-5-phosphate yields 2-C-methyl-D-erythritol-4-phosphate. One of the enzymes involved in the isomerization and reduction process is D-1-deoxyxylulose-5-phosphate reductoisomerase (DXR), encoded by the gene dxr. 2-C-methyl-D-erythritol-4-phosphate is subsequently converted into 4-diphosphocytidyl-2C-methyl-D-erythritol in a CTP-dependent reaction by the enzyme encoded by the non-annotated gene ygbP, also referred to as ispD as a part of the isp gene cluster (SwissProtein Accession #Q46893).

Next, the 2nd position hydroxy group of 4-diphosphocytidyl-2C-methyl-D-erythritol can be phosphorylated in an ATP-dependent reaction by the enzyme encoded by the ychB gene. This product phosphorylates 4-diphosphocytidyl-2C-methyl-D-erythritol, resulting in 4-diphosphocytidyl-2C-methyl-D-erythritol 2-phosphate. The ychB gene is also referred to as ispE, also a part of the isp gene cluster (SwissProtein Accession #P24209). Finally, the product of ygbB gene converts 4-diphosphocytidyl-2C-methyl-D-erythritol 2-phosphate to 2C-methyl-D-erythritol 2,4-cyclodiphosphate in a CTP-dependent manner. This gene is also a part of the isp gene cluster, and is referred to as ispF (SwissProtein Accession #P36663), in another embodiment.

It is known that 2C-methyl-D-erythritol 2,4-cyclodiphosphate can be further converted into IPP to ultimately produce carotenoids in the carotenoid biosynthesis pathway. However, the reactions leading to the production of isopentenyl monophosphate from 2C-methyl-D-erythritol 2,4-cyclodiphosphate are not yet well-characterized. The enzymes encoded by the lytB and gcpE genes, in one embodiment, are thought to participate in the reactions leading to formation of isopentenyl pyrophosphate (IPP) and dimethylallyl pyrophosphate (DMAPP). In another embodiment, additional gene products are involved.

IPP may be isomerized, in another embodiment, to DMAPP via IPP isomerase, encoded by the idi gene, however participation of this enzyme is not necessary and may be bypassed vias the 2-C-methyl-D-erythritol 4-phosphate (MEP) pathway. In another embodiment, the MEP pathway branches before IPP synthesis and separately produces IPP and DMAPP via the lytB gene product.

The formation of phytoene is produced via the lower carotenoid biosynthetic pathway. The synthesis of phytoene occurs, in one embodiment, via isomerization of IPP to dimethylallyl pyrophosphate (DMAPP). This reaction, in another embodiment, is followed by a sequence of 3 prenyltransferase reactions. In one embodiment, two of these reactions are catalyzed by ispA, leading to the creation of geranyl pyrophosphate (GPP; a 10-carbon molecule) and farnesyl pyrophosphate (FPP; 15-carbon molecule). In one embodiment, the genes CrtN1 and crtN2 convert farnesyl pyrophosphate to a 30-carbon pigment.

According to this aspect of the invention, and in one embodiment, the gene crtE, encoding GGPP synthetase is responsible for the 3rd prenyltransferase reaction, which may occur, leading to the synthesis of phytoene. This reaction adds IPP to FPP to produce a 20-carbon molecule, geranylgeranyl pyrophosphate (GGPP). A condensation reaction of two molecules of GGPP may then occur, according to this aspect of the invention, to form phytoene (PPPP), the first 40-carbon molecule of the lower carotenoid biosynthesis pathway. This enzymatic reaction is catalyzed by crtB, encoding phytoene synthase, In one embodiment, lycopene, which imparts a "red"-colored spectra, is produced from phytoene through four sequential dehydrogenation reactions by the removal of eight atoms of hydrogen, catalyzed by the gene crtI (encoding phytoene desaturase). Intermediaries in this reaction are phtyofluene, zeta-carotene, and neurosporene.

In one embodiment, lycopene cyclase (crtY) converts lycopene to β-carotene, which in another embodiment, is converted to zeaxanthin via a hydroxylation reaction resulting from the activity of β-carotene hydroxylase (encoded by the crtZ gene). B-cryptoxanthin is an intermediate in this reaction, in one embodiment.

In another embodiment, β-carotene is converted to canthaxanthin by β-carotene ketolase encoded by the crtW gene, and echinenone in an intermediate in this reaction, in one embodiment. In another embodiment, canthaxantin may be converted to astaxanthin by β-carotene hydroxylase encoded by the crtZ gene. In one embodiment, adonbirubrin is an intermediate in this reaction.

In another embodiment, zeaxanthin may be converted to zeaxanthin-β-diglucoside, via the activity of zeaxanthin glucosyl transferase (crtX). In one embodiment, zeaxanthin may be converted to astaxanthin by β-carotene ketolase encoded by crtW, crtO or bkt. In one embodiment, adonixanthin is an intermediate in this reaction.

Optimization of Carotenoid Production

Figure 5:
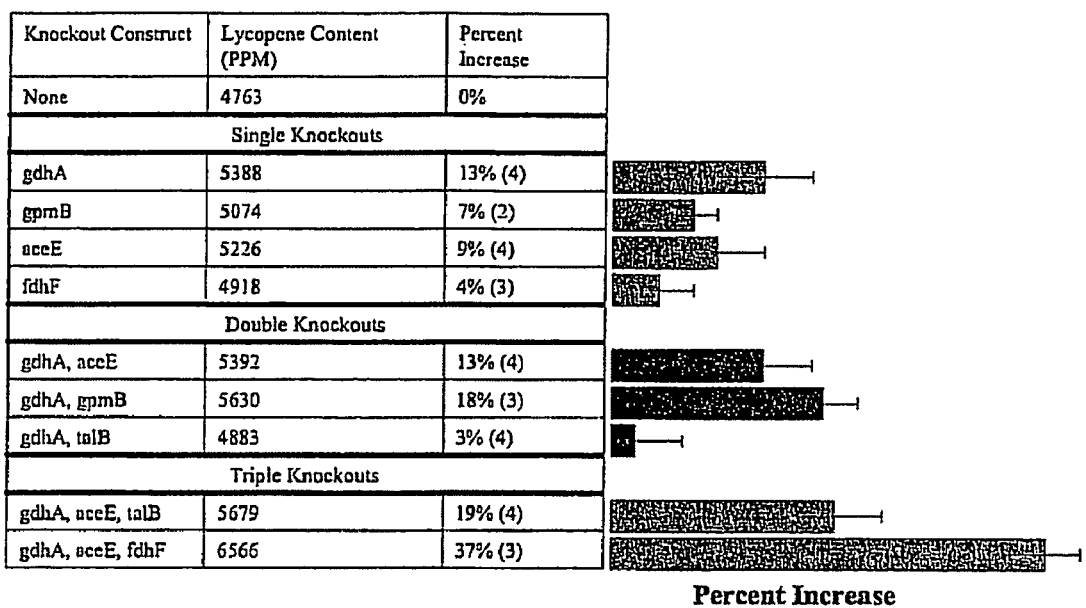
FIG. 5 demonstrates the experimental results obtained for single and multiple gene knockouts. Lycopene production is shown in ppm along with percent increases compared with the corresponding levels obtained in the parental strain and grown in replicate cultures. This data is consistent with the simulations presented in FIG. 3. Total lycopene content increases with multiple knockouts obtained along the path of highest production. Numbers in parenthesis represent standard deviations among replicate experiments FIG. 6 demonstrates lycopene production in a parental strain versus that obtained in random transposon libraries and the predicted single knockout targets. The results of the selected single knockout targets are juxtaposed to random transposons. These results indicate the significance of the systematically selected single gene targets of gdhA, gpmB, and aceE. A heterogeneous culture of a random transposon mutagenesis library appeared to decrease the lycopene production on average. To establish the heterogeneity of these libraries, ten colonies were selected and exhibit similar production levels to that of the libraries.
Figure 7:
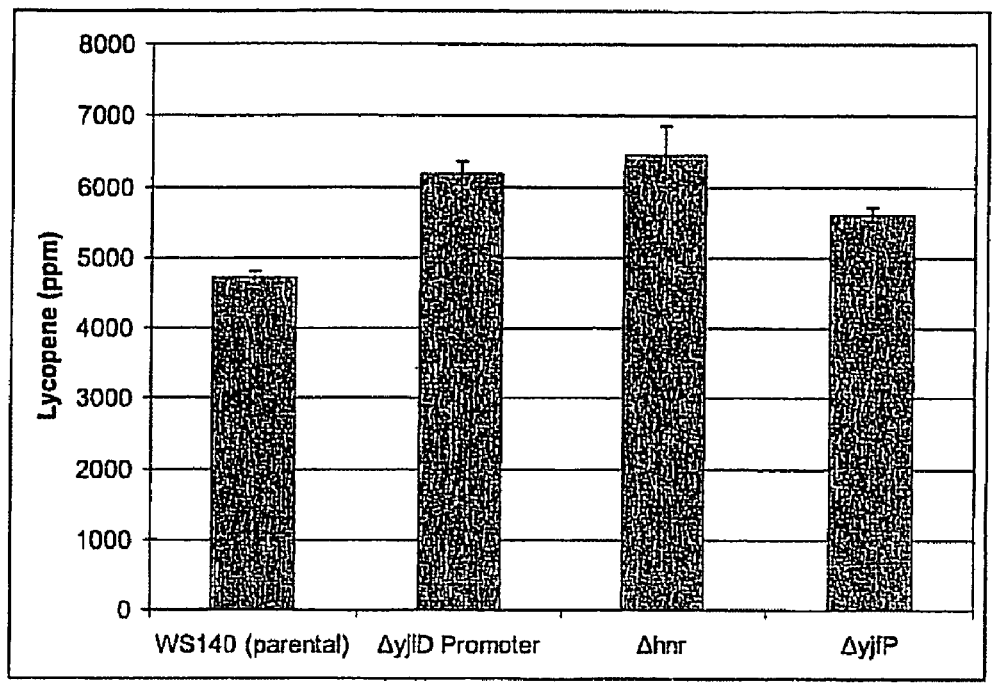
FIG. 7 demonstrates lycopene production in individual combinatorial targets of yjiD, hnr, and yjfP and the parental strain. Lycopene production is increased in each of the combinatorial targets as compared to the parental strain.

Since multiple pathways are required for carotenoid production, in one embodiment, genes impacting carotenoid biosynthesis in a given microorganism and/or cell may be individually "knocked out", or several genes may be "knocked out" in combination to successfully produce higher yields of carotenoids (FIG. 5 or 7). The phenotype may not be additive in nature, in one embodiment.

In one embodiment, the genes involved may include yjiD, hnr (also known as RssB), yjfP, or a combination thereof.

The gene hnr encodes a response regulator, which has been reported to be responsible for recruiting the proteolysis of the stationary phase sigma factor (rpoS), and rpoS has been implicated as playing an important role in the production of carotenoids in E. coli.

In one embodiment, the hnr or RssB gene has a nucleic acid sequence that corresponds to that set forth in Genbank Accession Nos: U93704, AJ410309 or X66003, or encodes a protein sequence that corresponds to that set forth in Genbank Accession Nos: CAA46802, CAC44355 or AAB71132.

The gene yjfP encodes a 249 amino acid protein, which is currently not annotated, but has been categorized as a non-peptidase homologue through homology search.

In one embodiment, the yjfP gene has a nucleic acid sequence that corresponds to that set forth in Genbank GeneID Number: 948707, or one that corresponds to that set forth in Genbank Accession Nos: AE016771, AE016771, AD1051, AAG59386, AAN45762, AAM84229 or F86115; or encodes a protein sequence that corresponds to that set forth in Genbank Accession Nos: NP_418611, AAN83699, AD1051, F86115, AAN4576, AAM84229 or AAG59386.

yjiD encodes a 130 amino acid protein with an as yet unknown function. In one embodiment, the yjiD gene encodes a protein sequence that corresponds to that set forth in Genbank Accession Nos: NP_418746, NP_313312, NP_839588, NP_757253, NP_709906, NP_290943, AAN83827, A86131, S56551, AAN45613, P39375 or AAG59509.

In one embodiment, genens may be "knocked-out" via a variety of means well known in the art, and may include gene activation by the introduction of a transposon at a variety of sites, as will be understood by one skilled in the art, and as exemplified herein. In one embodiment, the transposon will insert in between the promoter and gene region, and thus inactivate the gene.

It is to be understood that the methods of this invention, and cells of this invention, will refer to genes which are "knocked out" for the coding region of the gene, or a part of the gene which begins from the promoter until the start of the gene. In the latter case, such knocked out genes may be referred to as $\Delta_P$ gene. In one embodiment, a $\Delta_P$ yjiD cell or method of using the same is part of this invention. In one embodiment, the methods and cells of this invention, which comprise a $\Delta_P$ gene will also serve to indicate any modification of the natural regulation occurring with the particular gene target.

Using these three identified targets, in another embodiment, it is possible to create a total of seven gene combinations of single, double, and triple combinatorial target mutations, and create genetically engineered cells expressing the same. These cells may then, in another embodiment, be used to mass-produce carotenoids.

In another embodiment, the cells, which in other embodiments are bacteria, may further comprise a disruption in one or more gdhA, gpmB aceE, ppc, talb or fdhF genes, or a combination thereof. A complete analysis of the 64 strains comprising all combinations of the eight systematic and eight combinatorial mutations (as exemplified hereinbelow) was conducted herein, in terms lycopene production demonstrated extremely high-yield of carotenoids in the generated strains.

In one embodiment, the gdhA gene has a nucleic acid sequence that corresponds to that set forth in Genbank Accession Nos: Y08696, AF035935, AY137769, AB086412, X72855, AF239256. AF321093, AF332586, AF069527, AB024549, AF009234, AF009232, Y18494, Y15166, Y15784, AF092086, AF056335, U89520, U82241, U82240, X77454, X73990, X00988, X12370, X16121, X83393, J01615, L19995, M24021 or K02499.

In one embodiment, the gpmB gene has a nucleic acid sequence that corresponds to that set forth in Genbank Accession Nos: AB052566, AF246335, AB059427, and NCBI's GeneID) Nos: 1243981, 1135031 2548726 1078078 996982 933141 948918 or 1098010.

In one embodiment, the aceE gene has a nucleic acid sequence that corresponds to that set forth in Genbank Accession Nos: X94981, AJ242516, AB059427, S67363, V01498 or NCBI's (GeneID No: 1244242, 907942, 881326, 944834, 1154647 or 887246.

In one embodiment, the ppc gene has a nucleic acid sequence that corresponds to that set forth in Genbank Accession Nos: NM_112356, D42166, X79090, AY251482, AJ252948, AJ252932, AJ252931, AJ252930, AJ252929, AJ252928, AJ231302, AJ231301, AF160253, AF495586, AB083298, AF406314, AF268091, X95861, AF177946, E16358, AF071788 or X05903.

In one embodiment, the talB gene has a nucleic acid sequence that corresponds to that set forth in Genbank Accession Nos: AF087310, D13161, S80045 or T59433, or NCBI's GeneID Nos: 2665946, 1173307, 1246518, 1036025, 1076428, 1251525, 1067000 or 944748.

In one embodiment, the fdhF gene has a nucleic acid sequence that corresponds to that set forth in Genbank Accession Nos: AF146729, X54696, M64798, or NCBI's GeneID Nos: 1250699, 1173189, 1145548, 1069713, 960045, 1211438 or 1038553.

In another embodiment, production of carotenoids in such microorganisms may be accomplished via the further introduction of genes that comprise the lower pathway for the biosynthesis of the desired carotenoid. In another embodiment, in microorganisms and/or host cells where IPP synthesis is not ubiquitously present, the genes necessary for the production of IPP may be introduced.

By using various combinations of the genes of the lower carotenoid pathway, in another embodiment, different carotenoids and carotenoid derivatives may be synthesized using the methods of the present invention, and such compounds may be produced at high yields. For example, the gene cluster crtEIB enables the production of lycopene, and crtEXYIB enables the production of β-carotene. Addition of the crtZ to crtEXYIB enables the production of zeaxanthin, while the crtEXYIBZO cluster leads to production of astaxanthin and canthaxanthin In one embodiment, the bacterium comprises a disruption in the genes gdhA, aceE and fdhF. In another embodiment, the bacterium comprises a disruption in the genes gdhA and yjfP. In another embodiment, the bacterium comprises a disruption in the genes gdhA, aceE and yjfP. In another embodiment, the bacterium comprises a disruption in the genes gdhA, aceE, fdhF and yjfP. In another embodiment, the bacterium comprises a disruption in the genes gpmB and yjiD. In another embodiment, the bacterium comprises a disruption in the genes gdhA, aceE, and yjiD. In another embodiment, the bacterium comprises a disruption in the genes gdhA, gpmB and yjiD. In another embodiment, the bacterium comprises a disruption in the genes. gdhA, aceE, hnr and yjfP. In another embodiment, the bacterium comprises a disruption in the genes gdhA, aceE, hnr, yjfP and yjiD. In another embodiment, the bacterium comprises a disruption in the genes gdhA, gpmB and yjfP.

In another embodiment, a eukaryotic cell genetically engineered to comprise carotenoid biosynthetic genes, further comprising a deletion in one or more yjiD, hnr or yjfP genes, is considered as part of this invention. In another embodiment, such cells may be further engineered to comprise a deletion in one or more gdhA, gpmB aceE, ppc, talb or fdhF genes. Such cells may include yeast, such as those belonging to the *Candida* genus, or others well known to one skilled in the art.

In one embodiment, the term "gene" refers to a nucleic acid fragment that is capable of being expressed as a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The genetically engineered bacteria and other cells of this invention may be engineered to be deficient in the indicated genes via any means as will be known to one skilled in the art. In one embodiment, a construct is introduced in the bacteria of this invention, such that it is possible to select for homologous recombination events in the bacterium for gene knock-out procedures. One ordinarily skilled in the art can readily design a knock-out construct including both positive and negative selection genes for efficiently selecting transfected cells that underwent a homologous recombination event with the construct.

In another embodiment, a cell of this invention, including a bacterial cell, may be genetically disrupted for, or inhibited for gene expression or activity, for the genes listed in table 1.

TABLE 1

Embodiments of genes disrupted, or inhibited in the methods, cells, (including bacteria) of this invention

| | | | | | | | | |
|---|---|---|---|---|---|---|---|---|
| 1 | yjiD | hnr | aceE | ppc | talB | fdhF | gdhA | yjfP |
| 2 | yjiD | hnr | aceE | ppc | talB | yjfP | fdhF | |
| 3 | yjiD | hnr | aceE | ppc | talB | gdhA | fdhF | |
| 4 | yjiD | hnr | aceE | ppc | talB | gdhA | yjfP | |
| 5 | yjiD | hnr | aceE | ppc | fdhF | gdhA | yjfP | |
| 6 | yjiD | hnr | aceE | talB | fdhF | gdhA | yjfP | |
| 7 | yjiD | hnr | ppc | talB | fdhF | yjfP | gdhA | |
| 8 | yjiD | aceE | ppc | talB | fdhF | gdhA | yjfP | |
| 9 | hnr | aceE | ppc | talB | fdhF | gdhA | yjfP | |
| 10 | yjiD | hnr | aceE | ppc | talB | fdhF | yjfP | |
| 11 | yjiD | hnr | aceE | ppc | talB | fdhF | gdhA | |
| 12 | aceE | ppc | talB | fdhF | gdhA | yjfP | | |
| 13 | hnr | aceE | ppc | talB | fdhF | yjfP | | |
| 14 | hnr | aceE | ppc | talB | fdhF | gdhA | | |
| 15 | yjiD | ppc | talB | fdhF | gdhA | yjfP | | |
| 16 | yjiD | aceE | ppc | talB | fdhF | yjfP | | |
| 17 | yjiD | aceE | ppc | talB | fdhF | gdhA | | |
| 18 | yjiD | hnr | aceE | ppc | talB | yjfP | | |
| 19 | yjiD | hnr | aceE | ppc | talB | gdhA | | |
| 20 | yjiD | hnr | aceE | ppc | talB | fdhF | | |
| 21 | ppc | talB | fdhF | gdhA | yjfP | | | |
| 22 | aceE | ppc | talB | fdhF | yjfP | | | |
| 23 | aceE | ppc | talB | fdhF | gdhA | | | |
| 24 | hnr | ppc | talB | gdhA | yjfP | | | |
| 25 | hnr | ppc | talB | fdhF | yjfP | | | |
| 26 | hnr | ppc | talB | fdhF | gdhA | | | |
| 27 | hnr | aceE | ppc | talB | yjfP | | | |
| 28 | hnr | aceE | ppc | talB | gdhA | | | |
| 29 | hnr | aceE | ppc | talB | fdhF | | | |
| 30 | yjiD | ppc | talB | fdhF | yjfP | | | |
| 31 | yjiD | ppc | talB | fdhF | gdhA | | | |
| 32 | yjiD | aceE | ppc | talB | yjfP | | | |
| 33 | yjiD | aceE | ppc | talB | gdhA | | | |
| 34 | yjiD | aceE | ppc | talB | fdhF | | | |
| 35 | yjiD | hnr | aceE | ppc | yjfP | | | |
| 36 | yjiD | hnr | aceE | ppc | gdhA | | | |
| 37 | yjiD | hnr | aceE | ppc | fdhF | | | |
| 38 | yjiD | hnr | aceE | ppc | talB | | | |
| 39 | gdhA | aceE | yjfP | talB | | | | |
| 40 | fdhF | gdhA | aceE | talB | | | | |
| 41 | fdhF | gdhA | aceE | yjfP | | | | |
| 42 | ppc | fdhF | gdhA | talB | | | | |
| 43 | ppc | fdhF | gdhA | yjfP | | | | |
| 44 | ppc | fdhF | gdhA | aceE | | | | |
| 45 | hnr | fdhF | yjfP | talB | | | | |
| 46 | hnr | fdhF | yjfP | aceE | | | | |
| 47 | hnr | fdhF | yjfP | gdhA | | | | |
| 48 | hnr | ppc | fdhF | talB | | | | |
| 49 | hnr | ppc | fdhF | yjfP | | | | |
| 50 | hnr | ppc | fdhF | aceE | | | | |
| 51 | hnr | ppc | fdhF | gdhA | | | | |

TABLE 1-continued

Embodiments of genes disrupted, or inhibited in the methods, cells, (including bacteria) of this invention

| 52 | yjiD | talB | fdhF | yjfP |
| 53 | yjiD | talB | fdhF | aceE |
| 54 | yjiD | gdhA | talB | yjfP |
| 55 | yjiD | gdhA | talB | aceE |
| 56 | yjiD | gdhA | talB | fdhF |
| 57 | yjiD | ppc | gdhA | yjfP |
| 58 | yjiD | ppc | gdhA | aceE |
| 59 | yjiD | ppc | gdhA | fdhF |
| 60 | yjiD | ppc | gdhA | talB |
| 61 | yjiD | hnr | fdhF | talB |
| 62 | yjiD | hnr | aceE | talB |
| 63 | yjiD | hnr | aceE | fdhF |
| 64 | yjiD | hnr | yjfP | talB |
| 65 | yjiD | hnr | yjfP | fdhF |
| 66 | yjiD | hnr | yjfP | aceE |
| 67 | yjiD | hnr | yjfP | ppc |
| 68 | yjiD | hnr | gdhA | yjfP |
| 69 | yjiD | hnr | gdhA | fdhF |
| 70 | yjiD | hnr | gdhA | aceE |
| 71 | yjiD | hnr | gdhA | talB |
| 72 | yjiD | hnr | ppc | yjfP |
| 73 | yjiD | hnr | ppc | aceE |
| 74 | yjiD | hnr | ppc | gdhA |
| 75 | yjiD | hnr | ppc | fdhF |
| 76 | yjiD | hnr | ppc | talB |
| 77 | aceE | gdhA | yjfP | |
| 78 | ppc | aceE | yjfP | |
| 79 | ppc | aceE | gdhA | |
| 80 | fdhF | ppc | yjfP | |
| 81 | fdhF | ppc | gdhA | |
| 82 | fdhF | ppc | aceE | |
| 83 | talB | fdhF | yjfP | |
| 84 | talB | fdhF | gdhA | |
| 85 | talB | fdhF | aceE | |
| 86 | talB | fdhF | ppc | |
| 87 | gpmB | talB | yjfP | |
| 88 | gpmB | talB | gdhA | |
| 89 | gpmB | talB | aceE | |
| 90 | gpmB | talB | ppc | |
| 91 | gpmB | talB | fdhF | |
| 92 | hnr | gpmB | yjfP | |
| 93 | hnr | gpmB | gdhA | |
| 94 | hnr | gpmB | aceE | |
| 95 | hnr | gpmB | ppc | |
| 96 | hnr | gpmB | fdhF | |
| 97 | hnr | gpmB | talB | |
| 98 | yjiD | gdhA | yjfP | |
| 99 | yjiD | aceE | yjfP | |
| 100 | yjiD | aceE | gdhA | |
| 101 | yjiD | ppc | yjfP | |
| 102 | yjiD | ppc | gdhA | |
| 103 | yjiD | ppc | aceE | |
| 104 | yjiD | fdhF | yjfP | |
| 105 | yjiD | fdhF | gdhA | |
| 106 | yjiD | fdhF | aceE | |
| 107 | yjiD | fdhF | ppc | |
| 108 | yjiD | talB | yjfP | |
| 109 | yjiD | talB | gdhA | |
| 110 | yjiD | talB | aceE | |
| 111 | yjiD | talB | ppc | |
| 112 | yjiD | talB | fdhF | |
| 113 | yjiD | gpmB | yjfP | |
| 114 | yjiD | gpmB | gdhA | |
| 115 | yjiD | gpmB | aceE | |
| 116 | yjiD | gpmB | ppc | |
| 117 | yjiD | gpmB | fdhF | |
| 118 | yjiD | gpmB | talB | |
| 119 | yjiD | hnr | yjfP | |
| 120 | yjiD | hnr | gdhA | |
| 121 | yjiD | hnr | aceE | |
| 122 | yjiD | hnr | ppc | |
| 123 | yjiD | hnr | fdhF | |
| 124 | yjiD | hnr | talB | |
| 125 | yjiD | hnr | gpmB | |
| 126 | yjiD | aceE | | |
| 127 | yjiD | ppc | | |
| 128 | yjiD | fdhF | | |
| 129 | yjiD | talB | | |
| 130 | yjiD | gpmB | | |
| 131 | yjfP | gdhA | | |
| 132 | yjfP | aceE | | |
| 133 | yjfP | ppc | | |
| 134 | yjfP | fdhF | | |
| 135 | yjfP | talB | | |
| 136 | yjfP | gpmB | | |
| 137 | gdhA | aceE | | |
| 138 | gdhA | ppc | | |
| 139 | gdhA | fdhF | | |
| 140 | gdhA | talB | | |
| 141 | gdhA | gpmB | | |
| 142 | aceE | ppc | | |
| 143 | aceE | fdhF | | |
| 144 | aceE | talB | | |
| 145 | aceE | gpmB | | |
| 146 | ppc | fdhF | | |
| 147 | ppc | talB | | |
| 148 | ppc | gpmB | | |
| 149 | fdhF | talB | | |
| 150 | fdhF | gpmB | | |
| 151 | talB | gpmB | | |
| 152 | yjiD | | | |
| 153 | hnr | | | |
| 154 | yjfP | | | |
| 155 | gdhA | | | |
| 156 | aceE | | | |
| 157 | ppc | | | |
| 158 | fdhF | | | |
| 159 | talB | | | |
| 160 | gpmB | | | |

** each row represents an embodiment of what is disrupted or inhibited in a given cell In one embodiment, the cells may further be engineered to over-express one or more dxs, idi, yjiD, rpoS, torC, appY, ydgK, yeiA, yedR, tort, arcB, yggT, purDH, yfjN genes.

In one embodiment, the rpoS gene has a nucleic acid or amino acid sequence that corresponds to that set forth in Genbank Accession Nos: AF275947, AF002209, AF002208, AF002207, AF002206, AF002205, AF002204, AF270497, AJ006210, U66542, AF042351, or a homolgue thereof.

In one embodiment, the torC gene has a nucleic acid or amino acid sequence that corresponds to that set forth in Genbank Accession Nos: X73888, AJ006085, or a homolgue thereof.

In one embodiment, the appY gene has a nucleic acid or amino acid sequence that corresponds to that set forth in Genbank Accession Nos: M24530, BVECM5, AAB40760, BAA15173, AAA23454, or a homolgue thereof.

In one embodiment, the ydgK gene has a nucleic acid or amino acid sequence that corresponds to that set forth in Genbank Accession Nos: YP_090240, P76180, NP_753913, AAU39547, CAB12387, AAN80478, or a homolgue thereof.

In one embodiment, the yeiA gene has a nucleic acid or amino acid sequence that corresponds to that set forth in Genbank Accession Nos: AW457913, AW234827, AW203748, BE211324, or a homolgue thereof.

In one embodiment, the yedR gene has a nucleic acid or amino acid sequence that corresponds to that set forth in Genbank Accession Nos: P76334, NP_754274, AAN80841, or a homolgue thereof.

In one embodiment, the torT gene has a nucleic acid or amino acid sequence that corresponds to that set forth in Genbank Accession Nos: X94231, NP_706917, AAN42624, NP_800184, BAB34572, NP_753055, NP_309176, or a homolgue thereof.

In one embodiment, the arcB gene has a nucleic acid or amino acid sequence that corresponds to that set forth in Genbank Accession Nos: AY529462, AY396288, AY379069, AJ312276, X05637, AY317153, AY282502, M90703, AB095025, AB095024, or a homolgue thereof.

In one embodiment, the yggT gene has a nucleic acid or amino acid sequence that corresponds to that set forth in Genbank Accession Nos: AAG58083, CAG42901, CAC89786, NP_895416, NP_794781, NP_829851, or a homolgue thereof.

In one embodiment, the purDH gene has a nucleic acid or amino acid sequence that corresponds to that set forth in Genbank Accession Nos: AB045609, AB045622, AB045621, AB045620, AB045619, L76417, AF011544, M66160, J05126, or a homolgue thereof.

In one embodiment, the yfjN gene has a nucleic acid or amino acid sequence that corresponds to that set forth in Genbank Accession Nos: AA903291, P52129, or a homolgue thereof.

In another embodiment, each of the strains described in Table I, comprising a single knock out, double knockout or triple knockout, or in another embodiment, cells suppressed or inhibited for expression of the genes as depicted in Table 1, may be further engineered to express a dxs, idi, yjiD, rpoS, torC, appY, ydgK, yeiA, yedR, tort, arcB, yggT, purDH or yfjN gene, or a combination thereof.

For example, any of the strains, except strains 1-20, 30-38, 52-76, 93-130 or 152 of Table 1 may be engineered to over-express dxs, idi, yjiD, rpoS, torC, appY, ydgK, yeiA, yedR, tort, arcB, yggT, purDH or yfjN independently, or in combination, etc. Strains 1-20, 30-38, 52-76, 93-130 or 152 of Table 1 may be engineered to over-express dxs, idi, rpoS, torC, appY, ydgK, yeiA, yedR, tort, arcB, yggT, purDH or yfjN independently, or in combination. It will be appreciated by one skilled in the art that an enormous number of strains may be thus generated, and carotenoid production may be evaluated therefrom via a variety of means, including, in some embodiments of this invention, methods described and exemplified herein.

In one embodiment, the term construct or vector refers to nucleic acid vehicle containing a sequence of interest that has been subcloned within the vector.

To generate the vectors of the present invention, polynucleotides encoding sequences of interest can be ligated into commercially available expression vector systems suitable for transducing/transforming eukaryotic or prokaryotic cells and for directing the expression of recombinant products within the transduced/transformed cells. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter genes.

According to another embodiment, the vectors farther comprise a regulatory element, such as a promoter for regulating expression of the isolated nucleic acid. Such promoters are known to be cis-acting sequence elements required for transcription as they serve to bind DNA dependent RNA polymerase, which transcribes sequences present downstream thereof. The vector may, in another embodiment, comprise an inducible promoter, or one that expresses the sequences of interest constitutively.

A vector according to the present invention, may further include an origin of replication, and may be a shuttle vector, which can propagate both in prokaryotic, and in eukaryotic cells, or the vector may be constructed to facilitate its integration within the genome of an organism of choice. The vector, in other embodiments may be, for example, a plasmid, a bacmid, a phagemid, a cosmid, a phage, a virus or an artificial chromosome.

In another embodiment, the vector contemplated by this invention further comprises an insertion of a heterologous nucleic acid sequence encoding a marker polypeptide. The marker polypeptide may comprise, for example, green fluorescent protein (GFP), DS-Red (red fluorescent protein), secreted alkaline phosphatase (SEAP), beta-galactosidase, luciferase, or any number of other reporter proteins known to one skilled in the art.

Transfer of carotenoid genes into heterologous organisms results in expression, in one embodiment. For example, genes from *Erwina uredovora* and *Haematococcus pluvialis* will function together in *E. coli* (Kajiwara et al. Plant Mol. Biol. 29:343-352 (1995)). *E. herbicola* genes will function in *R. sphaeroides* (Hunter et al. J. Bact. 176:3692-3697 (1994)).

In another embodiment of this invention, the genetically engineered bacterium may belong to the *Acetobacter, Escherichia, Salmonella, Shigella, Erwina, Haematococcus, Rhodobacter, Myxococcus, Corynebacteria, Pseudomonas, Pyrococcus, Ruminococcus, Mycobacteria Bacillus* genu. In another embodiment, the genetically engineered bacterium may be a methylotroph, or in another embodiment, a methanotroph such as *Methylomonas, Methylobacter, Methylocossus, Methylosinus, Methlocyctis, Methylomicrobium, Methanomonas, Methylophilus, Methylobacillus,* and *Methylobacterium*.

The term "methylotroph" refers, in one embodiment, to an organism capable of oxidizing organic compounds that do not contain carbon-carbon bonds. Where the methylotroph is able to oxidize methane ($CH_4$), the methylotroph is also a methanotroph. In one embodiment, the methylotroph uses methanol and/or methane as its primary carbon source.

In one embodiment, the methylotrophs and/or methanotrophs are $C_1$ metabolizing bacteria In one embodiment, the term "$C_1$ metabolizing bacteria" refers to bacteria that have the ability to use a single carbon substrate as their sole source of energy and biomass.

In one embodiment, the term "$C_1$ carbon substrate" refers to any carbon-containing molecule that lacks a carbon-carbon bond. Non-limiting examples are methane, methanol, formaldehyde, formic acid, formate, methylated amines (e.g., mono-, di-, and tri-methyl amine), methylated thiols, and carbon dioxide. In another embodiment, the $C_1$ carbon substrates is selected from the group consisting of methanol and/or methane.

The term "methanotroph" or "methanotrophic bacteria" refers, in another embodiment, to a prokaryote capable of utilizing methane as its primary source of carbon and energy. Complete oxidation of methane to carbon dioxide occurs by aerobic degradation pathways. Typical examples of methanotrophs useful in the present invention include (but are not limited to) the genera *Methylomonas, Methylobacter, Methylococcus,* and *Methylosinus*. In one embodiment, the methanotrophic bacteria uses methane and/or methanol as its primary carbon source.

In one embodiment, the term "high growth methanotrophic bacterial strain" refers to a bacterium capable of growth with methane and/or methanol as the sole carbon and energy source and which possesses a functional Embden-Meyerhof carbon flux pathway, resulting in a high rate of growth and yield of cell mass per gram of $C_1$ substrate metabolized (U.S. Pat. No. 6,689,601; hereby incorporated by reference). The specific "high growth methanotrophic bacterial strain" described herein is referred to as "*Methylomonas* 16a", "16a" or "*Methylomonas* sp. 16a", which terms are used interchangeably and which refer to the *Methylomonas* strain used in the present invention.

Techniques for the transformation of $C_1$ metabolizing bacteria may parallel the general methodology that is utilized for other bacteria, which is well known to those of skill in the art.

Electroporation has been used successfully for the transformation of: *Methylobacterium extorquens* AM1 (Toyama, H., et al., *FEMS Microbiol. Lett.*, 166:1-7 (1998)), *Methylophilus methylotrophus* AS1 (Kim, C. S., and T. K. Wood, *Appl. Microbiol Biotechnol.*, 48: 105-108 (1997)), and *Methylobacillus sp.* strain 12S (Yoshida, T., et al., *Biotechnol. Lett.*, 23: 787-791 (2001)).

Bacterial conjugation, relying on the direct contact of donor and recipient cells, may also be used for the transfer of genes into C1 metabolizing bacteria. Bacterial conjugation processes may involve mixing together "donor" and "recipient" cells in close contact with one another. Conjugation occurs by formation of cytoplasmic connections between donor and recipient bacteria, with direct transfer of newly synthesized donor DNA into the recipient cells. The recipient in a conjugation accepts DNA through horizontal transfer from a donor bacterium. The donor in conjugative transfer may have a conjugative plasmid, conjugative transposon, or mobilizable plasmid.

In some cases, only a donor and recipient are required for conjugation. This occurs when the plasmid to be transferred is a self-transmissible plasmid that is both conjugative and mobilizable (i.e., carrying both tra genes and genes encoding the Mob proteins). In general, the process involves the following steps: 1.) Double-strand plasmid DNA is nicked at a specific site in oriT; 2.) A single-strand DNA is released to the recipient through a pore or pilus structure; 3.) A DNA relaxase enzyme cleaves the double-strand DNA at oriT and binds to a released 5' end (forming a relaxosome as the intermediate structure); and 4.) Subsequently, a complex of auxiliary proteins assemble at oriT to facilitate the process of DNA transfer.

A "triparental" conjugation may also be required for transfer of the donor plasmid to the recipient. In this type of conjugation, donor cells, recipient cells, and a "helper" plasmid participate. The donor cells carry a mobilizable plasmid or conjugative transposon. Mobilizable vectors contain an oriT, a gene encoding a nickase, and have genes encoding the Mob proteins; however, the Mob proteins alone are not sufficient to achieve the transfer of the genome. Thus, mobilizable plasmids are not able to promote their own transfer unless an appropriate conjugation system is provided by a helper plasmid (located within the donor or within a "helper" cell). The conjugative plasmid is needed for the formation of the mating pair and DNA transfer, since the plasmid encodes proteins for transfer (Tra) that are involved in the formation of the pore or pilus.

Examples of successful conjugations involving $C_1$ metabolizing bacteria include the work of: Stolyar et al. (*Mikrobiologiya*, 64(5): 686-691 (1995)); Motoyama, H. et al. (*Appl. Micro. Biotech.*, 42(1): 67-72 (1994)); Lloyd, J. S. et al. (*Archives of Microbiology*), 171(6): 364-370 (1999)); Odom, J. M. et al. (U.S. Ser. No. 09/941,947 corresponding to WO 02/18617); U.S. Ser. No. 10/997,308; and U.S. Ser. No. 10/997,844; hereby incorporated by reference.

In another embodiment, the genetically engineered bacterium may further comprise an isopentenyl pyrophosphate isomerase [Idi], a farnesyl pyrophosphate synthetase [IspA], a geranyltranstransferase, an octoprenyl pyrophosphate synthase [IspB], a geranylgeranyl pyrophosphate (GGPP) synthase [CcrtE], a phytoene synthase [CrtB], a phytoene desaturase [CrtI], a lycopene cyclase [CrtY], a β-carotene hydroxylase [CrtZ], a zeaxanthin glucosyl transferase [CrtX], a β-carotene ketolase [CrtO], or a combination thereof.

In an embodiment of the invention, the bacteria may be further engineered to generate variants in the regulatory and/or structural elements of genes in the carotenoid synthesis pathway, allowing increased expression in heterologous hosts. For example, mutation of regulatory genes can cause constitutive expression of carotenoid synthesis in actinomycetes, where carotenoid photoinducibility is otherwise unstable and lost at a relatively high frequency in some species (Kato et al. Mol Gen. Genet. 247:387-390 (1995)).

It is to be understood that by reference to carotenoids in the present invention, any carotenoid compound thus produced, including but not limited to myxobacton, spheroidene, spheroidenone, lutein, violaxanthin, 4-ketorulene, myxoxanthrophyll, echinenone, canthaxanthin, phytoene, α-, β-, γ-, δ- or ε-carotene, lycopene, β-cryptoxanthin monoglucoside or neoxanthin is to be considered as part of this invention.

In another embodiment, the carotenoids may include antheraxanthin, adonixanthin, astaxanthin, canthaxanthin, capsorubrin, β-cryptoxanthin echinenone, zeta-carotene, alpha-cryptoxanthin, diatoxanthin, 7,8-didehydroastaxanthin, fucoxanthin, fucoxanthinol, isorenieratene, lactucaxanthin, lutein, lycopene, neoxanthin, neurosporene, hydroxyneurosporene, peridinin, phytoene, rhodopin, rhodopin glucoside, siphonaxanthin, spheroidene, spheroidenone, spirilloxanthin, uriolide, uriolide acetate, violaxanthin, zeaxanthin-β-digducoside, and zeaxanthin.

In another embodiment, the genetically engineered bacteria of this invention are responsible for enhanced carotenoid production of between 3 and 95%, as compared to wild-type strains. The knockout constructs, as generated herein (FIG. 5) resulted in enhanced lycopene production ranging from between a 3 to 100% increase over wild-type production. Similarly, some of the knockout constructs further expressing, for example, yjiD had similar yields, as described further, hereinbelow.

In another embodiment, this invention provides a carotenoid-producing bacterium, comprising one or more inhibitors of yjiD, hnr or yjfP gene activity, or a combination thereof, wherein use of said one or more inhibitors results in enhanced carotenoid production in said bacterium, as compared to wildtype. In another embodiment, the carotenoid-producing bacterium may farther comprise one or more inhibitors of gdhA, gpmB aceE, ppc, talB or fdhF gene activity, or a combination thereof. In another embodiment, the carotenoid-producing bacterium may be further engineered to express a dxs, idi, yjiD, rpoS, torC, appY, ydgK, yeiA, yedR, tort, arcB, yggT, purDH or yfjN gene, or a combination thereof.

According to this aspect of the invention and in one embodiment, the inhibitor comprises a nucleic acid. A nucleic acid molecule of this invention, comprises RNA or DNA that is single- or double-stranded. In another embodiment, the nucleic acid may contain synthetic, non-natural or altered nucleotide bases. A nucleic acid of this invention may comprise a fragment in the form of a polymer of DNA, or may be comprised of one or more segments of cDNA, genomic DNA or synthetic DNA.

In another embodiment, nucleic acids used in this invention comprise analogs of either RNA or DNA made from nucleotide analogs, and, as applicable to the embodiment being described, single (sense or antisense) and double-stranded polynucleotides. This term includes oligonucleotides composed of naturally occurring nucleobases, sugars and covalent internucleoside (backbone) linkages as well as oligonucleotides having non-naturally-occurring portions, which function similarly. Such modified or substituted oligonucleotides are often preferred over native forms because of desirable properties such as, for example, enhanced cellular uptake, enhanced affinity for nucleic acid target, increased stability in the presence of nucleases and/or efficient gene silencing.

The nucleic acids used in this invention can be produced by any synthetic or recombinant process such as is well known in the art. Nucleic acids can further be modified to alter biophysical or biological properties by means of techniques known in the art. For example, the nucleic acid can be modified to increase its stability against nucleases (e.g., "end-capping"), or to modify its lipophilicity, solubility, or binding affinity to complementary sequences.

DNA according to the invention can also be chemically synthesized by methods known in the art. For example, the DNA can be synthesized chemically from the four nucleotides in whole or in part by methods known in the art. Such methods include those described in Caruthers (1985). DNA can also be synthesized by preparing overlapping double-stranded oligonucleotides, filling in the gaps, and ligating the ends together (see, generally, Sambrook et al. (1989) and Glover et al. (1995)). DNA expressing functional homologues of the protein can be prepared from wild-type DNA by site-directed mutagenesis (see, for example, Zoller et al. (1982); Zoller (1983); and Zoller (1984); McPherson (1991)). The DNA obtained can be amplified by methods known in the art. One suitable method is the polymerase chain reaction (PCR) method described in Saiki et al. (1988), Mullis et al., U.S. Pat. No. 4,683,195, and Sambrook et al. (1989).

In one embodiment, the inhibitor inhibits yjiD, hnr and/or yjfP expression, activity or function, and in another embodiment, may further inhibit gdhA, gpmB, aceE, ppc, talB and/or fdhF expression, activity or function. In one embodiment, several inhibitors may be used concurrently, or in another embodiment, sequentially. In another embodiment, the inhibitor may be added at different times during the growth cycle of the recombinant cell. In one embodiment, the inhibitor is a nucleic acid that is antisense in orientation to a sequence encoding for the indicated genes.

According to this aspect of the invention, in one embodiment, inhibition of expression, activity or function is effected via the use of antisense oligonucleotides, which are chimeric molecules, containing two or more chemically distinct regions, each made up of at least one nucleotide. These chimeric oligonucleotides contain, in one embodiment, at least one region wherein the oligonucleotide is modified so as to confer upon the oligonucleotide, in one embodiment, an increased resistance to nuclease degradation, or, in another embodiment, increased cellular uptake, and/or, in another embodiment, an increased binding affinity for the target polynucleotide. An additional region of the oligonucleotide may serve as a substrate for enzymes capable of cleaving RNA:DNA or RNA:RNA hybrids, which according to this aspect of the invention, serves as a means of gene silencing via degradation of specific sequences. Cleavage of the RNA target can be detected, in one embodiment by gel electrophoresis or, in another embodiment via nucleic acid hybridization techniques known in the art.

The chimeric antisense oligonucleotides may, in one embodiment, be formed as composite stuctures of two or more oligonucleotides and/or modified oligonucleotides, as is well described in the art (see, for example, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922), and can, in another embodiment, comprise a ribozyme sequence.

Inhibition of yjiD, hnr and/or yjfP expression, activity or function, and in another embodiment, further inhibition of gdhA, gpmB, aceE, ppc, talB and/or fdhF expression, activity or function is effected, in another embodiment, via the use of small interfering RNAs, which provides sequence-specific inhibition of gene expression. Administration of double stranded/duplex RNA (dsRNA) corresponding to a single gene in an organism can silence expression of the specific gene by rapid degradation of the mRNA in affected cells. This process is referred to as gene silencing, with the dsRNA functioning as a specific RNA inhibitor (RNAi). RNAi may be derived from natural sources, such as in endogenous virus and transposon activity, or it can be artificially introduced into cells (Elbashir S M, et al (2001). Nature 411:494-498) via microinjection (Fire et al. (1998) Nature 391: 806-11), or by transformation with gene constructs generating complementary RNAs or fold-back RNA, or by other vectors (Waterhouse, P. M., et al. (1998). Proc. Natl. Acad. Sci. USA 95, 13959-13964 and Wang, Z., et al. (2000). J. Biol. Chem. 275, 40174-40179. The RNAi mediating mRNA degradation, in one embodiment, comprises duplex or double-stranded RNA, or, in other embodiments, include single-stranded RNA, isolated RNA (partially purified RNA, essentially pure RNA, synthetic RNA, recombinantly produced RNA), as well as altered RNA that differs from naturally occurring RNA by the addition, deletion and/or alteration of one or more nucleotides.

In one embodiment, inhibition as described may be effected via the use of a plasmid, which facilitates expression of the nucleic acid inhibitor. In one embodiment, the plasmid will comprise a regulatory sequence, which regulates expression of the nucleic acid inhibitor. In one embodiment, these regulatory sequences will comprise a promoter, which in one embodiment, provides for constitutive or, in another embodiment inducible, expression of the nucleic acid inhibitor. In another embodiment, the promoter may provide a means of high and low levels of expression of the nucleic acid inhibitor. In another embodiment, expression of the nucleic acid inhibitor may be regulated to provide for gene inactivation at a specific point in the growth stage of the cell.

In another embodiment, the inhibitor of yjiD, hnr and/or yjfP expression, activity or function, or in another embodiment, the inhibitor of gdhA, gpmB, aceE, ppc, talB and/or fdhF expression, activity or function comprises a chemical inhibitor or a polypeptide preventing protein function. The inhibitor may comprise an antibody or antibody fragment, the design of which is via methodology well known to those skilled in the art.

In another embodiment, the inhibitor is designed to physically block the transcriptional machinery of the cell, preventing yjiD, hnr and/or yjfP or in another embodiment, gdhA, gpmB, aceE, ppc, talB and/or fdhF expression. The design of such molecules can be accomplished by methods well known in the art.

In another embodiment, inhibitors of the yjiD, hnr and/or yjfP or in another embodiment, gdhA, gpmB, aceE, ppc, talB and/or fdhF gene products may be designed The structure of the yjiD, hnr yjfP or in another embodiment, gdhA, gpmB, aceE, ppc, talB and/or fdhF genes may be ascertained, by for example, X-Ray crystallographic data or NMR, whereupon binding sites can be ascertained, which can be filled with a close packed array of generic atoms. A Monte Carlo procedure (D. K. Gehlhaar, et al. "De Novo Design of Enzyme Inhibitors by Monte Carlo Ligand Generation" J. Med. Chem. 1995, 38, 466-472) may be used, in another embodiment, to randomly move, rotate, exchange atom types and/or bond types, and the resulting chemical moieties, representing inhibitors for yjiD, hnr and/or yjfP or in another embodiment, gdhA, gpmB, aceE, ppc, talB and/or fdhF gene products, designed can be tested for their ability to inhibit the yjiD, hnr and/or yjfP or in another embodiment, gdhA, gpmB, aceE, ppc, talB and/or fdhF gene product interaction with their respective substrates, for example, or other methods as will be known to one skilled in the art.

It is to be understood that any inhibitor designed to regulate yjiD, hnr and/or yjfP or in another embodiment, gdhA, gpmB, aceE, ppc, talB and/or fdhF expression, function or activity, for purposes of enhancing carotenoid production is to be considered part of the present invention. It is also to be understood that inhibitors from one or more classes, as described above, for example, a nucleic acid and chemical, may be used in conjunction to effect the methods of this invention, and comprise the cells of this invention.

In another embodiment, the one or more inhibitors suppress or abrogate gdhA, aceE and fdhF gene expression or function. In another embodiment, the one or more inhibitors suppress or abrogate gdhA and yjfP gene expression or function. In another embodiment, the one or more inhibitors suppress or abrogate gdhA, aceE and yjfP gene expression or function. In another embodiment, the one or more inhibitors suppress or abrogate gdhA, aceE, fdhF and yjfP gene expression or function. In another embodiment, the one or more inhibitors suppress or abrogate gpmB and yjiD gene expression or function. In another embodiment, the one or more inhibitors suppress or abrogate gdhA, aceE, and yjiD gene expression or function. In another embodiment, the one or more inhibitors suppress or abrogate gdhA, gpmB and yjiD gene expression or function. In another embodiment, the one or more inhibitors suppress or abrogate gdhA, aceE, hnr and yjfP gene expression or function. In another embodiment, the one or more inhibitors suppress or abrogate gdhA, aceE, hnr, yjfP and yjiD gene expression or function In another embodiment, the one or more inhibitors suppress or abrogate gdhA, gpmB and yjfP gene expression or function.

In one embodiment, the presence of said one or more inhibitors in said bacterium results in enhanced carotenoid production of between 3 and 100%. It is to be understood that any bacterium which can produce carotenoids, and wherein inhibition of gdhA, aceE and/or fdhF gene expression, function and/or activity may be accomplished, or in another embodiment, further inhibiting gdhA, gpmB, aceE, ppc, talB and/or fdhF gene expression, function and/or activity may be accomplished, wherein utilization of such an inhibitor or inhibitors results in enhanced carotenoid production, is to be considered as part of this invention.

In one embodiment, a cell or bacterium of this invention may be engineered to over-express dxs, idi, yjiD, rpoS, torC, appY, ydgK, yeiA, yedR, tort, arcB, yggT, purDH or yfjN independently, or in combination. In one embodiment, overexpression may be effected via the use of any vector, such as, in one embodiment, a plasmid, virus, or isolated nucleic acid, which facilitates expression of the desired gene or, in another embodiment, genes. In one embodiment, the vector will comprise a regulatory sequence, which regulates expression of the gene. In one embodiment, these regulatory sequences will comprise a promoter, which in one embodiment, provides for constitutive or, in another embodiment inducible, expression of the gene or genes. In another embodiment, the promoter may provide a means of high and low levels of expression of the nucleic acid inhibitor. In another embodiment, expression of the gene may be regulated to provide for gene expression at a specific point in the growth stage of the cell, or in another embodiment, availability of nutrients to the cell, or in another embodiment, environmental conditions to which the cell is exposed.

In one embodiment, the term "nutrients" refers to carbon source, or in another embodiment, nitrogen source, etc., as will be appreciated by one skilled in the art.

In one embodiment, the term "environmental conditions" refers to temperature, or in another embodiment, $CO_2$ or oxygen content, or in another embodiment, atmospheric pressure, or others, as will be appreciated by one skilled in the art.

Incorporation of desired nucleic acid sequences within cells can be accomplished through a number of methods well known in the art. Nucleic acid constructs can be utilized to stably or transiently transfect or transduce the cells.

There are a number of techniques known in the art for introducing vectors it into cells of the present invention, such as, but not limited to: direct DNA uptake techniques, and virus, plasmid, linear DNA or liposome mediated transduction, receptor-mediated uptake and magnetoporation methods employing calcium-phosphate mediated and DEAE-dextran mediated methods of introduction, electroporation or liposome-mediated transfection, (for further detail see, for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals). Bombardment with nucleic acid coated particles is also envisaged. It is to be understood that any of these methods may be utilized for introduction of the desired sequences into cells, for production of the cells of this invention, and for effecting the methods of this invention.

The cells and methods of this invention may be used, in other embodiments, for carotenoid production.

Methods for the detection of the carotenoids produced in the cells or via the methods of this invention are well known in the art, and may comprise, in one embodiment, HPLC, Mass Spectroscopy, ELISA, RIA or Western blot analysis [see "Cell Biology: A Laboratory Handbook", Volumes I-III Cellis, J. E., ed. (1994); "Current Protocols in Immunology" Volumes I-III Coligan J. E., ed. (1994); Stites et al. (eds)].

In another embodiment, this invention provides a method for production of carotenoids, comprising genetically disrupting a yjiD, hnr or yjfP gene, or a combination thereof in a cell comprising genes involved in the carotenoid biosynthetic pathway and isolating carotenoids from the cell, thereby producing carotenoids. In one embodiment, according to this aspect of the invention, the method for production of carotenoids, may further comprise genetically disrupting a gdhA, gpmB aceE, ppc, talB or fdhF gene, or a combination thereof in a cell comprising genes involved in the carotenoid biosynthetic pathway.

In one embodiment, the genes gdhA, aceE and fdhF are disrupted. In another embodiment, the genes gdhA and yjfP are disrupted. In another embodiment, genes gdhA, aceE and yjfP are disrupted. In another embodiment, the genes gdhA, aceE, fdhF and yjfP are disrupted. In another embodiment, the genes gpmB and yjiD are disrupted. In another embodiment, the genes gdhA, aceE, and yjiD are disrupted. In another embodiment, the genes gdhA, gpmB and yjiD are disrupted. In another embodiment, the genes gdhA, aceE, hnr and yjfP are disrupted. In another embodiment, the genes gdhA, aceE, hnr, yjfP and yjiD are disrupted. In another embodiment, the genes gdhA, gpmB and yjfP are disrupted.

Similarly, in another embodiment, according to this aspect of the invention the cells may be further engineered to over-express dxs, idi, yjiD, rpoS, torC, appY, ydgK, yeiA, yedR, tort, arcB, yggT, purDH or yfjN independently, or in combination.

It is to be understood that any embodiment described herein, for the genetic engineering of bacterium resulting in enhanced carotenoid production is to be considered applicable to the methods of this invention. In one embodiment, the genetically engineered bacteria will comprise genes involved in the carotenoid biosynthetic pathway such, as, for example, isoprenyl pyrophosphate isomerase, farnesyl pyrophosphate synthetase [IspA], geranyltranstransferase, Octoprenyl pyrophosphate synthase [IspB], geranylgeranyl pyrophosphate (GGPP) synthase [CrtE], phytoene synthase [CrtB], phytoene desaturase [CrtI], lycopene cyclase[CrtY], b-carotene hydroxylase [CrtZ], zeaxanthin glucosyl transferase [CrtX], b-carotene ketolase [CrtO], or a combination thereof.

In another embodiment, the methods of this invention result in an increased production of carotenoids of between 3 and 100%, as compared to wildtype cells. In one embodiment, the increase in production will vary as a function of time and culture conditions.

In another embodiment, this invention provides a method for enhanced production of carotenoids, comprising contacting a cell comprising genes involved in the carotenoid biosynthetic pathway with one or more inhibitors of yjiD, hnr or yjfP gene expression or function, or a combination thereof and isolating carotenoids from the cell, thereby enhancing production of carotenoids. According to this aspect of the invention, and in another embodiment, the method for enhanced production of carotenoids, further comprises contacting the cell with one or more inhibitors of gdhA, gpmB aceE, ppc, talB or fdhF gene expression or function, or a combination thereof. In one embodiment, the carotenoids comprise astaxanthin, canthaxanthin, beta-carotene, lycopene, phytoene or zeaxanthin.

In one embodiment, the cell is contacted with one or more inhibitors of gdhA and gpmB expression or function. In another embodiment, the cell is contacted with one or more inhibitors of gdhA, aceE and fdhF gene expression or function. In another embodiment the cell is contacted with one or more inhibitors of gdhA and yjfP gene expression or function. In another embodiment, the cell is contacted with one or more inhibitors of gdhA, aceE and yjfP gene expression or function. In another embodiment, the cell is contacted with one or more inhibitors of gdhA, aceE, fdhF and yjfP gene expression or function. In another embodiment, the cell is contacted with one or more inhibitors of gpmB and yjiD gene expression or function. In another embodiment, the cell is contacted with one or more inhibitors of gdhA, aceE, and yjiD gene expression or function. In another embodiment, the cell is contacted with one or more inhibitors of gdhA, gpmB and yjiD gene expression or function. In another embodiment, the cell is contacted with one or more inhibitors of gdhA, aceE, hnr and yjfP gene expression or function. In another embodiment, the cell is contacted with one or more inhibitors of gdhA, aceE, hnr, yifP and yjiD gene expression or function. In another embodiment, the cell is contacted with one or more inhibitors of gdhA, gpmB and yjfP gene expression or function.

In one embodiment, the one or more inhibitors comprises a nucleic acid, and may comprise any of the embodiments listed herein for nucleic acids, and their application in inhibiting or abrogating yjiD, hnr and/or yjfP gene expression, function or activity, or in another embodiment, further inhibiting gdhA, gpmB aceE, ppc, talB and/or fdhF gene expression, function or activity. In one embodiment, the methods inhibiting or abrogating yjiD, hnr and/or yjfP gene expression, function or activity, or in another embodiment, further inhibiting gdhA, gpmB aceE, ppc, talB and/or fdhF gene expression, function or activity, results in an increased carotenoid production of between 3 and 100%.

In another embodiment, according to this aspect of the invention, a cell or bacterium of this invention, inhibited as described, may also be engineered to over-express dxs, idi, yjiD, rpoS, torC, appY, ydgK, yeiA, yedR, tort arcB, yggT, purDH or yfjN independently, or in combination.

In one embodiment, substrate supplied to the bacteria or cells of this invention for production of carotenoids may vary, and may be in the range of, in one embodiment, between 0.2 g to 200 grams, or, in another embodiment, 3 to 100 grams per liter of medium. In another embodiment, supplemented amino acids may vary, and may be in the range of 0.05 g to 10 grams per liter of medium. The pH of the growth medium may range, in one embodiment from 2 to 12, or in another embodiment, from 6 to 9, or in another embodiment, befitting that required by the bacteria being cultured. Similarly, and in another embodiment, culture conditions in terms of temperature may be varied, from, for example, 15 to 80° C., or in another embodiment, from 20 to 35° C., as required.

In one embodiment, the carotenoids produced via the cells/bacteria and methods of this invention may be isolated and purified from the cultures. In one embodiment, cells/bacteria are separated from the culture by a conventional means such as centrification or filtration, and the cells/bacteria are subjected to an extraction with a solvent.

In one embodiment, the carotenoids are dissolved in a supernatant or filtrate, and may be recovered from them. As a solvent for the extraction, any substance in which the present compound is soluble can be used. For example, and in other embodiments herein, organic solvents such as acetone, chloroform, dichloromethane, hexane, cyclohexane, methanol, ethanol, isopropanol, benzene, carbon disulfide, diethyl ether etc. may be used. The purification may be carried out by conventional procedures such as absorption, elution, dissolving and the lice, alone or preferably in combination.

In another embodiment, mixtures of carotenoids are produced, such as for example, simultaneous production of astaxanthin, adonixanthin, β-carotene, echinenone, canthaxanthin and/or zeaxanthin and are present in a culture product. Accordingly, in an embodiment of the present invention, any one of the above-mentioned carotenoids can be singly obtained by the above-mentioned procedure. Alternatively, a mixture of the carotenoids also can be obtained. In this way, the process for carotenoid production of the present invention includes a process for production of an individual carotenoid and a process for production of a mixture of the carotenoids.

Astaxanthin and adonixanthin can be separated from each other by methods well known to one skilled in the art for mutual separation of carotenoids, such as adsorption/elusion column chromatography, differential extraction, counter current extraction or differential crystallization.

The identification of genes which when inhibited resulted in high-yield carotenoid biosynthesis was accomplished herein, in some embodiments, via transposon mutagenesis. According to this aspect of the invention, a transposon mutagenized library was generated using the pJA1 vector (Badarinarayana, V., et al., Selection analyses of insertional mutants using subgenic-resolution arrays. Nat. Biotech., 2001. 19(11): p. 1060-1065), and screened on minimal media plates, and several candidate genes were identified. Combinatorial strains, may be derived via this method, for example, the seven gene combinations of single, double, and triple combinatorial target mutations of the three genes exemplified herein.

In another embodiment, the mutagenized library may be constructed using other transposons. In one embodiment, the mariner transposon may be used. Mariner transposition occurs efficiently in vitro, does not require cellular cofactors and shows very little insertion site specificity, requiring only the dinucleotide TA in the target sequence (and even this minor site specificity can be easily altered using different in vitro reaction conditions). In another embodiment, the Tn7 transposon may be used.

Transposons occur naturally as DNA sequences coding for an enzyme, transposase, which recognizes and cuts the DNA at sites flanking the gene for the transposase. The recognition sites, or binding sites for the transposase, are referred to as inverted repeat sequence. As such, transposable elements, when activated, produce an enzyme, which promotes the excision of itself from one location in DNA and the insertion of the excised DNA at another site. In some embodiments, the transposon selected will exhibit site-specific insertion at so-called "hot spots."

In another embodiment, the transposon may be Tn551, Minos, Hermes or piggyback. In another embodiment, the transposon may be AT-2 (tyl based transposon, Perkin Elmer; Devine et al. (1997) Genome Res. 7:551-563), GPS-1 (New England Biolabs), GPS-2 (New England Biolabs), EZ::tn (Tn5 based transposon, Epicenter Technologies), SIF (Tn7 based transposon, Biery et al. (2000) Nucl Acid Res 28:1067-1077), or Mu (Finnzymes, Haapa et al. (1999) Nucl Acid Res 13:2777-2784). It is to be understood that any transposon may be used in the methods of this invention.

The transposons will be employed, in one embodiment, with their natural cognate transposases, or in another embodiment, with the use of modified and/or improved transposases.

In another embodiment, the transposon may comprise a nucleic acid sequence encoding a heterologous polypeptide. This sequence may be integrated, together with the transposon, into the genome of the cell on transposon integration. In one embodiment, the heterologous polypeptide may be excised, together with the transposon, when the latter excises on remobilisation. In one embodiment, the heterologous polypeptide is a detectable marker, such as, for example, the green fluorescent protein (GFP), or mutants, homologues thereof.

GFPs have been isolated from the Pacific Northwest jellyfish, *Aequorea victoria*, from the sea pansy, *Renilla reniformis*, and from *Phialidium gregarium*. (Ward et al., 1982, Photochem. Photobiol., 35: 803-808; Levine et al., 1982, Comp. Biochem. Physiol., 72B: 77-85). See also Matz, et al., 1999, ibid for fluorescent proteins isolated recently from *Anthoza* species (accession nos. AF168419, AF168420, AF168421, AF168422, AF168423 and AF168424), each of which may be incorporated in the methods of this invention.

A variety of *Aequorea*-related GFPs having useful excitation and emission spectra have been engineered by modifying the amino acid sequence of a naturally occurring GFP from *Aequorea victoria* (Prasher et al., 1992, Gene, 111: 229-233; Heim et al., 1994, Proc. Natl. Acad. Sci. U.S.A., 91: 12501-12504; PCT/US95/14692).

In another embodiment, in vitro transposition may be conducted upon genomic DNA cloned into a vector, for example a cosmid, phage, plasmid, YAC (yeast artificial chromosome), or BAC (bacterial artificial chromosome) vector. Similar high-density mutagenesis can be performed in non-naturally competent organisms using genomic DNA cloned into an allelic replacement vector (see for example, U.S. Pat. No. 6,207,384).

In one embodiment, chromosomal DNA from the cell of interest is isolated and mutagenized with the Himar1 transposase and, in another embodiment, an artificial mimitransposon encoding a marker gene, such as, for example, the gene for either kanamycin or chloramphenicol resistance.

Insertion of the transposon produces a short single-stranded gap on either end of the insertion site. In one embodiment, bacterial strains, which are known to take up single stranded DNA are utilized, and according to this aspect of the invention, these gaps may require repair (using a DNA polymerase and a DNA ligase) to produce the flanking DNA sequence required for recombination into the chromosome.

Mutagenized DNA is transformed into bacteria, in one embodiment, or other cells of interest, in another embodiment, by methods well known and described in the art (see for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals). Cells, which acquire transposon insertions by homologous recombination, are selected, for example via plating on an appropriate antibiotic-containing medium.

In one embodiment, southern blot analysis of digested DNA from individual transposon mutants to verify transposon insertion. In another embodiment, sequence analysis, PCR and/or hybridization may be utilized to determine transposon insertion.

Screening of the mutagenized library obtained as exemplified herein on minimal media plates identified three genes, which showed an increase in the production of lycopene when these mutations were introduced into the cell, which comprise embodiments of this invention. It is to be understood, that other genes may be identified via the methods of this invention, via the combination of data obtained from the flux-balance analysis as described further hereinbelow, and that obtained via any means of transposon mutagenesis, which, when combined result in a strain which produces a higher yield of carotenoid. The method of identification, as well as strains obtained thereby, are to be considered as part of this invention.

The identification of systematic targets, comprising genes which when inhibited resulted in high-yield carotenoid biosynthesis was accomplished herein via a modified flux-balance analysis (FBA). According to this aspect of the invention, the modified FBA allowed for a reduction in the search space requiring experimental validation.

In one embodiment, the invention provides methods for utilizing genome annotation data to construct a stoichiometric matrix representing metabolic reactions that occur within an organism. Using these methods, the properties of this matrix can be studied under conditions simulating genetic deletions in order to predict the affect of a particular gene on a given product yield, or in another embodiment, viability, or, in another embodiment, a parameter of interest.

It should be noted that the methods described herein can be implemented on any conventional host computer system, such as those based on Intel® microprocessors and running Microsoft Windows operating systems. Other systems, such as those using the UNIX or LINUX operating system and based on IBM®, DEC® or Motorola® microprocessors are also contemplated. The methods described herein can also be implemented to run on client-server systems and wide-area networks, such as the Internet.

Software to implement the system can be written in any well-known computer language, such as Java, C, C++, Visual Basic, FORTRAN or COBOL and compiled using any well-known compatible compiler.

The software of the invention normally runs from instructions stored in a memory on the host computer system. Such a memory can be a hard disk, Random Access Memory, Read Only Memory and Flash Memory. Other types of memories are also contemplated to function within the scope of the invention.

For each gene involved in ascertaining a parameter of interest, for example, for a metabolic pathway, all information is gathered and compiled in a matrix. In one embodiment, the parameter is a biosynthetic product yield, and the substrates and products, as well as the stoichiometry of any and all reactions performed by the gene product of each gene as determined by reference to the biochemical literature, including information regarding the irreversible or reversible nature of the reactions are compiled. The stoichiometry of each reaction providing the molecular ratios in which reactants are converted into products are compiled as well. Transport of metabolites into, or out of, the cell is compiled as well.

In one embodiment, the reactions and their stoichiometry are represented in a matrix format, referred to as a stoichiometric matrix. Each column in the matrix corresponds to a given reaction or flux, and each row corresponds to the different metabolites involved in the given reaction/flux. Reversible reactions may either be represented as one reaction that operates in both the forward and reverse direction or be decomposed into one forward reaction and one backward reaction in which case all fluxes can only take on positive values. Thus, a given position in the matrix describes the stoichiometric participation of a metabolite (listed in the given row) in a particular flux of interest (listed in the given column). Together all of the columns of the genome specific stoichiometric matrix represent all of the chemical conversions and cellular transport processes that are determined to be present in the organism. This includes all internal fluxes and so called exchange fluxes operating within the metabolic network. The resulting genome specific stoichiometric matrix is a fundamental representation of a genomically and biochemically defined genotype.

After the genome specific stoichiometric matrix is defined, the metabolic demands placed on the organism are calculated. The metabolic demands can be readily determined from the dry weight composition of the cell. In the case of well-studied organisms such as *Escherichia coli* and *Bacillus subtilis*, the dry weight composition is available in the published literature However, in some cases it will be necessary to experimentally determine the dry weight composition of the cell for the organism in question. This can be accomplished with varying degrees of accuracy. The first attempt would measure the RNA, DNA, protein, and lipid fractions of the cell. A more detailed analysis would also provide the specific fraction of nucleotides, amino acids, etc.

Uptake rates and maintenance requirements for the organism are also compiled. Microbiological experiments can be carried out to determine the uptake rates for many of the metabolites that are transported into the cell. The uptake rate is determined by measuring the depletion of the substrate from the growth media. The measurement of the biomass at each point is also required, in order to determine the uptake rate per unit biomass. The maintenance requirements can be determined from a chemostat experiment. The glucose uptake rate is plotted versus the growth rate, and the y-intercept is interpreted as the non-growth associated maintenance requirements. The growth associated maintenance requirements are determined by fitting the model results to the experimentally determined points in the growth rate versus glucose uptake rate plot.

Next, information regarding the metabolic demands and uptake rates are combined with the genome specific stoichiometric matrix, which together fully define the metabolic system using flux balance analysis (FBA).

The time constants characterizing metabolic transients and/or metabolic reactions are typically very rapid, on the order of milli-seconds to seconds, compared to the time constants of cell growth on the order of hours to days. Thus, the transient mass balances can be simplified to only consider steady state behavior. Eliminating the time derivatives obtained from dynamic mass balances around every metabolite in the metabolic system, yields the system of linear equations represented in matrix notation, $S \cdot v = 0$, where S refers to the stoichiometric matrix of the system, and v is the flux vector. This equation simply states that over long times, the formation fluxes of a metabolite must be balanced by the degradation fluxes. Otherwise, significant amounts of the metabolite will accumulate inside the metabolic network. According to this aspect of the invention, S represents the genome specific stoichiometric matrix.

To determine the metabolic capabilities of a defined metabolic genotype the equation is solved, in one embodiment, for the metabolic fluxes and the internal metabolic reactions, v, while imposing constraints on the activity of these fluxes. In one embodiment, the number of metabolic fluxes is greater than the number of mass balances (i.e., m>n) resulting in a plurality of feasible flux distributions that satisfy the equation, and any constraints placed on the fluxes of the system.

The solution to the equation can be formulated, in one embodiment, as a linear programming problem, in which the flux distribution that minimizes a particular objective is found. Mathematically, this optimization can be stated as minimize Z, where $Z = \Sigma c_i \cdot v_i = <c \cdot v>$, where Z is the objective which is represented as a linear combination of metabolic fluxes $v_i$. The optimization can also be stated as the equivalent maximization problem; i.e. by changing the sign on Z.

In one embodiment, assigning Z enables the formulation of a number of diverse objectives, These objectives can be design objectives for a strain, exploitation of the metabolic capabilities of a genotype, or physiologically meaningful objective functions, such as maximum cellular growth.

In one embodiment, growth is defined in terms of biosynthetic requirements based on literature values of biomass composition or, in another embodiment, on experimentally determined values. In another embodiment, biomass generation can be represented as an additional reaction flux draining intermediate metabolites in the appropriate ratios and represented as an objective function Z. In another embodiment, the reaction flux can be formed to utilize energy molecules such as ATP, NADH and NADPH so as to incorporate any maintenance requirement that must be met. This new reaction flux then becomes another constraint/balance equation that the system must satisfy as the objective function. In another embodiment, using linear programming, enables the placement of additional constraints on the value of any of the fluxes in the metabolic network.

In another embodiment, constraints representative of a maximum allowable flux through a given reaction may be determined. For example, in the equation, $\beta_j \leq v_j \leq \alpha_j$, where, in one embodiment, a limited amount of an enzyme is present, the value for $\alpha_j$ would take on a finite value. In another embodiment, constraints may also be used to include the knowledge of the minimum flux through a certain metabolic reaction in which case the value for $\beta j$ would take on a finite value. In another embodiment, one can determine the metabolic resources available to the cell for biosynthesis of essential molecules for biomass. Allowing the corresponding transport fluxes to be active provides the in silico bacteria with inputs and outputs for substrates and by-products produced by the metabolic network. In one embodiment, if one wished to simulate the absence of a particular growth substrate the corresponding transport fluxes are constrained, allowing the metabolite to enter the cell to be zero by allowing $\beta j$ and $\alpha j$ to be zero. In another embodiment, if a substrate is only allowed to enter or exit the cell via transport mechanisms, the corresponding fluxes can be properly constrained to reflect this scenario.

In one embodiment, the addition or removal of constraints on various fluxes in the network enables simulation of a genetic deletion event. Using flux balance analysis, according to this aspect of the invention, it is possible to determine the affects of the removal or addition of particular genes and their associated reactions to the composition of the metabolic genotype on the range of possible metabolic phenotypes.

In one embodiment, if the removal/deletion does not allow the metabolic network to produce downstream, undesireable by-products, the deletion(s) serves to enhance production of a desired metabolite.

In another embodiment, this invention provides a method of identifying genes involved in optimized production of a carotenoid, comprising constructing a flux balance analysis model, applying constraints to said flux balance analysis model, comprising: maximizing cell growth yield subject to a minimization of metabolic adjustment alteration, conducting in silico gene knockout simulations for all genes in the organism's genome, wherein a flux profile comprising a deletion of knocked out genes from the stoichiometry matrix is calculated for said gene knockout simulations; determining enhanced flux profiles as a measure of optimal production of said metabolite, contacting cells comprising genes involved in the carotenoid biosynthetic pathway with a libray of transposon mutagenized genes, selecting cells with enhanced carotenoid synthesis or production, and identifying mutagenized sequences, and inhibiting or abrogating gene expression of combinations of the gene targets identified by flux balance analysis and by transposon mutagenesis, in a cell comprising genes involved in the carotenoid biosynthetic pathway, thereby identifying genes involved in optimized production of a carotenoid.

Figure 9:
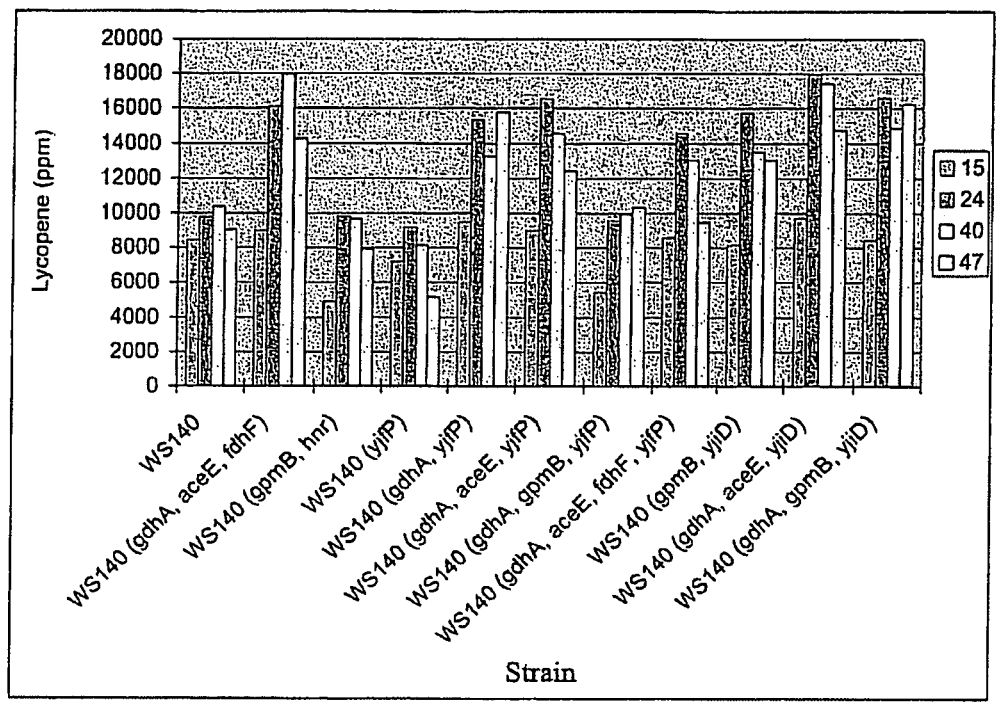
FIG. 9 graphically depicts the lycopene production profiles as a function of time, in selected strains. Bars represent the 15, 24, 40, and 47 hour timepoints. Glucose is added at a level of 5 g/L at 0 and 15 hours, followed by an additional glucose addition of 3 g/L at 24 hours.

In one embodiment, the search technique may generate novel gene targets for increasing the production level of carotenoids, or, in another embodiment, lycopene in E. coli. Indeed, as is exemplified further herein, such a strategy provided a series of gene targets, which when inhibited resulted in enhanced carotenoid production (FIG. 9). In one embodiment, the metabolite comprises a product of the carotenoid biosynthetic pathway.

In one embodiment, knockouts of one or more of the gene targets identified from the transposon mutagenesis method is combined with one or more of the knock-outs from the flux-balance analysis to create combinations that result in increased lycopene titer.

Based on the data provided hereinbelow, many of the best combinations, in terms of carotenoid yield, were not very predictable, therefore the combination of the two methods is in one embodiment, the ideal method for identifying genes involved in optimized production of a carotenoid. In another embodiment, the impact on lycopene product may vary, as a function of the growth stage of the transformed cell, and represents another embodiment of this invention.

In one embodiment, the calculation the flux profile comprises imposing a growth rate minimum. In one embodiment, the growth rate minimum is equal to 0.5-10% of the maximum wild-type prediction of said flux balance analysis model. In another embodiment, the growth rate minimum is equal to 5% of the maximum wild-type prediction of said flux balance analysis model.

In one embodiment, the nonlinear process may be optimized in a manner analogous to the method of steepest descents for nonlinear function optimization. Since this approach may yield, in another embodiment, a local maximum in production, the results may be compared, in another embodiment, to other possible trajectories along the phenotype contour.

In another embodiment, this analysis is not limited to knockout methods. As a constraint-based technique, it is possible to further incorporate regulatory information or even gene amplifications to further extract putative parameters impacting cellular phenotype. By creating floors and ceilings on the constraints, the calculated flux profile may be further restricted to represent unique phenotype behaviors. As such, an over-expression could be represented by an increase in the floor of a constraint while a regulatory network interaction could appear in the ceiling of a constraint by relating it to the flux of another pathway. These alterations would increase the ability to extract more gene targets, which influence cellular phenotype.

In another embodiment, genes involved in carotenoid synthesis, or enhancing carotenoid synthesis may be identified by other mutagenesis methods, and not just via transposon mutagenesis. For example, via chemical mutagens, such as, for example, ethylmethanesulfonate (EMS) or radiation.

When creating mutations through radiation, in one embodiment, ultraviolet (UV) or, in another embodiment, ionizing radiation may be used. Suitable short wave UV wavelengths for genetic mutations may fall within the range of 200 nm to 300 nm, in one embodiment, where 254 nm is preferred. UV radiation in this wavelength principally causes changes within nucleic acid sequence from guanidine and cytosine to adenine and thymidine. Since all cells have DNA repair mechanisms that would repair most UV induced mutations, agents such as caffeine and other inhibitors may be added to interrupt the repair process and maximize the number of effective mutations. Long wave UV mutations using light in the 300 nm to 400 nm range may be used, in another embodiment, and may be used in conjunction with various activators such as psoralen dyes that interact with the DNA, in another embodiment.

In another embodiment, mutagenesis with chemical agents may also be used. Such chemical mutagens may comprise, in other embodiments, chemicals that affect nonreplicating DNA such as $HNO_2$ and $NH_2OH$, as well as agents that affect replicating DNA such as acridine dyes, which have been shown to cause frameshift mutations. Methods for creating mutants using radiation or chemical agents are well known in the art; and any method may be utilized for the methods of this invention (see, for example, Thomas D. Brock in Biotechnology: A Textbook of Industrial Microbiology, Second Edition (1989) Sinauer Associates, Inc., Sunderland, Mass., or Deshpande, Mukund V., Appl. Biochem. Biotechnol. 36, 227 (1992).

In another embodiment, enhanced carotenoid production may be a function of overexpression of a gene. In one embodiment, screening methods for identifying such a gene or genes may be accomplished via isolating genomic DNA fragments following a partial digestion of genomic DNA from a particular organism, or in another embodiment, comparing this between two or more organisms, and subsequently ligating the fragments into a medium-copy (for example, pZE21) and/or high-copy (for example, pUC19) number plasmid. The constructed shotgun libraries are used to transform a desired strain, with transformants screened based on the presence a red color, or in another embodiment, on the development of an intense red color in the transformants. Inserts may then be identified from the transformants, and ORFs identified from the inserts, both of which may be accomplished by methodology well known in the art, and as exemplified in part, hereinbelow. Identified genes may be overexpressed singly, or in another embodiment, in combination, in a cell for enhanced carotenoid production, and represents an embodiment of this invention. In addition, identified genes may be overexpressed in a cell which is disrupted for, or suppressed for or abrogated for expression of a gene identified in other embodiments of this invention, to yield additional engineered strains with enhanced carotenoid production.

It is to be understood that any embodiment described herein, as applicable to any and all methods of this invention, is to be considered as part of this invention.

In one embodiment, the invention provides a genetically engineered cell with enhanced lycopene production, wherein the cell is genetically disrupted for two or more genes identified by the methods described herein. In another embodiment, this invention provides a cell with enhanced lycopene production, wherein the cell is inhibited or abrogated for expression of two or more genes identified by a method of this invention. In another embodiment, the invention provides a genetically engineered cell with enhanced lycopene production, wherein the cell is engineered to overexpress a gene identified by the methods described herein, associated with enhanced carotenoid production. In another embodiment, the invention provides a genetically engineered cell with enhanced lycopene production, wherein the cell is engineered by any of the methods of this invention, or a combination thereof of the methods of this invention, whereby the cell produces enhanced carotenoids, as compared to a parental strain.

The following are meant to provide materials, methods, and examples for illustrative purposes as a means of practicing/executing the present invention, and are not intended to be limiting.

EXAMPLES

Materials and Experimental Methods

Strains and Media

*E. coli* K12 PT5-dxs, PT5-idi, PT5-ispFD was used as the lycopene expression strain when harboring the pAC-LYC [Cunningham F X Jr, et al., Plant Cell, 1994. 6(8): p. 1107-1121] plasmid containing the crtEBI operon. Gene deletions were conducted using PCR product recombination [Datsenko, K. A. and B. L. Wanner, PNAS, 2000. 97(12): p. 6640-6645.] using the pKD46 plasmid expressing the lambda red recombination system and pKD13 as the Kan template for PCR.

The following sets of primers (Table 2) were used in the construction of PCR products to inactivate the respective genes. To verify recombination, internal primers (k1, k2 and kt) were used as described, along with the listed external antisense verification primer.

TABLE 2

Primer sets for knockout generation

| Gene | Strand | SEQ ID NO: | Primer 5' - 3' |
|---|---|---|---|
| gdhA | Sense | 1 | AACCATGTCCAAAAGCGCGACCCGAA TCAAACCGAGTTCGGTGTAGGCTGGA GCTGCTTC |
|  | Antisense | 2 | TCACACCCTGCGCCAGCATCGCATCG GCAACCTTCACAAGGGATCCGTCGAC CTGCAGTT |
|  | Verification | 3 | GATAAGCGTAGCGCCATCAG |
| gpmB | Sense | 4 | GGGCCAGTCTGACAGCCCGCTGACCG CCAAAGGTGAGCAA GTGTAGGCTGG AGCTGCTTC |
|  | Antisense | 5 | CGGCGCTCTGCCCATGCTGGTAATCC GAGAATCGTACTCATCCGTCGACCTG CAGTTCGA |
|  | Verification | 6 | CCCAATTAATCTACGCTGTG |
| aceE | Sense | 7 | TAAATTCCTGAAATATCTGGAACACC GTGGCCTGAAAGAT GTGTAGGCTGG AGCTGCTTC |
|  | Antisense | 8 | TGGAAGCCGAACATCGAGTAATAGAT GTAGAACGGGATCA TCCGTCGACCT GCAGTTCGA |
|  | Verification | 9 | ACGCTCCAGACCGTCATGCA |
| ppc | Sense | 10 | AGCTCAATACCCGCTTTTTCGCAGG TTTTGATTAATGCATGTGTAGGCTG GAGCTGCTTC |
|  | Antisense | 11 | GGAAGTGAACGCCTGTTTAAAACAG CTCGATAACAAAGATGGATCCGTCG ACCTGCAGTT |
|  | Verification | 12 | GCAAAGTGCTGGGAGAAACCATCAA |
| talB | Sense | 13 | ATGACGGACAAATTGACCTCCCTTC GTCAGTACACCACCGGTGTAGGCTG GAGCTGCTTC |
|  | Antisense | 14 | ACGGATACCTTCCGCCAGTTTATCT ACTGCCATTGGATCCTCCGTCGACC TGCAGTTCGA |
|  | Verification | 15 | TGATACACTGCGAAGGGAGTGACAG ACAGG |
| fdhF | Sense | 16 | ACGGTAAAATAACATCCGCCGCCGA CGCGGTTTTGGTCATGTGTAGGCTG GAGCTGCTTC |
|  | Antisense | 17 | GCATCAGGTTGCAAAATCAACCTGG TCGTCGATAACGGCA TCCGTCGAC CTGCAGTTCGA |
|  | Verification | 18 | CGCGGTATTTCGTTTCGTCA |

Gene knockouts were verified through colony PCR. Strains were grown at 37° C. with 225 RPM orbital shaking in M9-minimal media [Maniatis, T., et al., Molecular cloning: a laboratory manual. 1982, Cold Spring Harbor, N.Y.: Cold Spring Harbor Laboratory Press] containing 5 g/L d-glucose and 68 μg/ml chloramphenicol. All cultures were 50 ml grown in a 250 ml flask with a 1% inoculation from an overnight 5 ml culture grown to stationary phase. All experiments were grown in replicate to validate data and calculate statistical parameters. Glucose monitoring was conducted periodically using a YSI2300 glucose analyzer to verify complete usage of glucose. Cell density was monitored spectrophotometrically at 600 nm.

Transposon Library Screening and Sequencing

Transposon libraries were generated using the pJA1 vector (Badarinarayana, V., et al., Selection analyses of insertional mutants using subgenic-resolution arrays. Nat. Biotech., 2001. 19(11): p. 1060-1065). Cells were transformed with between 800 and 1600 ng of the plasmid, then grown in 50 ml LB under 20 μM IPTG induction conditions until an OD600 of 0.4. Following this outgrowth, cells were diluted and plated on M9-Glucose-Agar plates with a target density of 200 colonies per 150×15 mm petri dish plates. Plates were incubated at 37° C. for 36 hours, then allowed to sit at room temperature. Cells identified as exhibiting increased lycopene content (more red) were isolated and cultured. The identity of promising targets were sequenced using an abbreviated version of Thermal Asymmetric Interlaced PCR (TAIL-PCR) (Liu, Y., Thermal Asymmetric Interlaced PCR: Automatable Amplification and Sequencing of Insert End Fragments from P1 and YAC clones for Chromosome Walking. Genomics, 1995, 25: p 674-681). For the TAIL1 reaction, 1.5 μL of genomic DNA isolated using the DNA purification kit (Promega) was used as the initial template. The TAIL3 reaction was increased to 30 cycles. Kanamycin specific primers TAIL1—TATCAG-GACATAGCGTTGGCTACCCG (SEQ ID NO: 19), TAIL2—CGGCGAATGGGCTGACCGCT (SEQ ID NO: 20), TAIL3—TCGTGCTTTACGGTATCGCCGCTC (SEQ ID NO: 21). The degenerate primer AD1 was used as described in the reference. The product of the TAIL3 reaction was purified by a PCR cleanup kit (Qiagen) after gel visualization. This product was sequenced using the primer TAIL-seq—CATCGCCTTCTATCGCCTTCTT (SEQ ID NO: 22). Glycerol stock aliquots were created by centrifuging cultures and reducing them to a volume of 10 ml to which 2 ml 50% glycerol was added. These aliquots were used for inoculation of the pJA1 transposon library cultures. All PCR products were purchased from Invitrogen and utilized Taq polymerase, M9 Minimal salts were purchased from US Biologics and all remaining chemicals were from Sigma-Aldrich.

Lycopene Assay

Intracellular lycopene content was extracted from 1 ml of bacterial culture at the point of total glucose exhaustion. The cell pellet was washed, and then extracted in 1 ml of acetone at 55° C. for 15 minutes with intermittent vortexing. The lycopene content in the supernatant was quantified through absorbance at 475 nm [Kim, S. W. and J. D. Keasling, Biotechnology and Bioengineering, 2001. 72(4): p. 408-415] and concentrations were calculated through a standard curve. The entire extraction process was performed in reduced light conditions to prevent photo-bleaching and degradation. Cell mass was calculated by correlating dry cell with OD600 for use in ppm calculations.

Flux Balance Analysis Calculations

Application of FBA to the carotenoid system required including the non-endogenous reactions (crtEBI) required for the production of these molecules on the background of previously published stoichiometric models [Edwards, J. et al., Proc Natl Acad Sci USA, 2000. 97: p. 5528-5533; Segre, D., et al., PNAS, 2002. 99(23): p. 15112-15117] with alterations in the isoprenoid biosynthesis pathway (see supplemental information). The resulting model consisted of 965 fluxes involving 546 metabolite intermediates. This model was solved subject to MOMA using the linear and quadratic programming methods using a PERL script [Edwards, J. et al., Proc Natl Acad Sci USA, 2000, 97: p. 5528-5533; Segre, D., et al., PNAS, 2002. 99(23): p. 15112-15117]. An additional script was used to perform the genome-wide knockout searches. For the calculation parameters, values for the glucose uptake, oxygen uptake and nitrogen uptake were set at 5, 200, and 1000 respectively. These values allow for glucose to be the limiting substrate in these calculations. Single knockout calculations were performed on a Pentium IV Linux platform while the exhaustive double knockout search was performed on six Power PC 1.5 GHz microchips on an AIX platform.

Example 1

Gene Target Identification for Lycopene Production in Single Gene Knockout Simulations The E. coli iJE660a GSM model [23] served as the basis for the stoichiometrically balanced, genome-wide bioreaction network of E. coli metabolism, and the lycopene production pathway was utilized for identification of gene targets (FIG. 1). Additionally, the crtEBI operon was added to the model along with updated isoprenoid synthesis reaction details discovered after the formulation of this model (Table 3).

TABLE 3

Alterations of the iJE606a GSM—The following more comprehensive isoprenoid biosynthesis pathway was created:

| Pathway | Gene | Reaction |
|---|---|---|
| Isoprenyl-pyrophosphate synthesis pathway | dxs | T3P1 + PYR → DXP + $CO_2$ |
| | ispC | DXP + NADPH ↔ MEP + NADP |
| | ispD | MEP + CTP → CDPME + PPI |
| | ispE | CDPME + ATP → CDPMEPP + ADP |
| | ispF | CDPMEPP → MECPP + CMP |
| | ispG | MECPP ↔ HMBPP |
| | ispH | HMBPP → 0.5 IPPP + 0.5 DMPP |
| Isoprenyl pyrophosphate isomerase | idi | IPPP ↔ DMPP |
| Farnesyl pyrophosphate synthetase | ispA | 2IPPP → GPP + PPI |
| Geranyltranstransferase | ispA | GPP + IPPP → FPP + PPI |
| Octoprenyl pyrophosphate synthase (5 reactions) | ispB | 5 IPPP + FPP → OPP + 5 PPI |
| Undecaprenyl pyrophosphate synthase (8 reactions) | | 8 IPPP + FPP → UDPP + 8 PPI |
| Lycopene Pathway | crtE | IPPP + FPP → GGPP + PPI |
| | crtB | 2 GGPP → PHYTO + PPI |
| | crtI | PHYTO → LYCO |

The reactions listed in Table 3 utilize the following metabolite abbreviations which were either created or used from the original model (Table 4).

TABLE 4

Metabolite Abbreviations:

| Abbreviation | Metabolite |
|---|---|
| CDPME | 4-diphophocytidyl-2-C-methyl-d-erythritol |
| CDPMEPP | 4-diphosphocytidyl-2-C-methyl-2-phosphate-d-erythritol |
| DMPP | Dimethylallyl pyrophosphate |
| DXP | 1-deoxy-d-xylulose-5-phosphate |
| FPP | trans, trans Farnesyl pyrophosphate |
| GGPP | Geranylgeranyl PP |
| GPP | trans Geranyl pyrophosphate |
| HMBPP | 1-hydroxy-2-methyl-2(E)-butenyl-4-diphsophate |
| IPPP | Isopentyl pyrophosphate |
| LYCO | Lycopene |
| MECPP | 2-methyl-d-erythritol-2,4-cyclodiphosphate |
| MEP | Polyol 2-C-methyl-d-erythritol-4-phosphate |
| OPP | trans Octaprenyl pyrophosphate |
| PHYTO | Phytoene |
| PPI | Pyrophosphate |
| PYR | Pyruvate |
| T3P1 | Glyceraldehyde 3-phosphate |
| UDPP | Undecaprenyl pyrophosphate |

Using this updated model, a total of 965 metabolic fluxes were calculated such as to: (a) balance the rates of synthesis and depletion of 546 metabolites, (b) maximize cell growth yield subject to a Minimization of Metabolic Adjustment (MOMA) alteration for suboptimal systems, and (c) utilize glucose as the sole carbon source [7, 9]. Initially, the maximization of lycopene production was set as the objective function to extract characteristic phenotype behavior. Simulations revealed a direct inverse relationship between the stoichiometric maximum lycopene yields and growth yield and direct relationship between stoichiometric maximum lycopene yields and glucose uptake sates (data not shown). Therefore, these two relationships suggested the need to reduce the growth yield and maintain a relatively high glucose uptake rate to support enhanced lycopene production.

Through the use of the model using the maximum growth objective function subject to a MOMA alteration, in silico genome-wide gene knockout simulations were conducted. The phenotype of specific gene knockouts was simulated by deleting the corresponding enzyme (i.e., reaction) from the stoichiometry matrix and calculating the resulting flux profile. To avoid selecting mutants with extremely low growth rates and no increased production, a minimum growth requirement was enforced. knockout candidates were compared on the basis of predicted production level after invoking the growth requirement.

Figure 2:
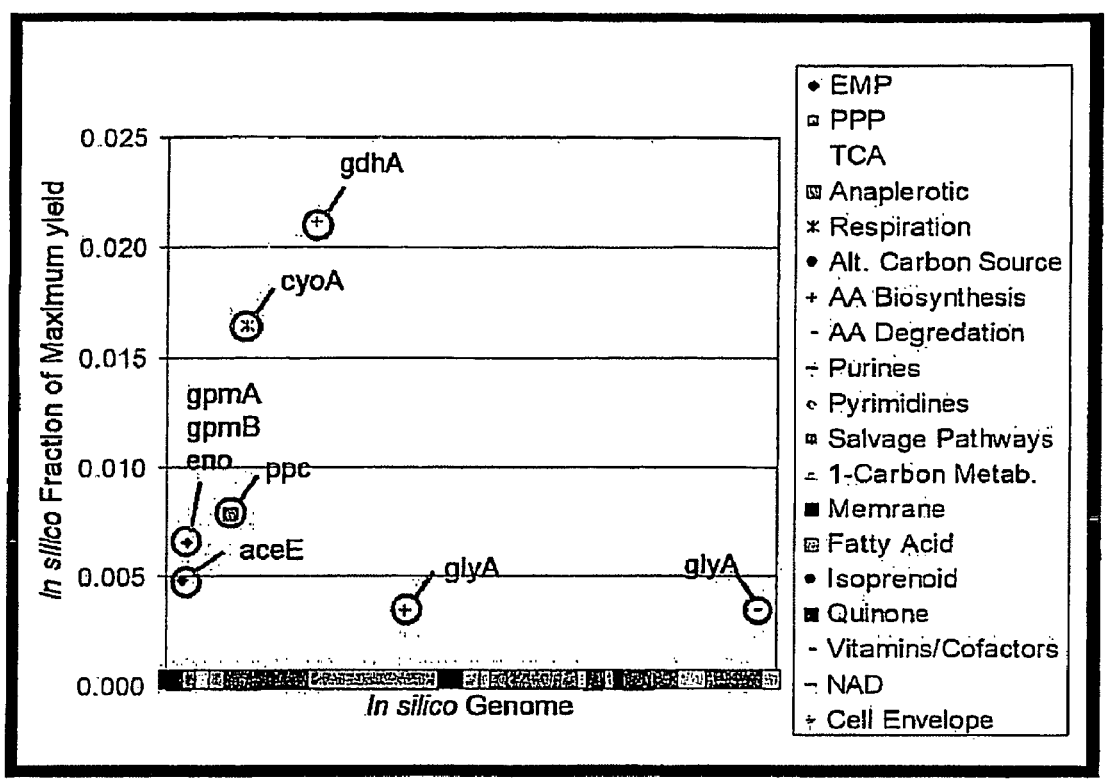
FIG. 2 schematically depicts an in silico genome-wide single knockout simulation. The resulting phenotype for every possible single gene knockout was simulated using FBA with MOMA as an additional constraint. The resulting genotype-phenotype plot illustrates the effect of single gene deletion on lycopene production. A single knockout scan predicted eight genes whose deletion yielded enhanced product synthesis while satisfying a minimum growth requirement. The gene glyA appears twice since its function can be classified as both amino acid biosynthesis and vitamin/cofactor metabolism.

Results of a genome scan for single gene knockout mutants using the above criteria identified eight single gene knockouts which would produce a higher yield of lycopene by direct enhancement of the lycopene pathway and, indirectly, by lowering growth yield (FIG. 2). Of the eight predicted genes, two were eliminated from further consideration: glyA, due to a very low knockout metric and cyoA that has previously been reported as lethal for *E. coli* growth. After these exclusions, four clusters of genes remained, and gdhA, gpmB, aceE and ppc were selected as candidates, for experimental validation. While gpmA and eno also appeared as candidates, they were not selected as the predicted phenotype was similar to gpmB. Furthermore, gpmB is the more prevalent isoenzyme form of the phosphoglycerate mutases (gpmA and gpmB) in *E. coli* during the growth phase [24] and no prior strain containing the single knockout of eno was found in a literature search. Additionally, ppc knockouts were found to be not viable in non-supplemented glucose-based media.

Of the four selected genes, all but gdhA apparently directly impact the supply of lycopene precursors supply while the gdhA knockout increases the availability of NADPH, an important cofactor for lycopene synthesis. Furthermore, in silico predictions indicated a reduced growth phenotype for each of these knockouts ranging between 20% and 80% of the maximum yield. These results are consistent with prior strategies for increasing secondary metabolite production aiming at the reduction of byproduct formation, balancing of precursors and, in some cases, lowering the growth rate However, while these results conform to the accepted strategy for increasing secondary metabolite production, the latter is a poor substitute for a more quantitative approach as it identifies many more genes whose effect is not possible to rank and evaluate a priori.

Example 2

Multiple Knockout Simulations

Optimization of a multigenic phenotype, such as lycopene production, depends on the modification of several genes. Hence, multiple gene knockouts need to be similarly evaluated, The difficulty lies in the exhaustive investigation of all possible gene knockout combinations necessary, which leads to combinatorial explosion: 965 C 2 combinations of all the possible double mutants, and so on. Hence, sequential optimization approaches were invoiced whereby single gene knockouts were investigated in the genetic background of deletion mutants identified for their improved phenotype from previous iterations. Such procedures emulate optimization routines of the type of steepest descent for non-linear optimization problems. However, while properties of continuity and convexity assure of a certain degree of success in the solution of mathematical problems, no such properties have been demonstrated for metabolic networks. Consequently, there can be no assurance about the results of such sequential optimization procedures.

Figure 3:
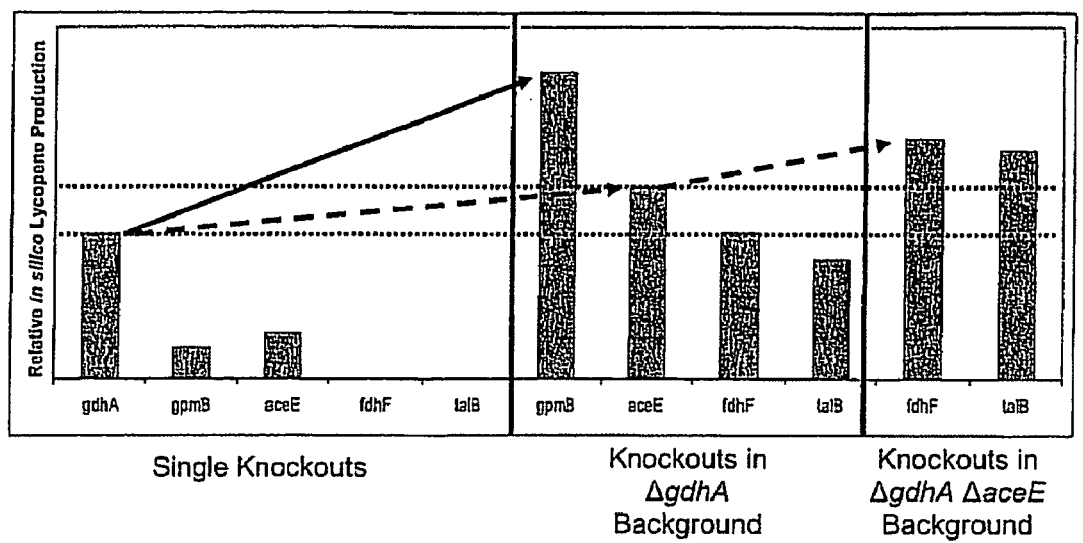
FIG. 3 schematically depicts an in silico multiple gene knockout simulation search strategy. This figure illustrates the method of maximal sequential phenotype increase. The production levels for each background are obtained through genome scans similar to that shown in FIG. 2, but by changing the genetic background of the starting strain. A triple knockout construct based on the double mutant gdhA/gpmB was excluded as it violated the minimum growth rate requirement. On the other hand, predicted triple constructs in gdhA/aceE background continue to show an increase in lycopene yield. The path of maximal phenotype increase is given by the solid line. However, since a gdhA/gpmB knockout has been excluded for triple knockouts due to growth rate, the next highest optimal path, given by the dashed line shows the pathway towards maximal phenotype increase. These results indicate that novel gene targets arise as the genotype is altered as result of gene knockouts. This is especially evident in the case of talB. Although talB increases the production level in a gdhA/aceE knockout background, it is detrimental in a gdhA knockout background.

Multiple gene knockout mutants were investigated following a sequential approach: A gene was first identified whose deletion yielded maximum lycopene improvement and double mutants were subsequently sought in the genetic background of the single gene knockout, and so on for higher mutants. Certain combinations of gene knockouts yielded extremely reduced growth phenotypes in silico, so a growth rate minimum was required of all mutants equal to 5% of the maximum, wild-type prediction. Under these constraints, several interesting multiple gene candidates arose. Unlike the single knockout candidates, multiple knockouts tend to place higher emphasis on favoring energetics and cofactor availability. FIG. 3 summarizes the results of several multiple knockout constructs of considerable interest. As a double knockout construct, gdhA/gpmB is predicted to outperform the other candidate combinations. However, triple knockout constructs based upon gdha/gpmB are predicted to have an extremely low growth rate (less than the 5% threshold), which warrants their removal from further consideration on the basis of the minimum growth rate requirement despite their predicted high product yield. Additionally, talB and fdhF, although absent as single knockout candidates, become key gene targets in the construction of double or triple knockout mutants. Of further interest, the gene talB is predicted to improve production in a gdhA/aceE background, yet it decreases the yield in the gdhA background when the enzymatic activity of aceE is active. FIG. 1 depicts the reaction network context of these candidate gene targets. It underlines the rationale for specific combinations, such as aceE followed by fdhF as a knockout scheme. In this case, the knockout of aceE would presumably increase formate production, whose flux may then be redirected through an fdhF knockout. These features illustrate the need for the invoiced systematic approach to gene knockouts.

Next a comparison between the above results and those obtained by an exhaustive investigation of all possible double mutants was conducted. An exhaustive simulation is computationally expensive, however provides insight into the topology and behavior of the metabolic space. At the end of this simulation, the highest yielding viable knockout (two cyoA combinations were excluded) was determined to be a gdhA/gpmB construct, which is consistent with the result obtained using the sequential approach. Additionally, several unique features of this topology were determined: (1) the lethality of a gene knockout could not be revered through an additional knockout, (2) the combination of two non-lethal genes could be lethal when combined, and (3) gene knockouts were not found to significantly increase the cellular phenotype.

Figure 4:
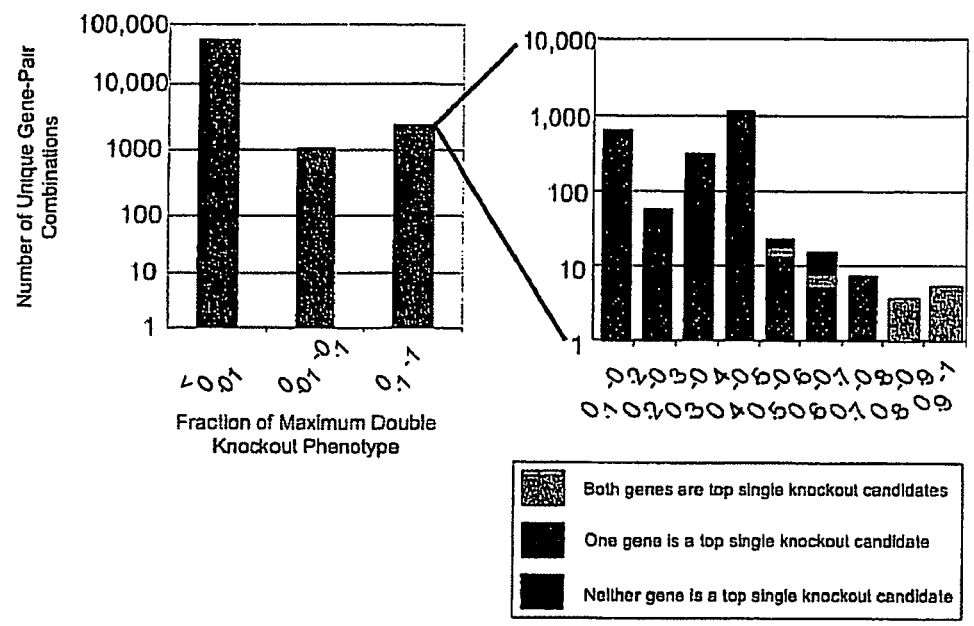
FIG. 4 demonstrates the results of an exhaustive search supporting the results obtained via a sequential knockout method. An exhaustive, simultaneous double knockout search was performed using FBA. In the first graph, it is evident that the majority of gene knockouts have little impact on lycopene production levels. The data presented has been filtered based upon the 5% maximum growth requirement. The second graph stratifies the top 90% of the double knockout phenotypes found by this exhaustive search. These results indicate that 98.6% of these combinations consist of either one or more genes from top candidates found from the single knockout illustrated in FIG. 2. More importantly, all of the maximum phenotypes can be identified through the sequential search.

Following the path of maximal phenotype increase for predicting double knockout constructs cannot extract a combination of two synergistic genes, which have no phenotype impact individually as single knockouts. As depicted in FIG. 4, of the top 90% phenotypes in the double knockout metabolic space, 98.6% contain at least one gene, which elicits a high increase in yield as a single knockout. Therefore, only 1.4% of the most desirable double knockout constructs would be unattainable following a sequential approach to target identification. As a result, the simultaneous approach would be required only to attain the 1.4% of desirable double knockout genotypes.

Example 3

Experimental Investigation of Single and Multiple Gene Knockouts Confirmed FBA Predictions Gene knockout experiments were conducted along with shaker-flask fermentations to experimentally test the predictions of the previous simulations. Knockout constructs were created using PCR product inactivation in a recombinant *E. coli* strain already engineered to produce lycopene at high yields through over-expressions of the dxs, ispFD, and idi genes (see Materials and Methods). This strain was heterologously expressing the crtEBI operon on a pAC-LYC plasmid encoding for the genes required to produce lycopene [25]. FIG. 5 summarizes the results from nine so constructed knockout mutants and presents the lycopene production at the point of glucose exhaustion when strains were grown in an M9-minimal media with glucose as the sole carbon source. To facilitate comparison, simulation results are juxtaposed to experimental data. First, there is continuing improvement of lycopene yield with an increase in the number of gene knockouts. This trend reflects the selection criteria applied in the identification of targets. Second, the gdhA/gpmB double knockout construct produced the highest yield among double knockouts at 18% above the parental strain; however cell growth was reduced along with glucose uptake, as predicted by the simulations. Third, following the path of highest product yield in combination with the minimum growth requirement produces a triple knockout construct of gdhA/aceE/fdhF produced the highest yield of 37% more than the parental strain. Finally, gene targets selected as being important in triple knockout constructs, matched computational predictions to be either ineffective as single knockouts (fdhF) or detrimental as double knockouts (talB in gdhA background). Overall, the experimental results agreed with the trends indicated by the simulations.

Since the predictions were based on pure glucose as carbon source, nonviable knockouts such as ppc were excluded from further analysis. Despite this fact, ppc was still shown to impart an increase in lycopene yield compared to the parental strain when grown in minimal media with 0.3% Casamino acid supplementation (data not shown).

Example 4

Figure 6:
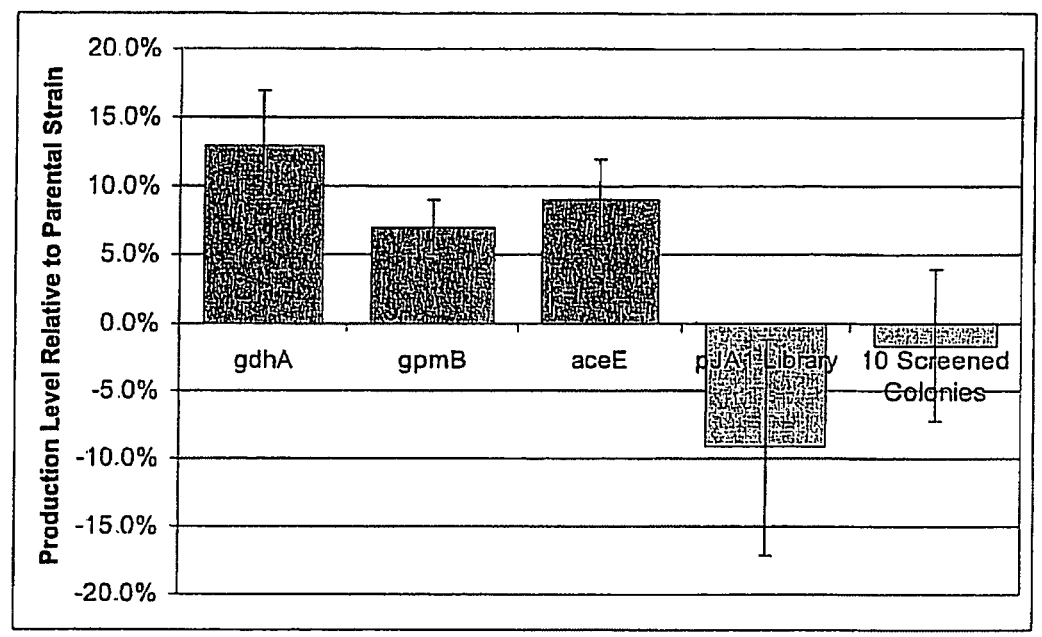

FBA Simulations Outperformed Transposon Mutagenesis in the Identification of Critical Genes It is important to examine the significance of these results relative to the lycopene yield improvements afforded by the deletion of other genes not identified by the flux balance simulations, including random genes of the *E. coli* genome. To this end, libraries of random genome transposon knockouts using the pJA1 vector [Badarinarayana, V., et al., Nat. Biotech., 2001. 19(11): p. 1060-1065] were constructed. Such randomized libraries did not show any significant increase in the overall lycopene yield, which is illustrated by FIG. 6. In fact, random transposon mutagenesis appeared to decrease the lycopene production on average. The wild-type strain was initially compared to eight cultures of random transposon-integrated libraries. To ensure that these libraries are heterogeneous in nature, individual colonies were selected and cultured separately in shaker-flasks. The average production level of these selected genes was comparable to that of the pooled transposon library. In general, the transposon knockouts performed as well as the parental strain, but worse than the systematically determined knockouts. This result underlines the significance of the genes identified through the FBA simulation. Additionally, an experimental combinatorial search fails to provide novel leads for multiple knockout constructs due to the lack of tools to create multigenic knockout libraries. Therefore, a sequential search based on the most comprehensive model available provides the best leads to multigenic modifications required to produce a desired phenotype.

Example 5

Identification of Combinatorial Gene Targets

A total of 7 sets of mutations (ΔgdhA, ΔaceE, ΔgpmB, ΔfdhF, ΔgdhA ΔaceE, ΔdghA ΔgpmB, ΔdghA ΔaceE ΔfdhF), which were identified via global, stoichiometric analysis of metabolism were found to alter the production profile of lycopene. These seven mutations along with the parental strain comprise systematically designed strains, as referred to hereinbelow.

To identify combinatorial targets responsible for regulatory, kinetic, or unknown factors (either not included in the model or unknown in function), a global transposon library search in the background of the parental strain was used to identify gene targets, which increased lycopene production. Screening the library on minimal media plates identified three genes, which showed an increase in the production of lycopene when these mutations were introduced into the cell.

The genes hnr (also known as RssB), yjfP and yjiD were found to be combinatorial targets. The gene hnr is a response regulator responsible for recruiting the proteolysis of the stationary phase sigma factor (rpoS). It is interesting to note that rpoS has been implicated as playing an important role in the production of carotenoids in *E. coli*. The gene yjfP is a 249 amino acid protein, which is currently not annotated, but has been categorized as a non-peptidase homologue through homology search. yjiD is a 130 amino acid protein with an unknown function. For this target, the transposon was found to be inserted between the identified promoter region and the gene for yjiD. FIG. 7 indicates relative increase in lycopene production of the parental strain with each of these three individual knockouts at the point of glucose depletion. Using these three identified targets, it is possible to create a total of seven gene combinations of single, double, and triple combinatorial target mutations. These seven combinations along with the parental strain form a total of eight possible combinatorial strains.

Example 6

Combination of Combinatorial and Systematic Targets

An outline of the gene knockout target identification from both systematic and combinatorial approaches is depicted in FIG. 8A. From the systematic and combinatorial targets obtained for the lycopene production systems, two orthogonally determined sets of mutations arise. Many strain improvement programs are able to identify varying targets talking advantage of a number of molecular biology tools. However, it is not clear how to optimize such a system or how each of these targets will interact when combined. To answer these questions, an exhaustive analysis of the 64 strains comprising all combinations of the eight systematic and eight combinatorial mutations was conducted. Each of these strains was evaluated on the basis of lycopene production over the course of a 48 hour fermentation process. The resulting production profiles allowed for a mapping of the metabolic landscape.

Figure 8B:
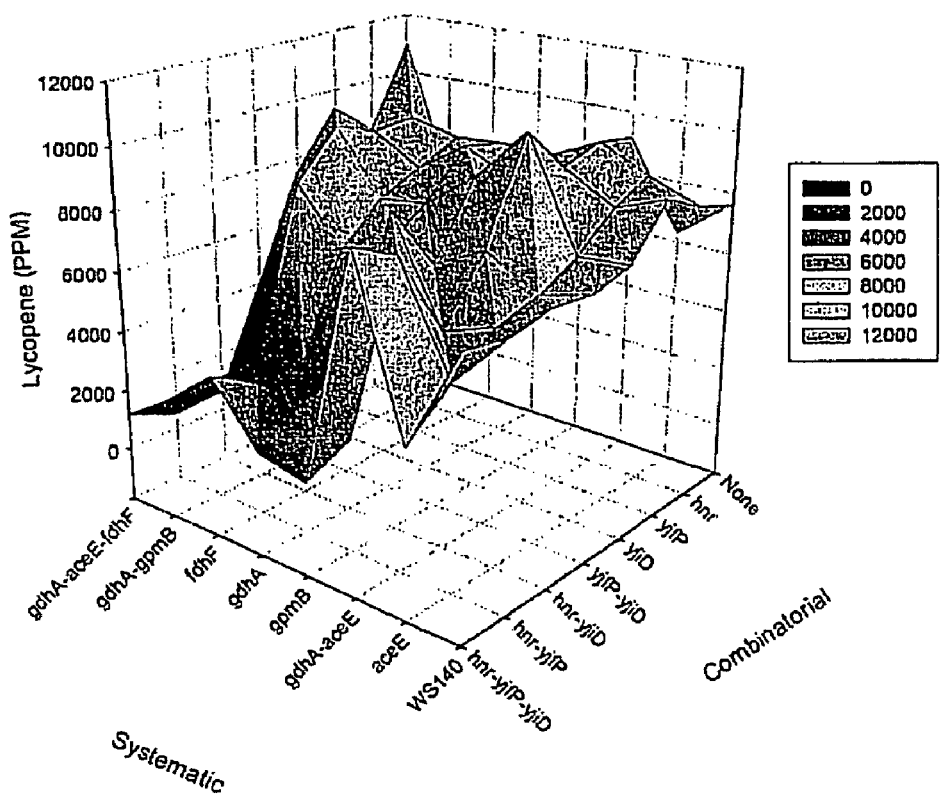
FIG. 8B graphically represents the metabolic landscape depicting the maximum lycopene production over the course of a 48 hour shaker-flask fermentation.
Figure 8:
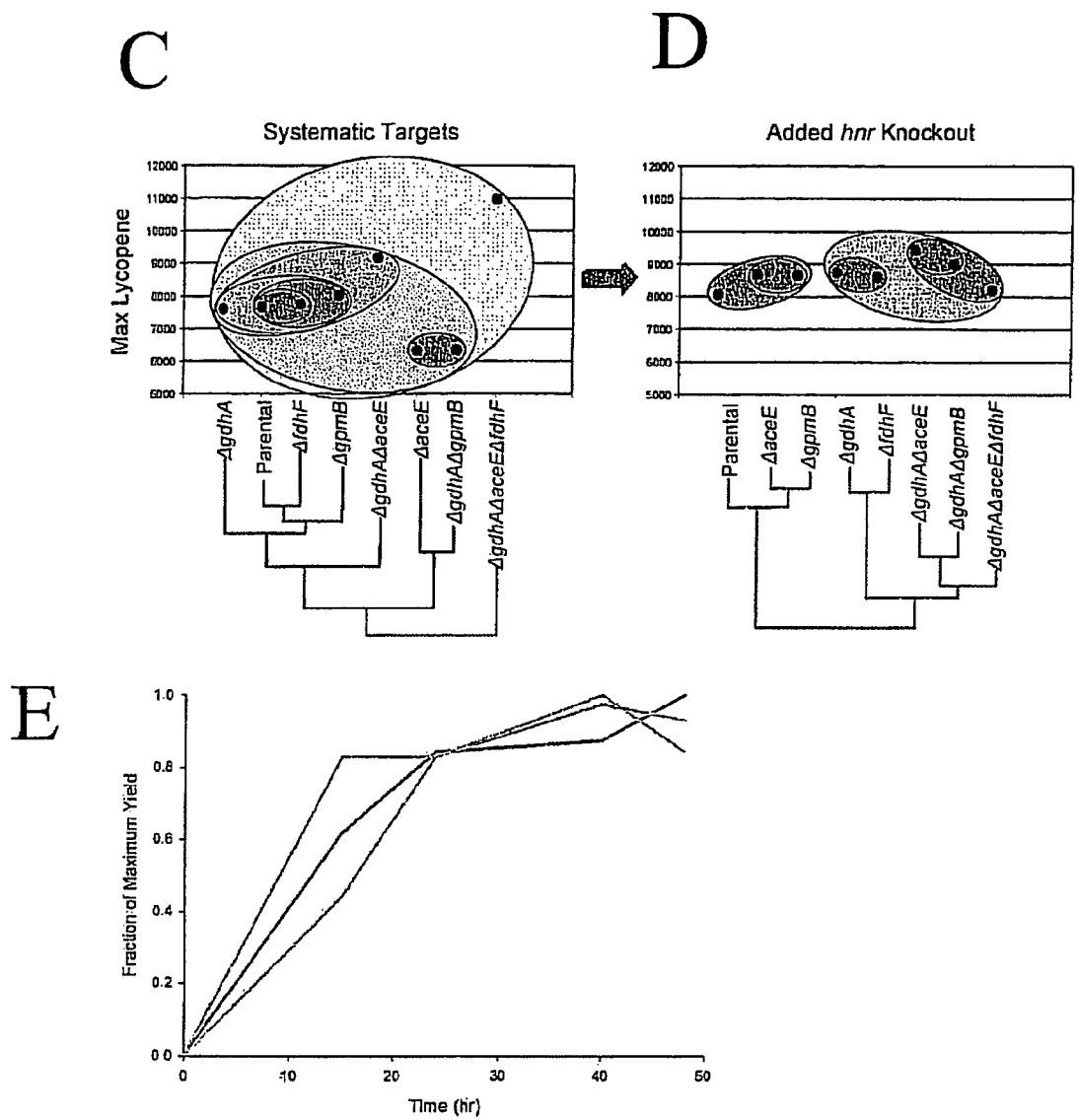
FIG. 8 depicts various parameters obtained for identified systematic and combinatorial gene knockout targets.

FIG. 8B presents the metabolic landscape for the maximum lycopene production over the course of the fermentation.

Two global maxima existed, each with production levels around 11,000 PPM, the ΔgdhA ΔaceE ΔfdhF strain, which was a purely systematically designed strain and the ΔgdhA ΔaceE ΔyjiD strain, which was created through the combination of systematic and combinatorial targets. Several local maximum points with production levels ranging from 8,400-9,400 PPM were found, which were each formed from the combination of systematic and combinatorial targets. The left quadrant of the graph indicated that the combination or stacking of the combinatorial targets greatly reduced production levels of lycopene to below 2000 PPM, and as low as only 500 PPM for some constructs. It is interesting to note that 500 PPM is lower than the production level in a wild-type strain of E. coli K12 devoid of up-regulations in the isoprenoid pathway. Visual inspection indicated that the landscape was highly-nonlinear with many optima and minima.

Clustering methods have been routinely applied for the analysis of microarray (and other) data to determine sets of genes that exhibit similar expression profiles. Likewise, the technique of hierarchical clustering may be applied to the metabolic landscape of FIG. 8B in order to cluster gene knockout constructs exhibiting similar production profiles over the four time points. Presumably, strains clustering most closely accumulate product by following similar mode-of-action in the mechanism of lycopene production. To this end, a complete linkage hierarchical clustering of the lycopene time profiles for the entire 8×8 strain matrix was performed using the Euclidean distance as the similarity metric. Upon clustering the entire set of 64 strains, two distinct organizations emerged for the two sets of gene targets previously identified.

Clustering lycopene profiles (across the four time points) for the eight stoichiometric knockout strains revealed a fairly close, stacked dendrogram (see abscissa of FIG. 8C). When these strains were plotted against the lycopene accumulation level, they revealed an expanding concentric bubble-plot suggesting an additive effect of accumulating gene deletions. This is in concert with the presumed mode-of-action in these strains, namely the increasing availability of precursors and cofactors that are needed for lycopene biosynthesis. This is further evidenced by the close clustering of strains like ΔfdhF and the parental strain, as the fdhF single knockout was determined from the stoichiometric analysis to bring about no enhancement of lycopene production.

FIG. 8D shows the clustering of lycopene time profiles for the knockout strains obtained by combining each of the 7 stoichiometric targets with the combinatorial target gene hnr. In contrast to FIG. 8C, all combinatorial targets, as exemplified by hnr, force a split-tree shape in the dendrogram. Different time courses in lycopene accumulation suggest different modes-of-action for the effect of the combinatorial genes on this phenotype. Specifically, while each of the single knockout constructs formed from the combinatorial targets tended to exhibit similar behavior (increased production), the combination of these genes was not necessarily linear or synergistic. In fact, the double and triple knockout constructs arising from these combinatorial targets exhibited vastly different production profiles from the individual targets (FIG. 8B). This non-linearity suggested that the combinatorial targets disrupt regulatory processes that are relatively incompatible, and in certain cases deleterious, when combined.

As further example of the differences observed when combinatorial genes are combined with stoichiometric ones, the top branch of the strain cluster comprising the parental strain, aceE and gpmB single knockouts (FIG. 8D) all exhibited an extended lag phase which extended to 16-18 hours. Beyond this point, the lycopene production increased as the cells reached stationary phase at a typical cell density OD 3.5-4.0. In contrast, any strain with a gdhA knockout did not posses such a lag phase and had typical cell growth profiles reaching stationary phase by 15 hours. A second cluster comprising gdhA and fdhF single knockouts had a production profile that remained flat between 15 and 24 hours, then increased in the later portion of the fermentation. Finally, the remaining constructs exhibited a steady increase of lycopene production with time. FIG. 8E compared the average, scaled production profiles for the purely systematic cluster and two clustered forced by an hnr deletion. The branched pattern was exhibited by all strains constructed from the deletion of any combinatorial gene in the background of the stoichiometric targets, with different production profiles characterizing each of the clusters.

As illustrated in FIG. 8B, combining stoichiometric and combinatorial targets created a complex metabolic landscape with several local and global optima. The nonlinear effects of the regulatory and unknown targets led to the complex topology of this landscape. In particular, stacking combinatorial targets upon the systematic design of the stoichiometric targets led to a decoupling of the stoichiometric logic. This decoupling was evident in analyzing the impact of the hnr or any other combinatorial constructs on the shape of the dendrogram resulting from hierarchical clustering of the time-series data for the eight stoichiometric strains.

As a reinforcement of the results described above, statistical metrics may be used to quantify the interaction between systematic and combinatorial gene targets. As such, quantitative metrics beyond clustering assessed the source of nonlinearity in the production phenotypes of the 64 strains. First, covariance analysis of the purely systematic targets yielded all positive values, which reinforced the clustering analysis that this subset of genes alters the lycopene phenotype with a similar mode-of-action. Conversely, the combinatorial genotypes had both positive and negative covariances which illustrate the incompatible nature of these targets, Finally, an Analysis of Variance (ANOVA) highlighted the source of variance between production profiles due to the combinatorial genotypes, not the stoichiometric targets ($p=9^{-9}$ vs. 0.35). As a result of these analyses, the major nonlinearities entering into the genotype-phenotype landscape were mostly due to regulatory or unknown factors as opposed to stoichiometry.

Example 7

Performance of Selected Combinatorial and Systematic Targets in Altered Culturing Conditions To further assess the improvement of carotenoid production on the identified strains, selected mutants were cultivated in batch bioreactors and fed-batch shake-flasks. Furthermore, a more controlled feed of glucose (5 g/L at 0 hours and 15 hours, and 3 g/L at 24 hours) and enriched salt media (using 2× M9 media formulation to double the salt concentration). FIG. 9 illustrates the lycopene production levels in these experiments. Production levels were comparable in the ΔgdhA ΔaceE ΔfdhF and the ΔgdhA ΔaceE ΔyjiD strain strain, which reached 18,000 PPM after 40 hours and the ΔgdhA ΔaceE ΔyjiD strain, which reaches the same value in only 24 hours. Additionally, while the specific production level of the ΔgdhA ΔgpmB ΔyjfP strain is only around 10,000, the cell density is greatly increased by nearly 33%, which increases the volumetric productivity of lycopene.

Example 8

Screening And Identification Of DNA Fragments Whose Amplification Impacts Lycopene Production in *E. coli*

As an experimental search of overexpression gene targets, *E. coli* genomic DNA fragments, which enhance lycopene production when they are amplified using *E. coli* genomic libraries on multi-copy plasmids were screened. Genomic DNA fragments of different sizes (0.5-1 kbp, 1-3 kbp, and 3-8 kbp) were isolated after a partial digestion of *E. coli* genomic DNA and subsequently ligated into a medium-copy (pZE21) and high-copy (pUC19) number plasmid. The constructed shotgun libraries were transformed into the *E. coli* DH5 strain containing pACLYC plasmid, in order to screen for DNA fragments, which improve lycopene production.

Since red color formation in a colony becomes more intense as the *E. coli* strain accumulates more lycopene in the cell, colonies exhibiting an intense red color, as compared to background, were screened. More than 30,000 colonies generated after transformation with each library were screened, by evaluating the development and intensity of the red-color.

The transformed plasmids were isolated from the red-color colonies, and they were then retransformed into the *E. coli* DH5 (pACLYC) strain to confirm if the inserts in the isolated plasmids were responsible for formation of the intense red color. Following confirmation, the insert sequences were identified by searching the sequencing results of the 5' and 3' region of the inserts against the *E. coli* K12 genome sequence. Depending on the size of inserts and copy number of the plasmid used for the library construction, different inserts with some consensus were identified from the screening (Table 5). By using *E. coli* DH5α (pACLYC) strain as a parental strain of the transformation of the libraries, a total of 37 inserts were identified, which represented 16 independent regions of the *E. coli* genome, from the screening with the libraries containing 1-3 kbp and 3-8 kbp inserts. However, the library containing 0.5-1.0 kbp inserts did not generate any colony exhibiting intense red-color.

Table 5. Inserts Identified from the Screen Based on Red Color Development

Figure 10:
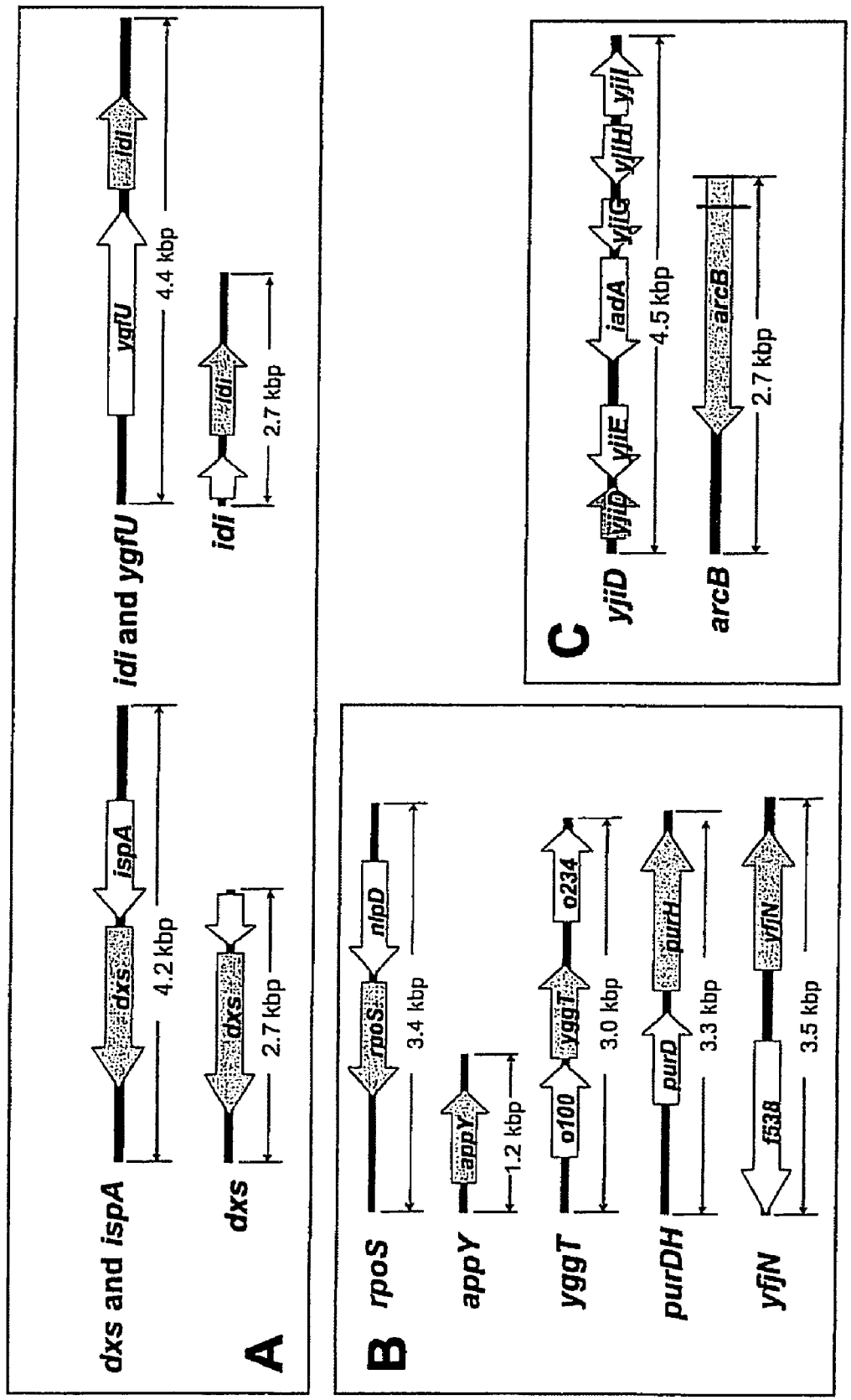
FIG. 10 schematically depicts the identification of E. coli open reading frames, which affect lycopene production when it is amplified by using multi-copy plasmids, dxs and idi genes were identified regardless of copy numbers of the plasmid used for library construction (A). rpoS, appY, yggT, purDH, yfjN gene were identified from the library made from a medium copy number plasmid (B). yjiD and arcB* were identified from the library made from a high copy number plasmid. Of the multiple ORFs in the isolated plasmids, the ORF affecting lycopene production was identified through the disruption and overexpression of each ORF in the plasmids. *as a truncated from (Δ1-102).

Open reading frame searches in the identified inserts revealed that multiple inserts contained dxs, idi, and rpoS genes. Of the 37 isolated plasmids, thirteen contained dxs gene, eight contained idi gene, and four contained rpoS. The dxs was a major ORF (13/19) identified from screening with the library based on a medium copy plasmid (FIG. 10 A), whereas the idi was a major ORF (4/10) identified screening with the library based on a high copy plasmid. The rpoS gene was consistently found (1/19, 2/8, and 1/10) in the inserts regardless of inserts size and copy numbers of the plasmids. We were also able to identify a global regulator (appY, oxidoreductases (torC, ydgK, and yeiA), and hypothetical proteins (yedR and yjiD) from the inserts (Table 6). In particular, one insert had arcB coding for a sensor kinase of a two-component system (arcA/arcB), but the N-terminal region, which is known to anchor the senor kinase to the membrane, was truncated (Δ1-102) (FIG. 10 C).

TABLE 6

Known and putative function of genes identified from the screening

| Gene | b-number | Known or putative function of the gene product |
|---|---|---|
| dxs | b0420 | 1-deoxy-D-xylulose 5-phosphate (DXP) synthase |
| idi | b2889 | isopentenyl diphosphate isomerase |
| rpoS | b2741 | RNA polymerase sigma 38 |
| torC | b0996 | trimethylamine N-oxide reductase, cytochrome c-type subunit |
| appY | b0564 | regulatory protein affecting appA and other genes |
| ydgk | b1626 | putative oxidoreductase |
| yeiA | b2147 | putative dihydrothymine dehydrogenase |
| yedR | b1963 | hypothetical protein |
| yjiD | b4326 | hypothetical protein |
| torT | b0994 | inducer-binding protein in TorSR two-component signal transduction system |
| arcB | b3210 | sensor kinase component of the Arc two-component system |
| yggT | b2952 | putative resistance protein, hypothetical integral membrane protein |

| Strain | Plasmid copy number for library construction | Average insert size (kbp) | Screen Medium | Identified inserts (frequency/number of sequenced plasmids) |
|---|---|---|---|---|
| DH5α | medium | 5 | LB | dxs (13/19), idi (4/19), rpoS (1/19), and torC (1/19) |
| DH5α | medium | 2 | LB | rpoS (2/8), appY (1/8), ydgK (2/8), dxs (1/8), yeiA (1/8), and yedR (1/8) |
| DH5α | high | 5 | LB | idi (4/10), yjiD (2/10), dxs (1/10), rpoS (1/10), torT (1/10), and arcB (1/10) |
| WS140 | medium | 5 | LB | rpoS (3/3) |
| WS140 | medium | 5 | M9 | rpoS (4/7), yggT (1/7), purDH (1/7), and yfjN (1/7) |

TABLE 6-continued

Known and putative function of genes identified from the screening

| Gene | b-number | Known or putative function of the gene product |
|---|---|---|
| purDH | b4005/6 | phosphoribosylamine-glycine ligase and AICAR transformylase/IMP cyclohydrolase |
| yfjN | b2630 | putative cell division protein |

In order to find multiple gene targets, a sequential-iterative search was performed, where next gene targets were identified following implementation of the genetic modifications suggested from the previous search.

Since dxs and idi were suggested as consensus targets from the previous screening, an *E. coli* strain (WS140) was used, which exhibited higher expression levels of dxs and idi gene, by the replacement of native promoters with a strong promoter. By using the WS140 (pACLYC) strain as a parental strain for the sequential-iterative search, four inserts were identified, which presumably improved lycopene production under the background of dxs and idi over-expression. All four insert contained the rpoS gene, which was indeed identified as a third target, following dxs and idi from the previous screening.

A sequential-iterative search was also conducted in a different environment, by changing the medium used for screening, in this case, agar plates containing M9 minimal medium with 5 g/L of glucose were used. The rpoS gene was still the dominant target (4/7) as in LB medium, but other targets yggT, pur-DH, and yfjN were also identified, genes not found in previous screenings with *E. coli* DH5 (pACLYC) strain (FIG. 10 B).

Figure 11:
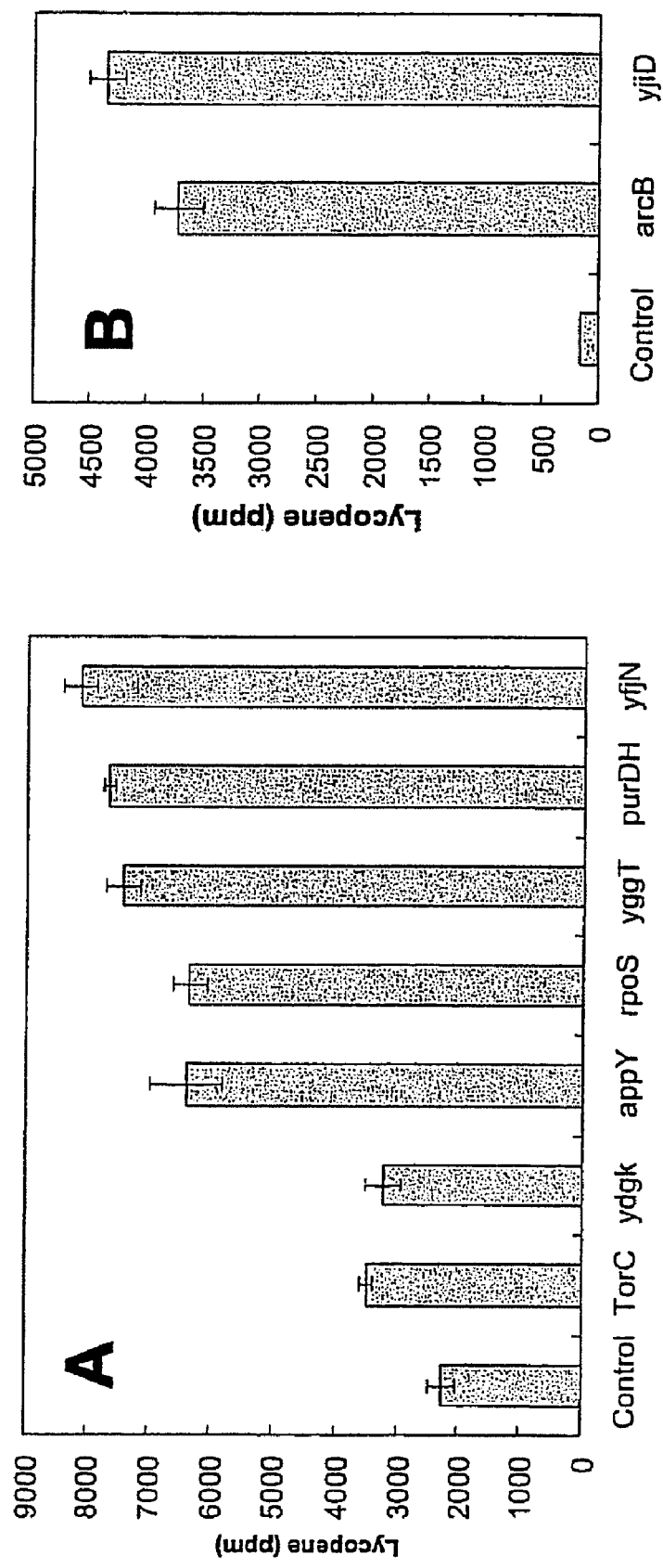
FIG. 11 graphically depicts the improvement of lycopene production in engineered E. coli WS140 strain following re-transformation with the isolated plasmids (A: medium copy plasmids, B: high copy plasmids) identified in the screening.

Of the isolated plasmids from the screenings, plasmids containing rpoS, torC, ydgK, appY, yggT, purDH, yfjN in a medium copy plasmid, and plasmids containing yjiD and arcB in a high copy plasmid were transformed into WS140 (pACLYC) for quantification of enhanced lycopene production attributable to each inset. Lycopene accumulation in 50 ml of M9 medium with 5 g/L of glucose in 250 ml flask was measured after 24 hours (FIG. 11). All the tested plasmid containing inserts accumulated more lycopene compared to a control strain containing empty plasmid. The medium copy plasmids containing rpoS, appY, yggT, purDH, and yfjN improved lycopene production more than three-fold (6000-9000 vs. 2100 ppm), while the effect of plasmids containing torC and ydgK on lycopene production was less dramatic (around 3500 ppm). The high copy plasmids containing yjiD and arcB* (as a truncated form) also improved lycopene production, as compared to the control strain (3500-4500 vs 150 ppm). Lycopene production was severely hindered by the transformation of extra plasmids, especially with a high copy plasmid.

The WS140 (pACLYC) stain, without additional plasmid, accumulated about 4300 ppm of lycopene in M9 medium with 5 g/L of glucose, but the control strain containing a medium copy plasmid without inserts produced only 2100 ppm of lycopene in the same condition. A detrimental effect of plasmid copy number on lycopene production was more obvious, when a high copy number plasmid was used. The control stain containing a high copy plasmid accumulated only 150 ppm of lycopene.

Example 9

Improvement of Lycopene Production by Combination of Isolated Overexpression Targets with Knock-Out Targets In order to investigate how phenotypes of lycopene production are mapped based on the combinations of different genetic perturbations (overexpression and knock-out), the identified overexpression targets (rpoS, appY, torC, ydgK, yggT, purDH, yfjN, and yjiD) were combined with single, double, and triple knock-out strains. Since the yjiD gene was identified in a high copy number plasmid, in order to bypass the toxic effect of the high copy number, the open reading frame of yjiD was cloned into a medium copy vector under the control of a valiant of the $P_L$. lambda promoter.

Figure 12:
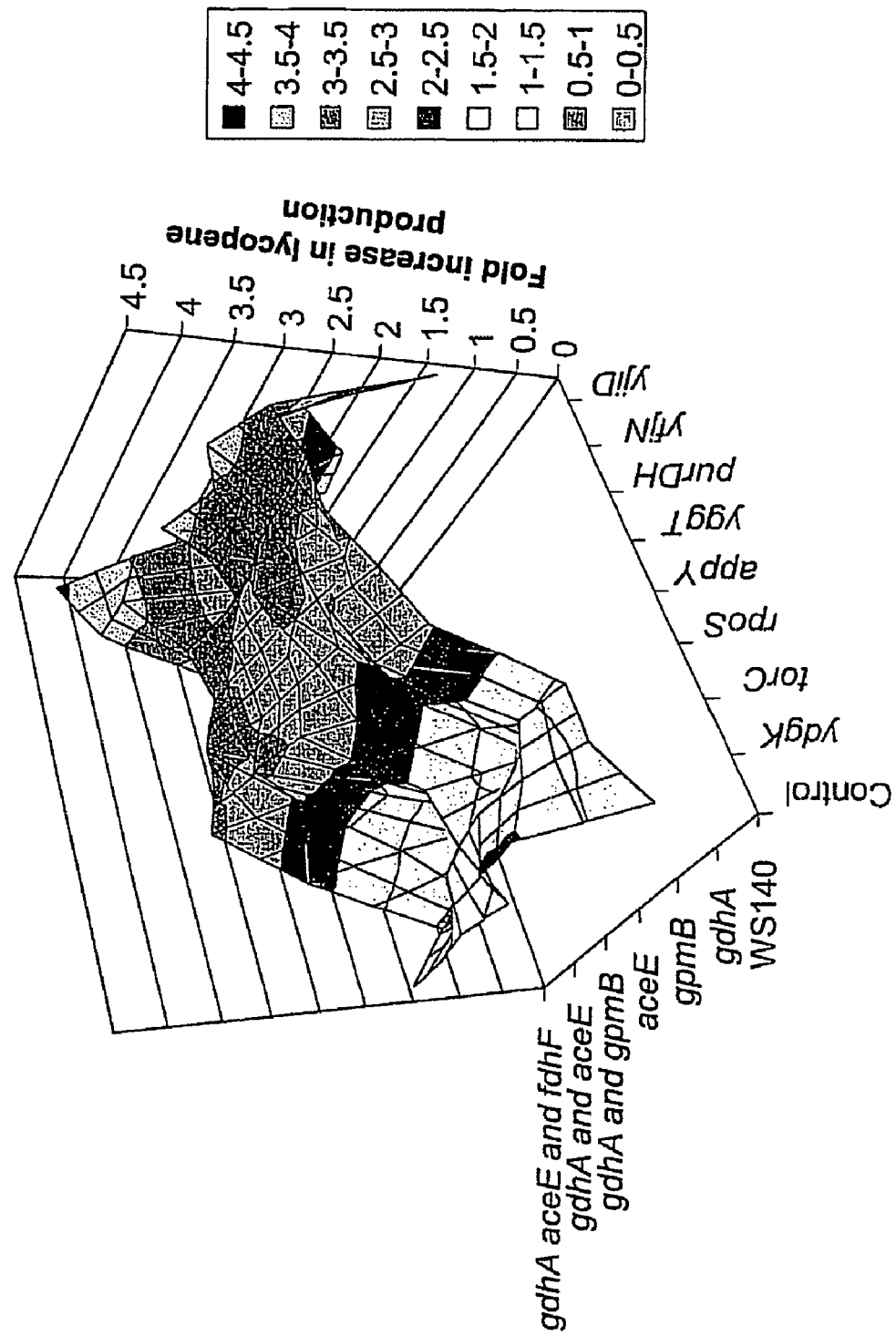
FIG. 12 graphically depicts the metabolic landscape of lycopene production in E. coli by combination of the isolated overexpression targets with knock-out strains. The open reading frame of yjiD in a high-copy plasmid was transferred into a medium copy number plasmid under the control of variant of $P_L$ lambda promoter.

Including 7 strains with a control plasmid, a total of 63 transformants (7 knock-out strains×9 plasmids) were constructed. By measuring lycopene production by the 63 strains in M9 minimal medium with 5 g/L of glucose, the metabolic landscape, which mapped the combination of genetic perturbations into lycopene production, was explored (FIG. 12).

The features of the metabolic landscape can be summarized as follows:

(1) Most of overexpression targets (except for ydgK and TorC) improved lycopene production regardless of knock-out backgrounds.

(2) The responsiveness of each knock-out strain to overexpression targets was fairly similar (3- to 4-fold increase in lycopene production).

(3) A global maximum lycopene production (9000 ppm) was found in the combination between overexpression of yjiD and triple knock-outs (ΔgdhA, ΔaceE, and ΔfdhF). The latter result may suggest that performance of most knock-out strains may be limited by regulatory or metabolic barriers, despite being designed for optimum lycopene production at the stoichiometric level.

Figure 13:
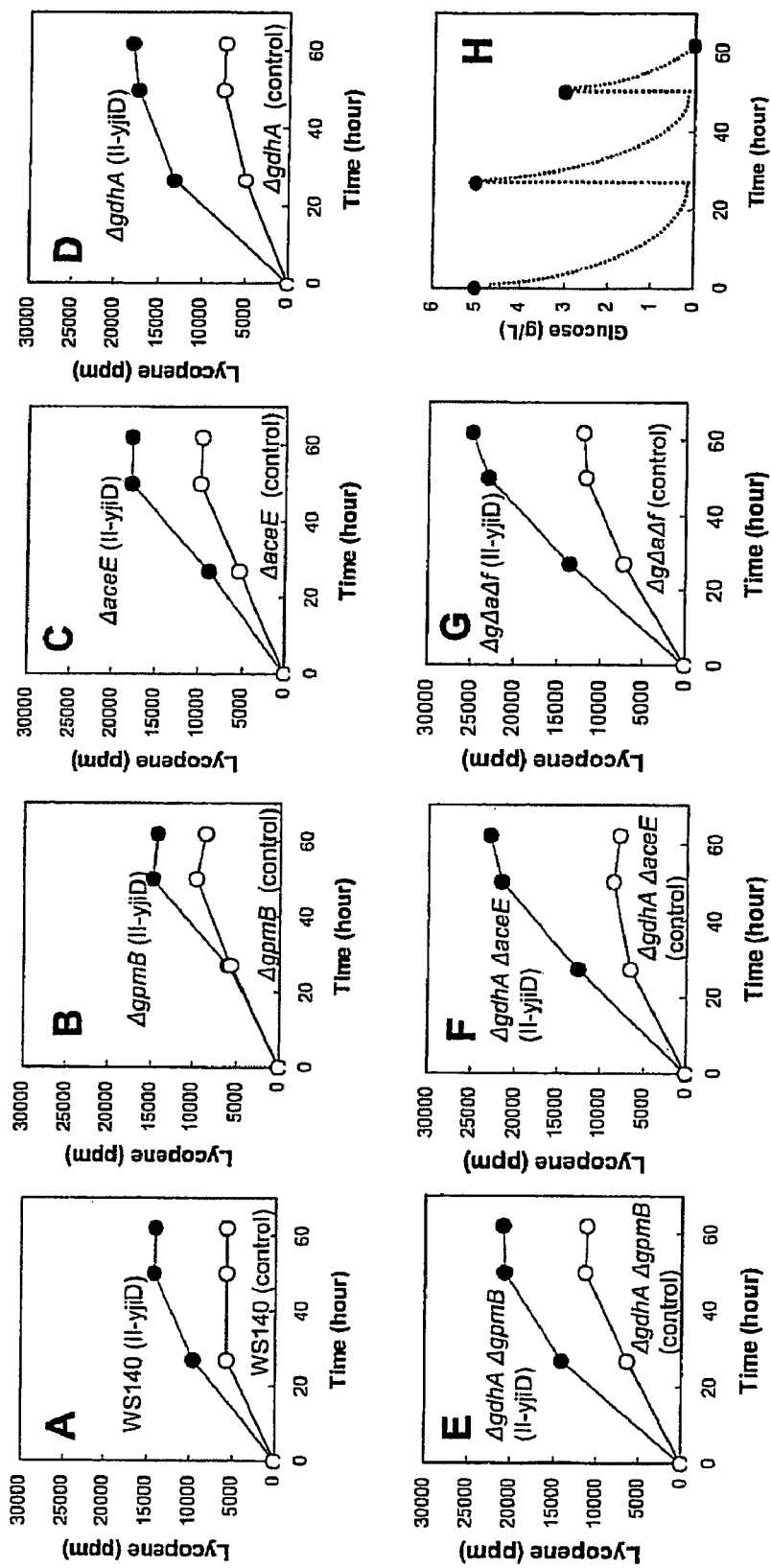
FIG. 13 graphically depicts the Improvement of lycopene accumulation by yjiD overexpression in the knockout strains (A, WS140; B, ΔgpmB; C, ΔaceE; D, ΔgdhA; E, ΔgdhA ΔgpmB; F, ΔgdhA ΔaceE; G, ΔgdhA ΔaceE ΔfdhF; H, glucose feeding profile) Initial glucose concentration was 5 g/L and glucose was added to make 5 g/L of glucose at 27 hours and additional glucose was added to make 3 g/L of glucose at 50 hours.

Since yjiD overexpression in a background of triple knock-out mutants (ΔgdhA, ΔaceE, and ΔfdhF) exhibited a global maximum in lycopene production, the effect of yjiD overexpression in a different knockout background was investigated (FIG. 13). In order to maximize the effect of genetic perturbations, 2× M9 medium, (which has been shown to be more effective for lycopene production as compared to 1× M9 medium) was used. In addition, a simple fed-batch type operation with additional intermittent feeding of glucose solution was performed, to minimize any toxic effect due to high glucose concentration (FIG. 13H).

In general, the overexpression of yjiD increased lycopene production about two-fold in all tested 7 strains with different genetic backgrounds compared to the control. The effect of yjiD overexpression was especially effective in double (ΔgdhA ΔgpmB in FIG. 13 E, ΔgdhA ΔaceE in FIG. 13 F) and triple knockout mutants (ΔgdhA, ΔaceE, and ΔfdhF in FIG. 13 G), as compared to single mutants (ΔaceE in FIG. 13 C, ΔgdhA in FIG. 13 D). Maximum lycopene accumulation (25000 ppm) was observed in the strain, which overexpressed yjiD in the triple knockout background (ΔgdhA, ΔaceE, and ΔfdhF).

Figure 14:
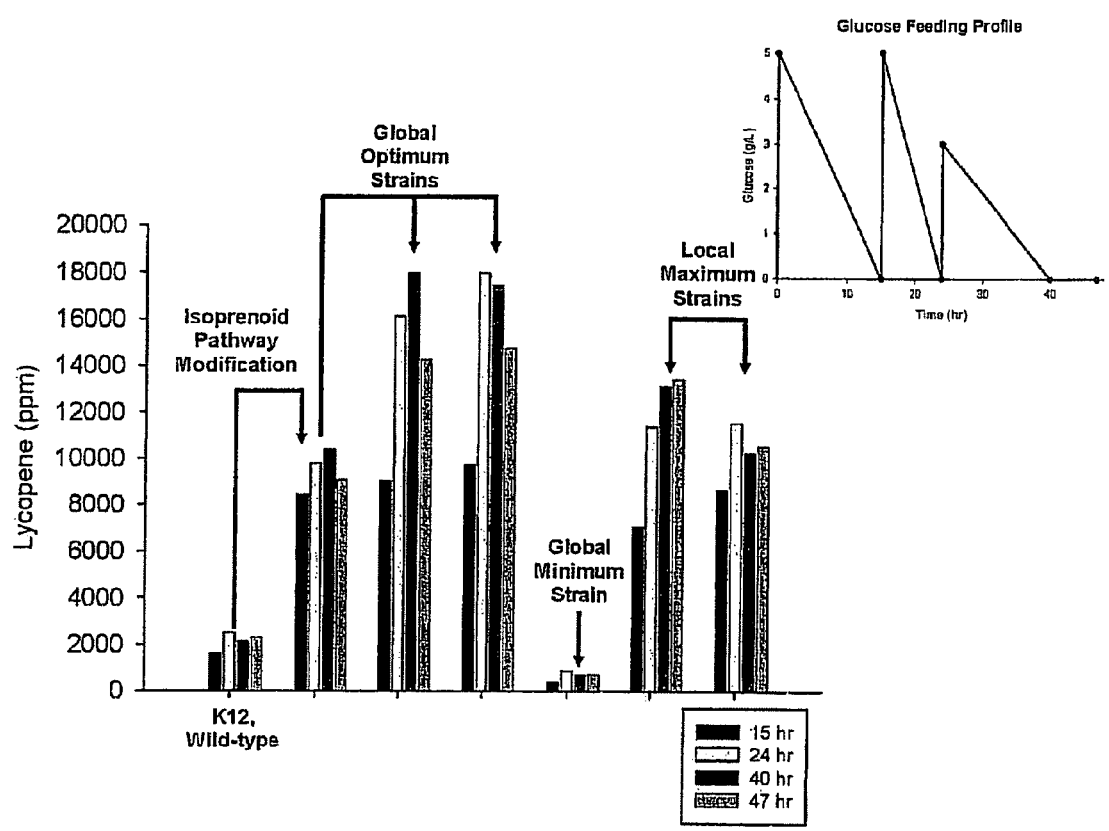
FIG. 14 graphically depicts the behavior of selected strains in optimized culturing conditions. Selected strains from the metabolic landscape were cultured in fed-batch shaker flasks with increased M9 salts and a staged glucose feed as represented in the graph. Strains presented from left to right are 1) K12 (wild-type), 2) engineered parental strain with dxs, idi, and ispFD overexpressions, 3) ΔgdhA ΔaceE ΔfdhF, 4) ΔgdhA ΔaceE ΔPyjiD, 5) ΔgdhA ΔaceE ΔfdhF Δhnr ΔyjfP, 6) ΔgdhA ΔaceE ΔfdhF ΔyjfP, and 7) ΔgdhA ΔaceE Δhnr ΔyjfP ΔPyjiD. The two global maximum were capable of producing upwards of 18,000 ppm in 24 to 40 hours. 50 ml cultures were grown in 250 ml flasks with a 1% inoculation from an overnight 5 ml culture with glucose feeds of 5 g/L at 0 and 15 hours and 3 g/L at 24 hours. M9-minimal media with double concentrations of all salts except $CaCl_2$ and $MgSO_4$ was used.

Selected strains from the metabolic landscape were cultured in fed-batch shaker flasks with increased M9 salts and a staged glucose feed, as represented in FIG. 14. The following strains were evaluated: 1) K12 (wild-type), 2) the parental strain engineered to over-express dxs, idi, and ispFD, 3) the parental strain engineered to be deleted for ΔgdhA ΔaceE ΔfdhF, ΔgdhA ΔaceE Δ$_P$yjiD, 4) the parental strain engineered to be deleted for ΔgdhA ΔaceE ΔfdhF Δhnr ΔyjfP, 5) the parental strain engineered to be deleted for ΔgdhA ΔaceE ΔfdhF ΔyjfP, and 6) the parental strain engineered to be deleted for ΔgdhA ΔaceE Δhnr ΔyjfP Δ$_P$yjiD. The two global maximum achieved under these conditions (strains 3 and 4, in the figure) produced upwards of 18,000 ppm in 24 to 40 hours.

What is claimed is:

1. A genetically engineered bacterium comprising a knockout or deletion of one or more gpmB, aceE, talB, yjiD, hnr or yjfP genes, wherein said knockout or deletion results in enhanced carotenoid production.

2. The genetically engineered bacterium of claim 1, wherein said bacterium comprises a knockout or deletion of the gene gpmB, and further comprises a knockout or deletion of the gene gdhA.

3. The genetically engineered bacterium of claim 1, wherein said bacterium comprises a knockout or deletion of the gene aceE, and further comprises a knockout or deletion of the gene gdhA.

4. The genetically engineered bacterium of claim 1, wherein said bacterium comprises a knockout or deletion of the gene talB, and further comprises a knockout or deletion of the gene gdhA.

5. The genetically engineered bacterium of claim 4, further comprising a knockout or deletion of the fdhF gene.

6. The genetically engineered bacterium of claim 1, wherein said bacterium comprises a knockout or deletion of the gene aceE, and further comprises a knockout or deletion of the genes gdhA and fdhF.

7. The genetically engineered bacterium of claim 1, wherein said bacterium comprises a knockout or deletion of the gene yjfP, and further comprises a knockout or deletion of the gene gdhA.

8. The genetically engineered bacterium of claim 1, wherein said bacterium comprises a knockout or deletion of the genes aceE and yjfP, and further comprises a knockout or deletion of the gene gdhA.

9. The genetically engineered bacterium of claim 1, wherein said bacterium comprises a knockout or deletion of the genes aceE and yjfP, and further comprises a knockout or deletion of the genes gdhA and fdhF.

10. The genetically engineered bacterium of claim 1, wherein said bacterium comprises a knockout or deletion of the genes gpmB and yjiD.

11. The genetically engineered bacterium of claim 1, wherein said bacterium comprises a knockout or deletion of the genes aceE and yjiD, and further comprises a knockout or deletion of the gene gdhA.

12. The genetically engineered bacterium of claim 1, wherein said bacterium comprises a knockout or deletion of the genes gpmB and yjiD, and further comprises a knockout or deletion of the gene gdhA.

13. The genetically engineered bacterium of claim 1, wherein said bacterium comprises a knockout or deletion of the genes aceE, hnr and yjfP, and further comprises a knockout or deletion of the gene gdhA.

14. The genetically engineered bacterium of claim 1, wherein said bacterium comprises a knockout or deletion of the genes aceE, hnr, yjfP and yjiD, and further comprises a knockout or deletion of the gene gdhA.

15. The genetically engineered bacterium of claim 1, wherein said bacterium comprises a knockout or deletion of the genes gpmB and yjfP, and further comprises a knockout or deletion of the gene gdhA.

16. The genetically engineered bacterium of claim 1, wherein said bacterium over-expresses dxs, idi, ispFD, yjiD, rpoS, torC, appY, ydgK, yeiA, yedR, tort, arcB, yggT, purDH, yfjN, or a combination thereof.

17. The genetically engineered bacterium of claim 1, further comprising a knockout or deletion of the gdhA or ppc gene.

18. A genetically engineered bacterium comprising a knockout or deletion of the gene fdhF, and further comprising a knockout or deletion of the gene gdhA.

19. A genetically engineered bacterium comprising a knockout or deletion in the genes gdhA and ppc, wherein said knockout or deletion results in enhanced carotenoid production.

20. A method for enhanced production of carotenoids, comprising:
   i. genetically disrupting by knockout or deletion of a gdhA, gpmB aceE, ppc, talB, fdhF, yjiD, hnr or yjfP gene, or a combination thereof in a cell comprising genes involved in the carotenoid biosynthetic pathway, wherein said disrupting inhibits the expression, activity or function of the gene or gene product and results in increased carotenoid production;
   ii. culturing said cells of (i) under conditions allowing production of carotenoids; and
   iii. isolating carotenoids from said cell in (i), thereby producing carotenoids.

21. The method of claim 20, wherein the genes gdhA and gpmB are disrupted.

22. The method of claim 21, wherein the gene yjfP is disrupted.

23. The method of claim 21, wherein the genes aceE and yjfP are disrupted.

24. The method of claim 20, wherein the genes gdhA and aceE are disrupted.

25. The method of claim 20, wherein the genes gdhA and ppc are disrupted.

26. The method of claim 20, wherein the genes gdhA and fdhF are disrupted.

27. The method of claim 20, wherein the genes gdhA and talB are disrupted.

28. The method of claim 27, wherein the gene fdhF is disrupted.

29. The method of claim 20, wherein the genes gdhA, aceE and fdhF are disrupted.

30. The method of claim 20, wherein the genes gdhA, aceE, fdhF and yjfP are disrupted.

31. The method of claim 20, wherein the genes gpmB and yjiD are disrupted.

32. The method of claim 20, wherein the genes gdhA, aceE, and yjiD are disrupted.

33. The method of claim 20, wherein the genes gdhA, gpmB and yjiD are disrupted.

34. The method of claim 20, wherein the genes gdhA, aceE, hnr and yjfP are disrupted.

35. The method of claim 20, wherein the genes gdhA, aceE, hnr, yjfP and yjiD are disrupted.

36. The method of claim 20, wherein the genes gdhA, gpmB and yjfP are disrupted.

37. The method of claim 20, wherein genetically disrupting a gdhA, gpmB, aceE, ppc, talB, fdhF, yjiD, hnr or yjfP gene, or a combination thereof results in an increased production of between 3 and 95%, as compared to wild-type cells.

38. The method of claim 20, further comprising the step of engineering said cell to over-express a dxs, idi, yjiD, rpoS, torC, appY, ydgK, yeiA, yedR, tort, arcB, yggT, purDH, or yfjN gene, or a combination thereof.

39. The method of claim 38, wherein engineering said cell to over-express said gene is accomplished with the use of a plasmid, which is a high-copy plasmid.

40. The method of claim 38, wherein engineering said cell to over-express said gene is accomplished with the use of a plasmid, which is a low-copy plasmid.

41. The method of claim 20, wherein said carotenoids comprise astaxanthin, canthaxanthin, beta-carotene, lycopene, phytoene or zeaxanthin.

* * * * *

SEQUENCE LISTING

<160> NUMBER OF SEQ ID NOS: 22

<210> SEQ ID NO 1
<211> LENGTH: 60
<212> TYPE: DNA
<213> ORGANISM: Artificial Sequence
<220> FEATURE:
<221> NAME/KEY: Source
<222> LOCATION: (1)..(60)
<223> OTHER INFORMATION: Synthetic construct

<400> SEQUENCE: 1
aaccatgtcc aaaagcgcga cccgaatcaa accgagttcg gtgtaggctg gagctgcttc            60

<210> SEQ ID NO 2
<211> LENGTH: 60
<212> TYPE: DNA
<213> ORGANISM: Artificial Sequence
<220> FEATURE:
<221> NAME/KEY: Source
<222> LOCATION: (1)..(60)
<223> OTHER INFORMATION: Synthetic construct

<400> SEQUENCE: 2
tcacaccctg cgccagcatc gcatcggcaa ccttcacaag ggatccgtcg acctgcagtt            60

<210> SEQ ID NO 3
<211> LENGTH: 20
<212> TYPE: DNA
<213> ORGANISM: Artificial Sequence
<220> FEATURE:
<221> NAME/KEY: Source
<222> LOCATION: (1)..(20)
<223> OTHER INFORMATION: Synthetic construct

<400> SEQUENCE: 3
gataagcgta gcgccatcag                                                       20

<210> SEQ ID NO 4
<211> LENGTH: 60
<212> TYPE: DNA
<213> ORGANISM: Artificial Sequence
<220> FEATURE:
<221> NAME/KEY: Source
<222> LOCATION: (1)..(60)
<223> OTHER INFORMATION: Synthetic construct

<400> SEQUENCE: 4
gggccagtct gacagcccgc tgaccgccaa aggtgagcaa gtgtaggctg gagctgcttc            60

<210> SEQ ID NO 5
<211> LENGTH: 60
<212> TYPE: DNA
<213> ORGANISM: Artificial Sequence
<220> FEATURE:
<221> NAME/KEY: Source
<222> LOCATION: (1)..(60)
<223> OTHER INFORMATION: Synthetic construct

<400> SEQUENCE: 5
cggcgctctg cccatgctgg taatccgaga atcgtactca tccgtcgacc tgcagttcga            60

<210> SEQ ID NO 6
<211> LENGTH: 20
<212> TYPE: DNA
<213> ORGANISM: Artificial Sequence

```
<220> FEATURE:
<221> NAME/KEY: Source
<222> LOCATION: (1)..(20)
<223> OTHER INFORMATION: Synthetic construct

<400> SEQUENCE: 6
cccaattaat ctacgctgtg                                                 20

<210> SEQ ID NO 7
<211> LENGTH: 60
<212> TYPE: DNA
<213> ORGANISM: Artificial Sequence
<220> FEATURE:
<221> NAME/KEY: Source
<222> LOCATION: (1)..(60)
<223> OTHER INFORMATION: Synthetic construct

<400> SEQUENCE: 7
taaattcctg aaatatctgg aacaccgtgg cctgaaagat gtgtaggctg gagctgcttc     60

<210> SEQ ID NO 8
<211> LENGTH: 60
<212> TYPE: DNA
<213> ORGANISM: Artificial Sequence
<220> FEATURE:
<221> NAME/KEY: Source
<222> LOCATION: (1)..(60)
<223> OTHER INFORMATION: Synthetic construct

<400> SEQUENCE: 8
tggaagccga acatcgagta atagatgtag aacgggatca tccgtcgacc tgcagttcga     60

<210> SEQ ID NO 9
<211> LENGTH: 20
<212> TYPE: DNA
<213> ORGANISM: Artificial Sequence
<220> FEATURE:
<221> NAME/KEY: Source
<222> LOCATION: (1)..(20)
<223> OTHER INFORMATION: Synthetic construct

<400> SEQUENCE: 9
acgctccaga ccgtcatgca                                                 20

<210> SEQ ID NO 10
<211> LENGTH: 60
<212> TYPE: DNA
<213> ORGANISM: Artificial Sequence
<220> FEATURE:
<221> NAME/KEY: Source
<222> LOCATION: (1)..(60)
<223> OTHER INFORMATION: Synthetic construct

<400> SEQUENCE: 10
agctcaatac ccgcttttc gcaggttttg attaatgcat gtgtaggctg gagctgcttc      60

<210> SEQ ID NO 11
<211> LENGTH: 60
<212> TYPE: DNA
<213> ORGANISM: Artificial Sequence
<220> FEATURE:
<221> NAME/KEY: Source
<222> LOCATION: (1)..(60)
<223> OTHER INFORMATION: Synthetic construct

<400> SEQUENCE: 11
ggaagtgaac gcctgtttaa aacagctcga taacaaagat ggatccgtcg acctgcagtt    60
```

<210> SEQ ID NO 12
<211> LENGTH: 25
<212> TYPE: DNA
<213> ORGANISM: Artificial Sequence
<220> FEATURE:
<221> NAME/KEY: Source
<222> LOCATION: (1)..(25)
<223> OTHER INFORMATION: Synthetic construct

<400> SEQUENCE: 12
gcaaagtgct gggagaaacc atcaa                                  25

<210> SEQ ID NO 13
<211> LENGTH: 60
<212> TYPE: DNA
<213> ORGANISM: Artificial Sequence
<220> FEATURE:
<221> NAME/KEY: Source
<222> LOCATION: (1)..(60)
<223> OTHER INFORMATION: Synthetic construct

<400> SEQUENCE: 13
atgacggaca aattgacctc ccttcgtcag tacaccaccg gtgtaggctg gagctgcttc    60

<210> SEQ ID NO 14
<211> LENGTH: 60
<212> TYPE: DNA
<213> ORGANISM: Artificial Sequence
<220> FEATURE:
<221> NAME/KEY: Source
<222> LOCATION: (1)..(60)
<223> OTHER INFORMATION: Synthetic construct

<400> SEQUENCE: 14
acggatacct tccgccagtt tatctactgc cattggatcc tccgtcgacc tgcagttcga    60

<210> SEQ ID NO 15
<211> LENGTH: 30
<212> TYPE: DNA
<213> ORGANISM: Artificial Sequence
<220> FEATURE:
<221> NAME/KEY: Source
<222> LOCATION: (1)..(30)
<223> OTHER INFORMATION: Synthetic construct

<400> SEQUENCE: 15
tgatacactg cgaagggagt gacagacagg                             30

<210> SEQ ID NO 16
<211> LENGTH: 60
<212> TYPE: DNA
<213> ORGANISM: Artificial Sequence
<220> FEATURE:
<221> NAME/KEY: Source
<222> LOCATION: (1)..(60)
<223> OTHER INFORMATION: Synthetic construct

<400> SEQUENCE: 16
acggtaaaat aacatccgcc gccgacgcgg ttttggtcat gtgtaggctg gagctgcttc    60

<210> SEQ ID NO 17
<211> LENGTH: 60
<212> TYPE: DNA
<213> ORGANISM: Artificial Sequence
<220> FEATURE:
<221> NAME/KEY: Source
<222> LOCATION: (1)..(60)
<223> OTHER INFORMATION: Synthetic construct

<400> SEQUENCE: 17
gcatcaggtt gcaaaatcaa cctggtcgtc gataacggca tccgtcgacc tgcagttcga     60

<210> SEQ ID NO 18
<211> LENGTH: 20
<212> TYPE: DNA
<213> ORGANISM: Artificial Sequence
<220> FEATURE:
<221> NAME/KEY: Source
<222> LOCATION: (1)..(20)
<223> OTHER INFORMATION: Synthetic construct

<400> SEQUENCE: 18
cgcggtattt cgtttcgtca     20

<210> SEQ ID NO 19
<211> LENGTH: 26
<212> TYPE: DNA
<213> ORGANISM: Artificial Sequence
<220> FEATURE:
<221> NAME/KEY: Source
<222> LOCATION: (1)..(26)
<223> OTHER INFORMATION: Synthetic construct

<400> SEQUENCE: 19
tatcaggaca tagcgttggc tacccg     26

<210> SEQ ID NO 20
<211> LENGTH: 20
<212> TYPE: DNA
<213> ORGANISM: Artificial Sequence
<220> FEATURE:
<221> NAME/KEY: Source
<222> LOCATION: (1)..(20)
<223> OTHER INFORMATION: Synthetic construct

<400> SEQUENCE: 20
cggcgaatgg gctgaccgct     20

<210> SEQ ID NO 21
<211> LENGTH: 24
<212> TYPE: DNA
<213> ORGANISM: Artificial Sequence
<220> FEATURE:
<221> NAME/KEY: Source
<222> LOCATION: (1)..(24)
<223> OTHER INFORMATION: Synthetic construct

<400> SEQUENCE: 21
tcgtgcttta cggtatcgcc gctc     24

<210> SEQ ID NO 22
<211> LENGTH: 22
<212> TYPE: DNA
<213> ORGANISM: Artificial Sequence
<220> FEATURE:
<221> NAME/KEY: Source
<222> LOCATION: (1)..(22)
<223> OTHER INFORMATION: Synthetic construct

<400> SEQUENCE: 22
catcgccttc tatcgccttc tt     22